United States Patent
Ammendola et al.

(10) Patent No.: US 11,957,749 B2
(45) Date of Patent: *Apr. 16, 2024

(54) HEPATITIS B IMMUNIZATION REGIMEN AND COMPOSITIONS

(71) Applicant: GLAXOSMITHKLINE BIOLOGICALS SA, Rixensart (BE)

(72) Inventors: Virginia Ammendola, Rome (IT); Babak Bayat, Rixensart (BE); Clarisse Lorin, Rixensart (BE); Ventzislav Bojidarov Vassilev, Rixensart (BE); Alessandra Vitelli, Rome (IT)

(73) Assignee: GlaxoSmithKline Biologicals SA (BE)

( * ) Notice: Subject to any disclaimer, the term of this patent is extended or adjusted under 35 U.S.C. 154(b) by 284 days.

This patent is subject to a terminal disclaimer.

(21) Appl. No.: 16/772,194

(22) PCT Filed: Dec. 14, 2018

(86) PCT No.: PCT/EP2018/085086
§ 371 (c)(1),
(2) Date: Jun. 12, 2020

(87) PCT Pub. No.: WO2019/115817
PCT Pub. Date: Jun. 20, 2019

(65) Prior Publication Data
US 2021/0154290 A1    May 27, 2021

(30) Foreign Application Priority Data
Dec. 15, 2017  (GB) .................... 1721069

(51) Int. Cl.
| | | |
|---|---|---|
| A61K 39/29 | (2006.01) | |
| A61K 39/39 | (2006.01) | |
| A61P 31/20 | (2006.01) | |
| C07K 14/005 | (2006.01) | |
| C12N 7/00 | (2006.01) | |
| A61K 39/00 | (2006.01) | |

(52) U.S. Cl.
CPC ............ *A61K 39/292* (2013.01); *A61K 39/39* (2013.01); *A61P 31/20* (2018.01); *C07K 14/005* (2013.01); *C12N 7/00* (2013.01); *A61K 2039/5254* (2013.01); *A61K 2039/5256* (2013.01); *A61K 2039/55555* (2013.01); *A61K 2039/55572* (2013.01); *A61K 2039/55577* (2013.01); *A61K 2039/57* (2013.01); *C07K 2319/40* (2013.01); *C12N 2710/10343* (2013.01); *C12N 2710/24143* (2013.01); *C12N 2730/10122* (2013.01); *C12N 2730/10134* (2013.01)

(58) Field of Classification Search
CPC ........... C12N 2710/24034; C12N 2710/16622; C12N 2710/16271; C12N 2710/16034; C12N 2710/16234; C12N 2710/16222; C12N 15/70; C12N 2710/10311; C12N 2710/10343; C12N 2710/24143; A61K 39/29; A61K 2039/523; A61K 2039/6075; A61K 47/6901; A61K 39/235; A61K 39/275; A61K 2039/522; A61K 2039/55577; A61K 39/12; A61K 39/292; A61P 31/20

See application file for complete search history.

(56) References Cited

U.S. PATENT DOCUMENTS

| | | |
|---|---|---|
| 11,571,472 B2 | 2/2023 | Steff et al. |
| 2010/0278904 A1 | 11/2010 | Holst et al. |
| 2011/0059132 A1 | 3/2011 | Melber et al. |

FOREIGN PATENT DOCUMENTS

| | | |
|---|---|---|
| EP | 2974740 A1 | 1/2016 |
| WO | 2008/031878 A1 | 3/2008 |
| WO | 2011/015656 A2 | 2/2011 |
| WO | 2015/082922 A1 | 6/2015 |
| WO | 2015189425 A1 | 12/2015 |
| WO | WO2016020538 | * 2/2016 |
| WO | 2017013169 A1 | 1/2017 |
| WO | 2017017050 A1 | 2/2017 |
| WO | 2017/121791 A1 | 7/2017 |

OTHER PUBLICATIONS

Backes et al. (Vaccine 2016, vol. 34 (7), pp. 923-932).*
Kunke David et al. "Vaccinia Virus Recombinants Coexpressing Hepatitis B Virus Surface and Core Antigens." Virology; 1993; pp. 132-139; vol. 195.
Perrine Martin et al. "TG1050, an immunotherapeutic to treat chronic hepatitis B, induces robust T cells and exerts an antivrial effect in HBV-persisten mic." Gut; 2014; pp. 1961-1971; vol. 64(12).
Katie Ewer et al. "Chimpanzee adenoviral vectors as vaccines for outbreak pathogens" Human Vaccines and Immunotherapeutics; 2017; pp. 3020-3032; vol. 13(12).
Sarah Kutscher et al. "Design of therapeutic vaccines: hepatitis B as an example: Immune therapy of hepatitis B virus infection." Microbial Biotechnology; 2011; pp. 270-282; vol. 5(2).

(Continued)

*Primary Examiner* — Bao Q Li
(74) *Attorney, Agent, or Firm* — Hao Yin

(57) ABSTRACT

The present invention relates to immunogenic compositions and combinations thereof which may find use in immunisation regimens for the treatment of chronic hepatitis B. An immunogenic composition comprises a replication-defective chimpanzee adenoviral (ChAd) vector comprising polynucleotides encoding HBs, HBc human invariant chain (hIi) fused to the HBc. Another immunogenic composition comprises a Modified Vaccinia Virus Ankara (MVA) vector comprising polynucleotides encoding HBs and HBc. Another immunogenic composition comprises recombinant HBs, C-terminal truncated recombinant HBc and an adjuvant containing MPL and QS-21.

9 Claims, 25 Drawing Sheets

Figure 1A:
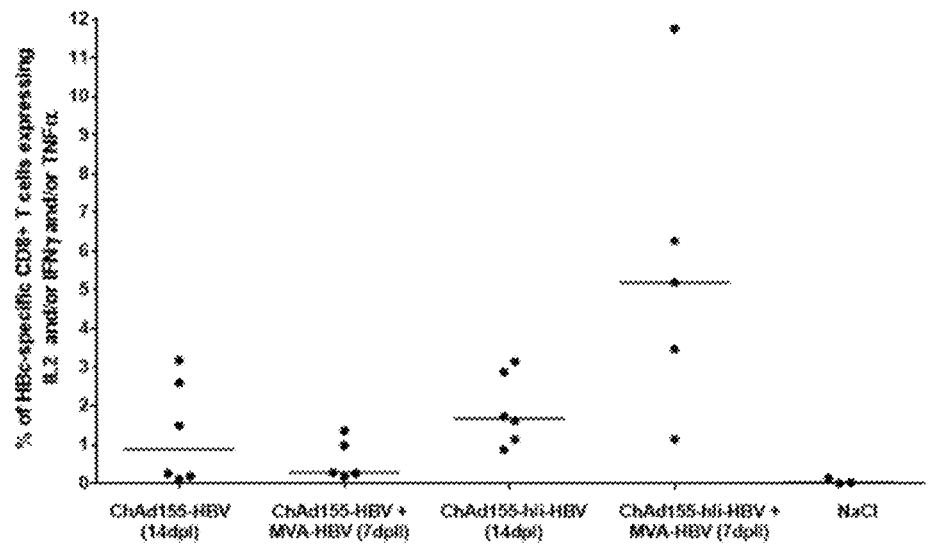

Specification includes a Sequence Listing.

(56) References Cited

OTHER PUBLICATIONS

Geert Leroux-Roels et al. "Vaccine Adjuvant Systems containing monophosphoryl lipid A and QS-21 induce strong humoral and cellular immune responses against hepatitis B surface antigen which persist for at least 4 years after vaccination." Vaccine; 2015; pp. 1084-1091; vol. 33(8).

Maryline Bourgine et al. "Optimization of immune responses induced by therapeutic vaccination with cross-reactive antigens in a humanized hepatitis B surface antigen transgenic mouse model." Virology; 2012; pp. 10-19; vol. 430(1).

Anonymous: "ChAd155-hli-HBV and MVA-HBV" Feb. 1, 2018; pp. 1-45; retrieved from the Internet: URL:https://www.health.belgium.be/sites/default/files/uploads/fields/fpshealth_theme_file/18bvw4_combinedsnif_chad155-hii-hbv_and_mva_hbv.pdf.

Depla E et al. "Rational Design of a Multiepitope Vaccine Encoding T-Lymphocyte Epitopes for Treatment of Chronic Hepatitis B Virus Infections." Journal of Virology; 2008; pp. 435-450; vol. 82(1).

Jin Hee Kim et al. "High Cleavage Efficiency of a 2A Peptide Derived from Porcine Teschovirus-1 in Human Cell Lines, Zebrafish and Mice." PLOS One; 2011; pp. e18556; vol. 6(4).

Jianqiang Li et al. "Hepatitis B surface antigen (HBsAg) and core antigen (HBcAg) combine CpG oligodeoxynucleotides as a novel therapeutic vaccine for chronic hepatitis B infection." Vaccine; 2015; pp. 4247-4254; vol. 33(35).

Chen X et al. "Recombinant hepatitis B core antigen carrying preS1 epitopes induce immune response against chronic HBV infection." Vaccine; 2004; pp. 439-446; vol. 22 (3-4).

Douglas A D et al. "Tailoring subunit vaccine immunogenicity: Maximizing antibody and T cell responses by using combinations of adenovirus, poxvirus and protein-adjuvant vaccines against Plasmodium falciparum MSP1." Vaccine; 2010; pp. 7167-7178; vol. 28(44).

Capone S. et al. "Fusion of HCV nonstructural antigen to MHC class II-associated invariant chain enhances T-cell responses induced by vectored vaccines in nonhuman primates", Mol.Ther., 2014, vol. 22, No. 5, pp. 1039-1047.

Jäger, Clemens, "Therapeutic vaccination using MVA vectors in a murine model of chronic HBV infection", Fakultät für Medizin Institut für Virologie, pp. 1-135, 2015, https://mediatum.ub.tum.de/doc/1241512/1241512.pdf.

Spencer A.J. et al. "Enhanced vaccine-induced CD8+ T cell responses to malaria antigen ME-TRAP by fusion to MHC class II invariant chain", PLOS One, 2014, vol. 9, No. 6, p. e100538.

* cited by examiner (Spleen)

(Liver)

(Spleen)

(Liver)

SEQUENCE LISTING

<160> NUMBER OF SEQ ID NOS: 15

<210> SEQ ID NO 1
<211> LENGTH: 226
<212> TYPE: PRT
<213> ORGANISM: Hepatitis B Virus

<400> SEQUENCE: 1

Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Ser Pro Val Cys
        35                  40                  45

Leu Gly Gln Asn Ser Gln Ser Pro Thr Ser Asn His Ser Pro Thr Ser
    50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Thr Thr Thr Asn Thr Gly Pro Cys Lys Thr Cys Thr Thr Pro Ala
        115                 120                 125

Gln Gly Asn Ser Met Phe Pro Ser Cys Cys Thr Lys Pro Thr Asp
    130                 135                 140

Gly Asn Cys Thr Cys Ile Pro Ile Pro Ser Ser Trp Ala Phe Ala Lys
145                 150                 155                 160

Tyr Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Ala Ile Trp Met Met Trp Tyr Trp Gly Pro Ser Leu Tyr Ser Ile
        195                 200                 205

Val Ser Pro Phe Ile Pro Leu Leu Pro Ile Phe Phe Cys Leu Trp Val
    210                 215                 220

Tyr Ile
225

<210> SEQ ID NO 2
<211> LENGTH: 149
<212> TYPE: PRT
<213> ORGANISM: Artificial
<220> FEATURE:
<223> OTHER INFORMATION: Synthetic polypeptide comprising Hepatitis B
      virus core antigen truncate

<400> SEQUENCE: 2

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala

```
                65                  70                  75                  80
Ser Arg Asp Leu Val Val Asn Tyr Val Asn Thr Asn Met Gly Leu Lys
                    85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
                115                 120                 125

Pro Pro Ala Tyr Arg Pro Pro Asn Ala Pro Ile Leu Ser Thr Leu Pro
            130                 135                 140

Glu Thr Thr Val Val
145

<210> SEQ ID NO 3
<211> LENGTH: 24
<212> TYPE: PRT
<213> ORGANISM: Artificial
<220> FEATURE:
<223> OTHER INFORMATION: Synthetic polypeptide spacer comprising 2A
      cleavage region of foot and mouth virus

<400> SEQUENCE: 3

Ala Pro Val Lys Gln Thr Leu Asn Phe Asp Leu Leu Lys Leu Ala Gly
1               5                   10                  15

Asp Val Glu Ser Asn Pro Gly Pro
            20

<210> SEQ ID NO 4
<211> LENGTH: 72
<212> TYPE: DNA
<213> ORGANISM: Artificial
<220> FEATURE:
<223> OTHER INFORMATION: Synthetic polynucleotide coding polypeptide
      spacer comprising 2A cleavage region of foot and mouth virus

<400> SEQUENCE: 4
gcccctgtga agcagaccct gaacttcgac ctgctgaagc tggccggcga cgtggagagc    60
aatcccggcc ct                                                       72

<210> SEQ ID NO 5
<211> LENGTH: 435
<212> TYPE: PRT
<213> ORGANISM: Artificial
<220> FEATURE:
<223> OTHER INFORMATION: Synthetic polypeptide HBc-2A-HBs comprising
      Hepatitis B core antigen truncate-spacer comprising 2A cleavage
      region of foot and mouth virus-Hepatitis B surface antigen

<400> SEQUENCE: 5

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                    85                  90                  95
```

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Asp Arg Gly Arg Ser Pro Arg Arg
145                 150                 155                 160

Arg Thr Pro Ser Pro Arg Arg Arg Ser Gln Ser Pro Arg Arg Arg
                165                 170                 175

Arg Ser Gln Ser Arg Glu Ser Gln Cys Ala Pro Val Lys Gln Thr Leu
                180                 185                 190

Asn Phe Asp Leu Leu Lys Leu Ala Gly Asp Val Glu Ser Asn Pro Gly
            195                 200                 205

Pro Met Glu Asn Ile Thr Ser Gly Phe Leu Gly Pro Leu Leu Val Leu
    210                 215                 220

Gln Ala Gly Phe Phe Leu Leu Thr Arg Ile Leu Thr Ile Pro Gln Ser
225                 230                 235                 240

Leu Asp Ser Trp Trp Thr Ser Leu Asn Phe Leu Gly Gly Ser Pro Val
                245                 250                 255

Cys Leu Gly Gln Asn Ser Gln Ser Pro Thr Ser Asn His Ser Pro Thr
                260                 265                 270

Ser Cys Pro Pro Ile Cys Pro Gly Tyr Arg Trp Met Cys Leu Arg Arg
            275                 280                 285

Phe Ile Ile Phe Leu Phe Ile Leu Leu Leu Cys Leu Ile Phe Leu Leu
    290                 295                 300

Val Leu Leu Asp Tyr Gln Gly Met Leu Pro Val Cys Pro Leu Ile Pro
305                 310                 315                 320

Gly Ser Thr Thr Thr Asn Thr Gly Pro Cys Lys Thr Cys Thr Thr Pro
                325                 330                 335

Ala Gln Gly Asn Ser Met Phe Pro Ser Cys Cys Cys Thr Lys Pro Thr
                340                 345                 350

Asp Gly Asn Cys Thr Cys Ile Pro Ile Pro Ser Ser Trp Ala Phe Ala
            355                 360                 365

Lys Tyr Leu Trp Glu Trp Ala Ser Val Arg Phe Ser Trp Leu Ser Leu
    370                 375                 380

Leu Val Pro Phe Val Gln Trp Phe Val Gly Leu Ser Pro Thr Val Trp
385                 390                 395                 400

Leu Ser Ala Ile Trp Met Met Trp Tyr Trp Gly Pro Ser Leu Tyr Ser
                405                 410                 415

Ile Val Ser Pro Phe Ile Pro Leu Leu Pro Ile Phe Phe Cys Leu Trp
            420                 425                 430

Val Tyr Ile
        435

<210> SEQ ID NO 6
<211> LENGTH: 1305
<212> TYPE: DNA
<213> ORGANISM: Artificial
<220> FEATURE:
<223> OTHER INFORMATION: Synthetic polynucleotide coding for HBc-2A-HBs
      polypetide comprising Hepatitis B core antigen truncate-spacer
      comprising 2A cleavage region of foot and mouth virus- Hepatitis B
      surface antigen truncate

<400> SEQUENCE: 6

```
atggacatcg atccctacaa ggaatttggc gccaccgtgg agctgctgag cttcctgccc      60
agcgacttct tccccagcgt gagggacctc ctggacaccg ccagcgccct gtacagggag     120
gccctggaat ctcccgagca ctgcagccca caccacaccg cactgaggca ggccatcctg     180
tgctggggag agctgatgac cctcgccacc tgggtgggca caacctgga ggaccccgcc      240
agcagggacc tggtggtgaa ctacgtcaac accaacatgg gcctgaagat caggcagctg     300
ctgtggttcc acatcagctg cctgaccttc gcaggagaga ccgtgctgga gtacctggtg     360
agcttcggcg tgtggatcag gacacctccc gcctacagac cccccaacgc ccccatcctg     420
agcacccctg ccgagaccac agtggtgagg aggagggaca ggggcaggtc acccaggagg     480
aggactccaa gccccaggag gaggaggagc cagagcccca ggagaaggag gagccagagc     540
agggagagcc agtgcgcccc tgtgaagcag accctgaact tcgacctgct gaagctggcc     600
ggcgacgtgg agagcaatcc cggccctatg agaaacatca ccagcggctt cctgggcccc     660
ctgctggtgc tgcaggcagg cttcttcctg ctgaccagga tcctgaccat ccccagagc      720
ctggacagct ggtggaccag cctgaacttc ctcggcggga gccccgtgtg cctgggccag     780
aacagccagt ctcccaccag caatcacagc cccaccagct gccccccaat ctgtcctggc     840
taccggtgga tgtgcctgag gaggttcatc atcttcctgt tcatcctgct cctgtgcctg     900
atcttcctgc tggtgctgct ggactaccag ggaatgctgc cagtgtgtcc cctgatcccc     960
ggctcaacca ccactaacac cggccctgc aaaacctgca ccacccccgc tcagggcaac     1020
agcatgttcc aagctgctg ctgcaccaag cccaccgacg gcaactgcac ctgcattccc     1080
atccccagca gctgggcctt cgccaagtat ctgtgggagt gggccagcgt gaggttcagc     1140
tggctcagcc tgctggtgcc cttcgtccag tggtttgtgg gcctgagccc caccgtgtgg     1200
ctgagcgcca tctggatgat gtggtactgg ggccccagcc tgtactccat cgtgagcccc     1260
ttcatccccc tgctgcccat tttcttctgc ctgtgggtgt acatc                    1305

<210> SEQ ID NO 7
<211> LENGTH: 229
<212> TYPE: PRT
<213> ORGANISM: Artificial
<220> FEATURE:
<223> OTHER INFORMATION: Synthetic polypeptide of human invariant chain
      hIi

<400> SEQUENCE: 7

Met His Arg Arg Arg Ser Arg Ser Cys Arg Glu Asp Gln Lys Pro Val
1               5                   10                  15
Met Asp Asp Gln Arg Asp Leu Ile Ser Asn Asn Glu Gln Leu Pro Met
            20                  25                  30
Leu Gly Arg Arg Pro Gly Ala Pro Glu Ser Lys Cys Ser Arg Gly Ala
        35                  40                  45
Leu Tyr Thr Gly Phe Ser Ile Leu Val Thr Leu Leu Ala Gly Gln
    50                  55                  60
Ala Thr Thr Ala Tyr Phe Leu Tyr Gln Gln Gln Gly Arg Leu Asp Lys
65                  70                  75                  80
Leu Thr Val Thr Ser Gln Asn Leu Gln Leu Glu Asn Leu Arg Met Lys
                85                  90                  95
Leu Pro Lys Pro Lys Pro Val Ser Lys Met Arg Met Ala Thr Pro Leu
            100                 105                 110
Leu Met Gln Ala Leu Pro Met Gly Ala Leu Pro Gln Gly Pro Met Gln
            115                 120                 125
```

```
Asn Ala Thr Lys Tyr Gly Asn Met Thr Glu Asp His Val Met His Leu
    130                 135                 140

Leu Gln Asn Ala Asp Pro Leu Lys Val Tyr Pro Pro Leu Lys Ser Phe
145                 150                 155                 160

Pro Glu Asn Leu Arg His Leu Lys Asn Thr Met Glu Thr Ile Asp Trp
                165                 170                 175

Lys Val Phe Glu Ser Trp Met His His Trp Leu Leu Phe Glu Met Ser
            180                 185                 190

Arg His Ser Leu Glu Gln Lys Pro Thr Asp Ala Pro Pro Lys Glu Ser
        195                 200                 205

Leu Glu Leu Glu Asp Pro Ser Ser Gly Gly Val Thr Lys Gln Asp Leu
210                 215                 220

Gly Pro Val Pro Met
225

<210> SEQ ID NO 8
<211> LENGTH: 696
<212> TYPE: DNA
<213> ORGANISM: Artificial
<220> FEATURE:
<223> OTHER INFORMATION: Synthetic polynucleotide encoding the human
      invariant chain hIi

<400> SEQUENCE: 8
atgcacagga ggaggagcag gagctgcagg gaggaccaga agcccgtgat ggacgaccag      60
cgcgacctga tcagcaacaa cgagcagctg ccaatgctgg gcaggaggcc cggagcaccc    120
gaaagcaagt gcagcagggg cgccctgtac accggcttca gcatcctggt gaccctcctg    180
ctggccggcc aggccaccac cgcctatttc ctgtaccagc agcagggcag gctcgataag    240
ctgaccgtga cctcccagaa cctgcagctg agaaacctga ggatgaagct gcccaagccc    300
cccaagcccg tgagcaagat gaggatggcc accccctgc tgatgcaggc tctgcccatg    360
ggggccctgc cccagggccc catgcagaac gccaccaaat acggcaacat gaccgaggac    420
cacgtgatgc acctgctgca gaacgccgat cctctgaagg tgtacccacc cctgaaaggc    480
agcttccccg agaaccctca gcacctgaag aacaccatgg agaccatcga ctggaaggtg    540
ttcgagagct ggatgcacca ctggctgctg ttcgagatga gccggcacag cctggagcag    600
aagcccaccg acgcccctcc aaggagagc ctcgagctcg aggacccaag cagcggcctg    660
ggcgtgacca gcaggacct gggccccgtg cccatg                               696

<210> SEQ ID NO 9
<211> LENGTH: 628
<212> TYPE: PRT
<213> ORGANISM: Artificial
<220> FEATURE:
<223> OTHER INFORMATION: Synthetic polypeptide hIi-HBc-2A-HBs comprising
      human invriant chain-Hepatitis B core antigen truncate-spacer
      comprising 2A cleavage region of foot and mouth virus-Hepatitis B
      surface antigen truncate

<400> SEQUENCE: 9

Met His Arg Arg Arg Ser Arg Ser Cys Arg Glu Asp Gln Lys Pro Val
1               5                   10                  15

Met Asp Asp Gln Arg Asp Leu Ile Ser Asn Asn Glu Gln Leu Pro Met
                20                  25                  30

Leu Gly Arg Arg Pro Gly Ala Pro Glu Ser Lys Cys Ser Arg Gly Ala
            35                  40                  45

Leu Tyr Thr Gly Phe Ser Ile Leu Val Thr Leu Leu Leu Ala Gly Gln
```

```
              50                  55                  60
Ala Thr Thr Ala Tyr Phe Leu Tyr Gln Gln Gln Gly Arg Leu Asp Lys
 65                  70                  75                  80

Leu Thr Val Thr Ser Gln Asn Leu Gln Leu Glu Asn Leu Arg Met Lys
                     85                  90                  95

Leu Pro Lys Pro Lys Pro Val Ser Lys Met Arg Met Ala Thr Pro Leu
                100                 105                 110

Leu Met Gln Ala Leu Pro Met Gly Ala Leu Pro Gln Gly Pro Met Gln
                115                 120                 125

Asn Ala Thr Lys Tyr Gly Asn Met Thr Glu Asp His Val Met His Leu
                130                 135                 140

Leu Gln Asn Ala Asp Pro Leu Lys Val Tyr Pro Pro Leu Lys Ser Phe
145                 150                 155                 160

Pro Glu Asn Leu Arg His Leu Lys Asn Thr Met Glu Thr Ile Asp Trp
                165                 170                 175

Lys Val Phe Glu Ser Trp Met His His Trp Leu Leu Phe Glu Met Ser
                180                 185                 190

Arg His Ser Leu Glu Gln Lys Pro Thr Asp Ala Pro Pro Lys Glu Ser
                195                 200                 205

Leu Glu Leu Glu Asp Pro Ser Ser Gly Gly Val Thr Lys Gln Asp Leu
                210                 215                 220

Gly Pro Val Pro Met Met Asp Ile Asp Pro Tyr Lys Glu Phe Gly Ala
225                 230                 235                 240

Thr Val Glu Leu Leu Ser Phe Leu Pro Ser Asp Phe Phe Pro Ser Val
                245                 250                 255

Arg Asp Leu Leu Asp Thr Ala Ser Ala Leu Tyr Arg Glu Ala Leu Glu
                260                 265                 270

Ser Pro Glu His Cys Ser Pro His His Thr Ala Leu Arg Gln Ala Ile
                275                 280                 285

Leu Cys Trp Gly Glu Leu Met Thr Leu Ala Thr Trp Val Gly Asn Asn
                290                 295                 300

Leu Glu Asp Pro Ala Ser Arg Asp Leu Val Val Asn Tyr Val Asn Thr
305                 310                 315                 320

Asn Met Gly Leu Lys Ile Arg Gln Leu Leu Trp Phe His Ile Ser Cys
                325                 330                 335

Leu Thr Phe Gly Arg Glu Thr Val Leu Glu Tyr Leu Val Ser Phe Gly
                340                 345                 350

Val Trp Ile Arg Thr Pro Pro Ala Tyr Arg Pro Pro Asn Ala Pro Ile
                355                 360                 365

Leu Ser Thr Leu Pro Glu Thr Thr Val Val Ala Pro Val Lys Gln Thr
                370                 375                 380

Leu Asn Phe Asp Leu Leu Lys Leu Ala Gly Asp Val Glu Ser Asn Pro
385                 390                 395                 400

Gly Pro Met Glu Asn Ile Thr Ser Gly Phe Leu Gly Pro Leu Leu Val
                405                 410                 415

Leu Gln Ala Gly Phe Phe Leu Leu Thr Arg Ile Leu Thr Ile Pro Gln
                420                 425                 430

Ser Leu Asp Ser Trp Trp Thr Ser Leu Asn Phe Leu Gly Gly Ser Pro
                435                 440                 445

Val Cys Leu Gly Gln Asn Ser Gln Ser Pro Thr Ser Asn His Ser Pro
                450                 455                 460

Thr Ser Cys Pro Pro Ile Cys Pro Gly Tyr Arg Trp Met Cys Leu Arg
465                 470                 475                 480
```

```
Arg Phe Ile Ile Phe Leu Phe Ile Leu Leu Leu Cys Leu Ile Phe Leu
                485                 490                 495
Leu Val Leu Leu Asp Tyr Gln Gly Met Leu Pro Val Cys Pro Leu Ile
            500                 505                 510
Pro Gly Ser Thr Thr Asn Thr Gly Pro Cys Lys Thr Cys Thr Thr
        515                 520                 525
Pro Ala Gln Gly Asn Ser Met Phe Pro Ser Cys Cys Cys Thr Lys Pro
        530                 535                 540
Thr Asp Gly Asn Cys Thr Cys Ile Pro Ile Pro Ser Ser Trp Ala Phe
545                 550                 555                 560
Ala Lys Tyr Leu Trp Glu Trp Ala Ser Val Arg Phe Ser Trp Leu Ser
                565                 570                 575
Leu Leu Val Pro Phe Val Gln Trp Phe Val Gly Leu Ser Pro Thr Val
                580                 585                 590
Trp Leu Ser Ala Ile Trp Met Met Trp Tyr Trp Gly Pro Ser Leu Tyr
                595                 600                 605
Ser Ile Val Ser Pro Phe Ile Pro Leu Leu Pro Ile Phe Phe Cys Leu
            610                 615                 620
Trp Val Tyr Ile
625

<210> SEQ ID NO 10
<211> LENGTH: 1998
<212> TYPE: DNA
<213> ORGANISM: Artificial
<220> FEATURE:
<223> OTHER INFORMATION: Synthetic polynucleotide encoding synthetic
      polypeptide hIi-HBc-2A-HBs comprising human invariant
      chain-Hepatitis B core antigen truncate-spacer comprising 2A
      cleavage region of foot and mouth virus-Hepatitis B surface
      antigen

<400> SEQUENCE: 10
atgcacagga ggaggagcag gagctgcagg gaggaccaga agcccgtgat ggacgaccag     60
cgcgacctga tcagcaacaa cgagcagctg ccaatgctgg caggaggcc cggagcaccc    120 gaaagcaagt gcagcagggg cgccctgtac accggcttca gcatcctggt gaccctcctg    180
ctggccggcc aggccaccac cgcctatttc ctgtaccagc agcagggcag gctcgataag    240
ctgaccgtga cctcccagaa cctgcagctg gagaacctga ggatgaagct gcccaagccc    300
cccaagcccg tgagcaagat gaggatggcc accccctgc tgatgcaggc tctgcccatg    360
ggggccctgc cccagggccc catgcagaac gccaccaaat acggcaacat gaccgaggac    420
cacgtgatgc acctgctgca gaacgccgat cctctgaagg tgtacccacc cctgaaaggc    480
agcttccccg agaaccctca ggcacctgaag aacaccatgg agaccatcga ctggaaggtg    540
ttcgagagct ggatgcacca ctggctgctg ttcgagatga ccggcacag cctggagcag    600 aagcccaccg acgcccctcc aaggagagc ctcgagctcg aggacccaag cagcggcctg    660
ggcgtgacca agcaggacct gggccccgtg cccatggaca ttgacccca caaggagttc    720 ggcgccaccg tcgaactgct gagcttcctc cccagcgact tcttcccct cgtgagggat    780 ctgctggaca cagctagcgc cctgtacagg gaggccctgg agagcccga gcactgcagc    840 ccccaccaca cagccctgag gcaggccatc ctctgttggg gcgagctgat gaccctggcc    900
acctgggtgg gcaataacct ggaggacccc gccagcaggg acctggtggt caactacgtg    960
aacaccaaca tgggcctgaa gatcaggcag ctgctgtggt tccacatcag ctgcctgacc   1020
```

```
tttggcaggg agaccgtcct ggagtacctg gtgagcttcg gcgtgtggat caggactccc    1080
ccagcctaca ggccccctaa cgccccatc ctgtctaccc tgcccgagac caccgtggtg     1140
aggaggaggg acaggggcag aagccccagg agaaggaccc ctagccccag gaggaggagg    1200
agccagagcc ccaggaggag gaggagccag agccggagag ccagtgcgc cctgtgaag     1260 cagaccctga acttcgacct gctgaagctg gccggcgacg tggagagcaa tcccggccct    1320
atggaaaaca tcaccagcgg cttcctgggc cccctgctgg tgctgcaggc cggcttcttc    1380
ctgctgacca ggatcctgac cattccccag tcactggaca gctggtggac cagcctgaac    1440
ttcctcggcg ggagccccgt gtgcctgggc cagaatagcc agagcccac cagcaaccac    1500 tctcccactt cctgccccc tatctgcccc ggctacaggt ggatgtgcct gaggaggttc    1560
atcatcttcc tgttcatcct gctgctgtgc ctgatcttcc tgctggtgct gctggactac    1620
cagggaatgc tgcccgtgtg tccctgatc cccggaagca ccaccaa caccggcccc     1680 tgcaagacct gcaccacccc cgcccagggc aactctatgt tccccagctg ctgctgcacc    1740
aagcccaccg acggcaactg cacttgcatt cccatccca gcagctgggc cttcgccaaa    1800
tatctgtggg agtgggccag cgtgaggttt agctggctga gcctgctggt gcccttcgtg    1860
cagtggtttg tgggcctgag ccccaccgtg tggctgagcg ccatctggat gatgtggtac    1920
tggggcccct ccctgtacag catcgtgagc cccttcatcc cctcctgcc catcttcttc    1980 tgcctgtggg tgtacatc                                                  1998
```

<210> SEQ ID NO 11
<211> LENGTH: 185
<212> TYPE: PRT
<213> ORGANISM: Hepatitis B Virus

<400> SEQUENCE: 11

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Asp Arg Gly Arg Ser Pro Arg Arg
145                 150                 155                 160

Arg Thr Pro Ser Pro Arg Arg Arg Ser Gln Ser Pro Arg Arg Arg
                165                 170                 175

Arg Ser Gln Ser Arg Glu Ser Gln Cys
            180                 185
```

<210> SEQ ID NO 12
<211> LENGTH: 231
<212> TYPE: PRT
<213> ORGANISM: Artificial
<220> FEATURE:
<223> OTHER INFORMATION: Synthetic polypeptide of human invariant chain hIi alternative variant

<400> SEQUENCE: 12

```
Met His Arg Arg Arg Ser Arg Ser Cys Arg Glu Asp Gln Lys Pro Val
1               5                   10                  15

Met Asp Asp Gln Arg Asp Leu Ile Ser Asn Asn Glu Gln Leu Pro Met
                20                  25                  30

Leu Gly Arg Arg Pro Gly Ala Pro Glu Ser Lys Cys Ser Arg Gly Ala
            35                  40                  45

Leu Tyr Thr Gly Phe Ser Ile Leu Val Thr Leu Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Ser Gln Asn Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Leu Pro Gln Gly Pro Met
        115                 120                 125

Gln Asn Ala Thr Lys Tyr Gly Asn Met Thr Glu Asp His Val Met His
    130                 135                 140

Leu Leu Gln Asn Ala Asp Pro Leu Lys Val Tyr Pro Pro Leu Lys Gly
145                 150                 155                 160

Ser Phe Pro Glu Asn Leu Arg His Leu Lys Asn Thr Met Glu Thr Ile
                165                 170                 175

Asp Trp Lys Val Phe Glu Ser Trp Met His His Trp Leu Leu Phe Glu
            180                 185                 190

Met Ser Arg His Ser Leu Glu Gln Lys Pro Thr Asp Ala Pro Pro Lys
        195                 200                 205

Glu Ser Leu Glu Leu Glu Asp Pro Ser Ser Gly Leu Gly Val Thr Lys
    210                 215                 220

Gln Asp Leu Gly Pro Val Pro
225                 230
```

<210> SEQ ID NO 13
<211> LENGTH: 693
<212> TYPE: DNA
<213> ORGANISM: Artificial
<220> FEATURE:
<223> OTHER INFORMATION: Synthetic polynucleotide encoding synthetic polypeptide of human invariant chain hIi alternative variant

<400> SEQUENCE: 13

```
atgcacagga ggagaagcag gagctgtcgg gaagatcaga agccagtcat ggatgaccag    60
cgcgacctta tctccaacaa tgagcaactg cccatgctgg gccggcgccc tggggccccg   120
gagagcaagt gcagccgcgg agccctgtac acaggctttt ccatcctggt gactctgctc   180
ctcgctggcc aggccaccac cgcctacttc ctgtaccagc agcagggccg gctggacaaa   240
ctgacagtca cctcccagaa cctgcagctg gagaacctgc gcatgaagct tcccaagcct   300
cccaagcctg tgagcaagat gcgcatggcc acccgctgc tgatgcaggc gctgcccatg   360
ggagccctgc cccaggggcc catgcagaat gccaccaagt atggcaacat gacagaggac   420
```

```
catgtgatgc acctgctcca gaatgctgac cccctgaagg tgtacccgcc actgaagggg      480
agcttcccgg agaacctgag acaccttaag aacaccatgg agaccataga ctggaaggtc      540
tttgagagct ggatgcacca ttggctcctg tttgaaatga gcaggcactc cttggagcaa      600
aagcccactg acgctccacc gaaagagtca ctggaactgg aggacccgtc ttctgggctg      660
ggtgtgacca agcaggatct gggcccagtc ccc                                   693
```

<210> SEQ ID NO 14
<211> LENGTH: 1998
<212> TYPE: DNA
<213> ORGANISM: Artificial
<220> FEATURE:
<223> OTHER INFORMATION: Synthetic polynucleotide encoding synthetic
    polypeptide of variant hIi-HBc-2A-HBs comprising human invariant
    chain-Hepatitis B core antigen truncate-spacer comprising 2A
    cleavage region of foot and mouth virus-Hepatitis B surface
    antigen

<400> SEQUENCE: 14

```
atgcacagga ggagaagcag gagctgtcgg gaagatcaga agccagtcat ggatgaccag       60
cgcgacctta tctccaacaa tgagcaactg cccatgctgg gccggcgccc tggggccccg      120
gagagcaagt gcagccgcgg agccctgtac acaggctttt ccatcctggt gactctgctc      180
ctcgctggcc aggccaccac cgcctacttc ctgtaccagc agcagggccg gctggacaaa      240
ctgacagtca cctcccagaa cctgcagctg agaacctgc gcatgaagct tcccaagcct      300
cccaagcctg tgagcaagat gcgcatggcc accccgctgc tgatgcaggc gctgcccatg      360
ggagccctgc cccaggggcc catgcagaat gccaccaagt atggcaacat gacagaggac      420
catgtgatgc acctgctcca gaatgctgac cccctgaagg tgtacccgcc actgaagggg      480
agcttcccgg agaacctgag acaccttaag aacaccatgg agaccataga ctggaaggtc      540
tttgagagct ggatgcacca ttggctcctg tttgaaatga gcaggcactc cttggagcaa      600
aagcccactg acgctccacc gaaagagtca ctggaactgg aggacccgtc ttctgggctg      660
ggtgtgacca agcaggatct gggcccagtc cccatggaca ttgaccctta taaagaattt      720
ggagctactg tggagttact ctcgtttttg ccttctgact ctttccttc cgtcagagat      780 ctcctagaca ccgcctcagc tctgtatcga aagccttag agtctcctga gcattgctca      840
cctcaccata ctgcactcag gcaagccatt tctgctgggg ggaattgat gactctagct      900 acctgggtgg gtaataattt ggaagatcca gcatccaggg atctagtagt caattatgtt      960
aatactaaca tgggtttaaa gatcaggcaa ctattgtggt ttcatatatc ttgccttact     1020
tttggaagag agactgtact tgaatatttg gtctctttcg gagtgtggat tcgcactcct     1080
ccagcctata accaccaaa tgcccctatc ttatcaacac ttccggaaac tactgttgtt     1140
agacgacggg accgaggcag gtcccctaga agaagaactc cctcgcctcg cagacgcaga     1200
tctcaatcgc cgcgtcgcag aagatctcaa tctcgggaat ctcaatgtgc cctgtgaag     1260 cagaccctga acttcgacct gctgaagctg gccggcgacg tggagagcaa tcccggccct     1320
atggagaaca tcacatcagg attcctagga cccctgctcg tgttacaggc ggggttttc     1380 ttgttgacaa gaatcctcac aataccgcag agtctagact cgtggtggac ttctctcaat     1440
tttctagggg gatcacccgt gtgtcttggc caaaattcgc agtccccaac ctccaatcac     1500
tcaccaacct cctgtcctcc aatttgtcct ggttatcgct ggatgtgtct gcggcgtttt     1560
atcatattcc tcttcatcct gctgctatgc ctcatcttct tattggttct tctggattat     1620
```

-continued

```
caaggtatgt tgcccgtttg tcctctaatt ccaggatcaa caacaaccaa tacgggacca    1680
tgcaaaacct gcacgactcc tgctcaaggc aactctatgt ttccctcatg ttgctgtaca    1740
aaacctacgg atggaaattg cacctgtatt cccatcccat cgtcctgggc tttcgcaaaa    1800
tacctatggg agtgggcctc agtccgtttc tcttggctca gtttactagt gccatttgtt    1860
cagtggttcg tagggctttc ccccactgtt tggctttcag ctatatggat gatgtggtat    1920
tgggggccaa gtctgtacag catcgtgagt ccctttatac cgctgttacc aattttcttt    1980
tgtctctggg tatacatt                                                   1998
```

<210> SEQ ID NO 15
<211> LENGTH: 666
<212> TYPE: PRT
<213> ORGANISM: Artificial
<220> FEATURE:
<223> OTHER INFORMATION: Synthetic polypeptide of variant hIi-HBc-2A-HBs comprising human invariant chain-Hepatitis B core antigen truncate-spacer comprising 2A cleavage region of foot and mouth virus-Hepatitis B surface antigen

<400> SEQUENCE: 15

```
Met His Arg Arg Arg Ser Arg Ser Cys Arg Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Ala Pro Glu Ser Lys Cys Ser Arg Gly Ala
        35                  40                  45

Leu Tyr Thr Gly Phe Ser Ile Leu Val Thr Leu Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Ser Gln Asn Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Leu Pro Gln Gly Pro Met
        115                 120                 125

Gln Asn Ala Thr Lys Tyr Gly Asn Met Thr Glu Asp His Val Met His
    130                 135                 140

Leu Leu Gln Asn Ala Asp Pro Leu Lys Val Tyr Pro Pro Leu Lys Gly
145                 150                 155                 160

Ser Phe Pro Glu Asn Leu Arg His Leu Lys Asn Thr Met Glu Thr Ile
                165                 170                 175

Asp Trp Lys Val Phe Glu Ser Trp Met His His Trp Leu Leu Phe Glu
            180                 185                 190

Met Ser Arg His Ser Leu Glu Gln Lys Pro Thr Asp Ala Pro Pro Lys
        195                 200                 205

Glu Ser Leu Glu Leu Glu Asp Pro Ser Ser Gly Leu Gly Val Thr Lys
    210                 215                 220

Gln Asp Leu Gly Pro Val Pro Met Asp Ile Asp Pro Tyr Lys Glu Phe
225                 230                 235                 240

Gly Ala Thr Val Glu Leu Leu Ser Phe Leu Pro Ser Asp Phe Phe Pro
                245                 250                 255

Ser Val Arg Asp Leu Leu Asp Thr Ala Ser Ala Leu Tyr Arg Glu Ala
            260                 265                 270

Leu Glu Ser Pro Glu His Cys Ser Pro His His Thr Ala Leu Arg Gln
```

-continued

|   |   |   |   | 275 |   |   |   |   | 280 |   |   |   |   | 285 |   |   |   |
|---|---|---|---|---|---|---|---|---|---|---|---|---|---|---|---|---|---|

Ala Ile Leu Cys Trp Gly Glu Leu Met Thr Leu Ala Thr Trp Val Gly
    290                             295                            300

Asn Asn Leu Glu Asp Pro Ala Ser Arg Asp Leu Val Val Asn Tyr Val
305                         310                        315                    320

Asn Thr Asn Met Gly Leu Lys Ile Arg Gln Leu Leu Trp Phe His Ile
            325                    330                   335

Ser Cys Leu Thr Phe Gly Arg Glu Thr Val Leu Glu Tyr Leu Val Ser
         340                  345                350

Phe Gly Val Trp Ile Arg Thr Pro Pro Ala Tyr Arg Pro Pro Asn Ala
        355                 360              365

Pro Ile Leu Ser Thr Leu Pro Glu Thr Thr Val Val Arg Arg Arg Asp
    370                 375              380

Arg Gly Arg Ser Pro Arg Arg Arg Thr Pro Ser Pro Arg Arg Arg Arg
385                 390              395              400

Ser Gln Ser Pro Arg Arg Arg Ser Gln Ser Arg Glu Ser Gln Cys
         405                410              415

Ala Pro Val Lys Gln Thr Leu Asn Phe Asp Leu Leu Lys Leu Ala Gly
         420                425              430

Asp Val Glu Ser Asn Pro Gly Pro Met Glu Asn Ile Thr Ser Gly Phe
        435                 440              445

Leu Gly Pro Leu Leu Val Leu Gln Ala Gly Phe Phe Leu Leu Thr Arg
    450                 455              460

Ile Leu Thr Ile Pro Gln Ser Leu Asp Ser Trp Trp Thr Ser Leu Asn
465                       470                475              480

Phe Leu Gly Gly Ser Pro Val Cys Leu Gly Gln Asn Ser Gln Ser Pro
        485                 490              495

Thr Ser Asn His Ser Pro Thr Ser Cys Pro Pro Ile Cys Pro Gly Tyr
        500               505              510

Arg Trp Met Cys Leu Arg Arg Phe Ile Ile Phe Leu Phe Ile Leu Leu
        515                520              525

Leu Cys Leu Ile Phe Leu Leu Val Leu Leu Asp Tyr Gln Gly Met Leu
    530                 535             540

Pro Val Cys Pro Leu Ile Pro Gly Ser Thr Thr Thr Asn Thr Gly Pro
545                       550                555              560

Cys Lys Thr Cys Thr Thr Pro Ala Gln Gly Asn Ser Met Phe Pro Ser
        565                570              575

Cys Cys Cys Thr Lys Pro Thr Asp Gly Asn Cys Thr Cys Ile Pro Ile
        580                585              590

Pro Ser Ser Trp Ala Phe Ala Lys Tyr Leu Trp Glu Trp Ala Ser Val
    595                 600              605

Arg Phe Ser Trp Leu Ser Leu Leu Val Pro Phe Val Gln Trp Phe Val
    610                 615              620

Gly Leu Ser Pro Thr Val Trp Leu Ser Ala Ile Trp Met Met Trp Tyr
625                 630              635              640

Trp Gly Pro Ser Leu Tyr Ser Ile Val Ser Pro Phe Ile Pro Leu Leu
        645                650              655

Pro Ile Phe Phe Cys Leu Trp Val Tyr Ile
    660                 665

HEPATITIS B IMMUNIZATION REGIMEN AND COMPOSITIONS

CROSS-REFERENCE TO RELATED APPLICATIONS

This application is filed pursuant to 35 U.S.C. § 371 as a United States National Phase Application of International Application No. PCT/EP2018/085086 filed Dec. 14, 2018 which claims priority from UK Application No. 1721069.1 filed Dec. 15, 2017.

SEQUENCE LISTING

A sequence listing filed herewith, entitled "VB66508_Sequence_Listing", prepared Feb. 4, 2021, 36 KB in size, is hereby incorporated by reference herein.

FIELD OF THE INVENTION

The present invention relates to novel compositions which may find use in immunisation regimens for the treatment of chronic hepatitis B.

BACKGROUND TO THE INVENTION

Hepatitis B virus (HBV) infection is a major public health problem. Globally, approximately 257 million people are infected with HBV [WHO, 2017]. The clinical course and outcome of HBV infection is largely driven by the age at infection and a complex interaction between the virus and the host immune response [Ott, 2012; Maini, 2016]. Thus, exposure to HBV may lead to acute hepatitis that resolves spontaneously or may progress to various forms of chronic infection, including the inactive hepatitis B surface antigen (HBsAg) carrier state, chronic hepatitis, cirrhosis and hepatocellular carcinoma (HCC) [Liaw, 2009]. The prevalence of HBsAg in the adult population is >2%, with rates of 5-8% in South East Asia and China and >8% in the African Region. Between 15-40% of persons with chronic hepatitis B infection (defined as serum HBsAg being detected for more than 6 months) will develop liver sequelae, of which liver cirrhosis (LC), hepatic decompensation and HCC are the major complications.

Although implementation of universal prophylactic hepatitis B immunization in infants has been highly effective in reducing the incidence and prevalence of hepatitis B in many endemic countries, it has not yet led to a strong decrease in the prevalence of chronic hepatitis B infection (CHB) in adolescents and adults, and it is not expected to impact on HBV-related deaths until several decades after introduction. In 2015, hepatitis B accounted for 887,000 deaths, mostly from liver cirrhosis and HCC [WHO, 2017].

Clinical management of chronic hepatitis B aims to improve survival and quality of life by preventing disease progression, and consequently HCC development [Liaw, 2013]. Current treatment strategy is mainly based on the long-term suppression of HBV DNA replication to achieve the stabilisation of HBV-induced liver disease and to prevent progression. Serum HBV DNA level is a cornerstone endpoint of all current treatment modalities. Achieving loss of (detectable) hepatitis B e-antigen (HBeAg) is another valuable biomarker, however HBsAg loss, with or without anti-HBs seroconversion, is generally considered an optimal endpoint representing "functional cure", as it indicates profound suppression of HBV replication and viral protein expression [Block, 2017; Cornberg, 2017]. Currently, there are two main treatment options for CHB patients: either by pegylated interferon alpha (PegIFNα) or by nucleo(s)tide analogues (NA) [EASL, 2017]. PegIFNα aiming at induction of a long-term immune control with a finite duration treatment may achieve sustained off-treatment control, but durable virological response and hepatitis B surface antigen (HBsAg) loss is limited to a small proportion of patients. In addition, owing to its poor tolerability and long-term safety concerns, a significant number of patients are ineligible for this type of treatment.

NAs act by suppressing DNA replication through inhibition of HBV polymerase reverse transcriptase activity. The NAs approved in Europe for HBV treatment include entecavir (ETV), tenofovir disoproxil fumarate (TDF) and tenofovir alafenamide (TAF) that are associated with high barrier against HBV resistance as well as lamivudine (LAM), adefovir dipivoxil (ADV) and telbivudine (TBV) that are associated with low barrier to HBV resistance. The main advantage of treatment with a potent NA with high barrier to resistance is its predictable high long-term antiviral efficacy leading to HBV DNA suppression in the vast majority of compliant patients as well as its favourable safety profile. The disadvantage of NA treatment is its long-term therapeutic regimen, because a NA does not usually achieve HBV eradication and NA discontinuation may lead to HBV relapse [Kranidioti, 2015]. HBsAg loss representing a functional cure is now the gold standard treatment endpoint in CHB [Block, 2017; Cornberg, 2017], which however, is rarely achieved with NA treatment [Zoutendijk, 2011].

Because of a low rate of HBsAg seroclearance [Zoutendijk, 2011] and a high risk of off-NA viral relapse [Kranidioti, 2015], most patients are maintained under long-term or even indefinite NA therapy, which could be associated with reduction in patient compliance to therapy, increase in financial costs and increased risk for drug toxicity and drug resistance mutations upon long-term exposure [Terrault, 2015]. A new strategy is therefore necessary to supplement to the NA therapy to achieve "functional cure" with a finite regimen.

New treatment strategies currently being explored include new antiviral strategies as well as novel immunotherapeutic strategies that boost HBV-specific adaptive immune response or activate innate intrahepatic immunity [Durantel, 2016]. So far, none of these experimental treatments have been shown to be efficacious. Among the vaccination strategies evaluated, none was able to induce a robust polyfunctional CD8$^+$ T-cell response to HBV core antigen (HBcAg) that is of key importance to restore immune control on the virus [Lau, 2002; Li, 2011; Liang, 2011; Bertoletti, 2012; Boni, 2012]. Early efforts on recombinant vaccines based on HBV surface and/or PreS antigens preliminarily induced antibody responses but no HBV-specific CD8+ T-cell response, with no clinical or virological benefit [Jung, 2002; Vandepapelière, 2007]. A DNA vaccine expressing HBV envelope failed to restore T cell response specific to HBsAg and HBcAg thus did not decrease the risk of relapse in patients after NA discontinuation [Fontaine, 2015]. With new delivery systems, a DNA vaccine (prime vaccine) and MVA viral vector vaccine (boost vaccine) encoding S, preS1/S2 showed no T cell induction or reduction in viremia suggesting HBV PreS and surface antigens alone are not sufficient to cure patients [Cavenaugh, 2011]. More recently, vaccine strategies targeting multiple HBV antigens and new delivery systems have been investigated. A recombinant HBsAg/HBcAg vaccine led to a viral load decrease to a very low level (i.e. ~50 IU/ml) in only half of the patients [Al-Mahtab, 2013]. A DNA vaccine encoding S, preS1/S2, core, polymerase and X proteins with genetically adjuvanted IL-12 together with lamivudine induced a multi-specific T cell response and a >2 log 10 decrease in viral load in half of the patients. However, changes in quantitative detection of HBsAg, loss of HBsAg or HBsAg seroconversion were not observed in any patients [Yang, 2012]. The GS-4774 vaccine, a yeast-based T cell vaccine expressing large S, core and X proteins of HBV did not provide significant reduction in HBsAg in virally-suppressed CHB patients [Lok, 2016].

There remains an unmet need for a treatment which can clear HBsAg in order to allow patients to safely discontinue NA therapy without virological or clinical relapse.

SUMMARY OF THE INVENTION

There is provided an immunogenic composition comprising a replication-defective chimpanzee adenoviral (ChAd) vector comprising a polynucleotide encoding a hepatitis B surface antigen (HBs), a nucleic acid encoding a hepatitis B virus core antigen (HBc) and a nucleic acid encoding the human invariant chain (hIi) fused to the HBc. The composition may find use in a method for treating chronic hepatitis B by administration of the composition in a prime-boost regimen with at least one other immunogenic composition.

In a further aspect, there is provided an immunogenic composition comprising a Modified Vaccinia Virus Ankara (MVA) vector comprising a polynucleotide encoding a hepatitis B surface antigen (HBs) and a nucleic acid encoding a hepatitis B virus core antigen (HBc). The composition may find use in a method for treating chronic hepatitis B by administration of the composition in a prime-boost regimen with at least one other immunogenic composition.

In a further aspect, there is provided an immunogenic composition comprising a recombinant hepatitis B surface antigen (HBs), a C-terminal truncated recombinant hepatitis B virus core antigen (HBc) and an adjuvant containing MPL (3D Monophosphoryl lipid A) and QS-21 (a triterpene glycoside purified from the bark of *Quillaja sapnoaria*). The composition may find use in a method for treating chronic hepatitis B by administration of the composition in a prime-boost regimen with at least one other immunogenic composition.

In a further aspect, there is provided an immunogenic combination comprising:
a) a composition comprising a replication-defective chimpanzee adenoviral (ChAd) vector comprising a polynucleotide encoding a hepatitis B surface antigen (HBs) and a nucleic acid encoding a hepatitis B virus core antigen (HBc);
b) a composition comprising a Modified Vaccinia Virus Ankara (MVA) vector comprising a polynucleotide encoding a hepatitis B surface antigen (HBs) and a nucleic acid encoding a hepatitis B virus core antigen (HBc); and
c) a composition comprising a recombinant hepatitis B surface antigen (HBs), recombinant hepatitis B virus core antigen (HBc) and an adjuvant.

The immunogenic combination may find use in a method for treating chronic hepatitis B (CBH) by administration of the compositions in a prime-boost regimen.

The immunogenic combination may find use in a method for treating CHB in a human by administration of the compositions sequentially or concomitantly.

DESCRIPTION OF DRAWINGS/FIGURES

Figure 1B:
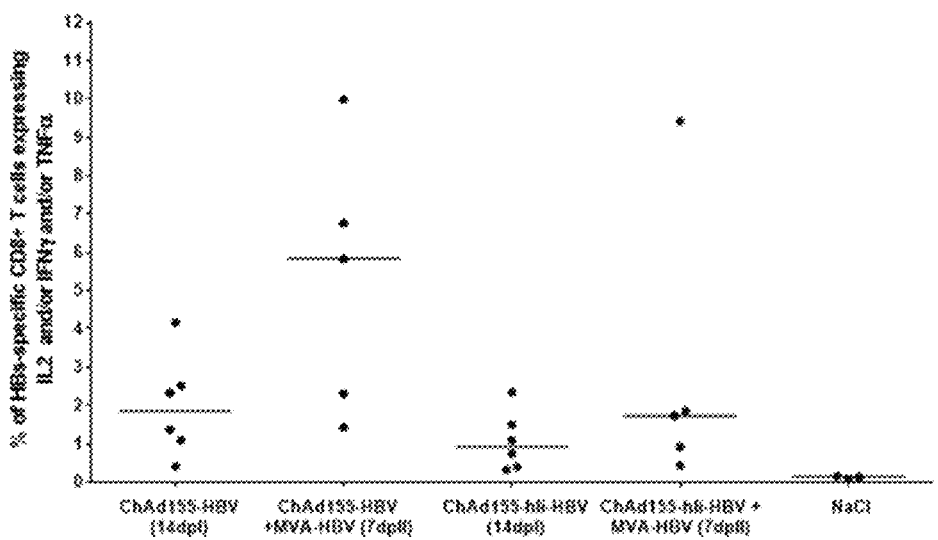

FIG. 1a and FIG. 1B—HBc-specific (A) and HBs-specific (B) CD8$^+$ T-cell responses 14 days after primary immunization with ChAd155-HBV (with and without hIi) and 7 days after MVA-HBV booster immunization (individual animals with medians are represented).

Figure 2:
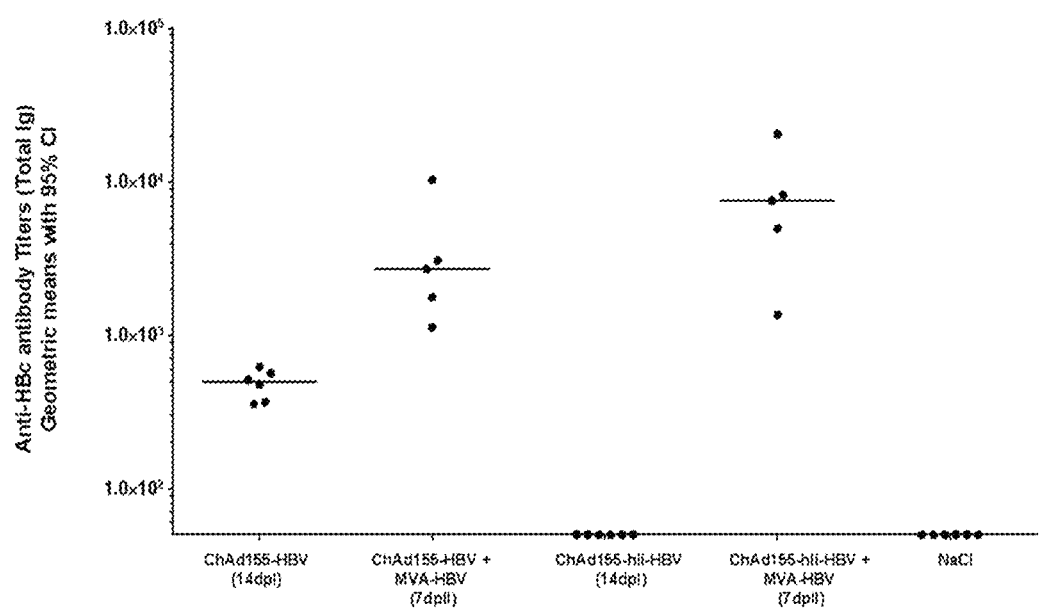

FIG. 2—HBc-specific antibody responses 14 days after primary immunization with ChAd155-HBV (with and without hIi) and 7 days after MVA-HBV booster immunization (individual animals with geomean titers (GMT) are represented).

Figure 3A:
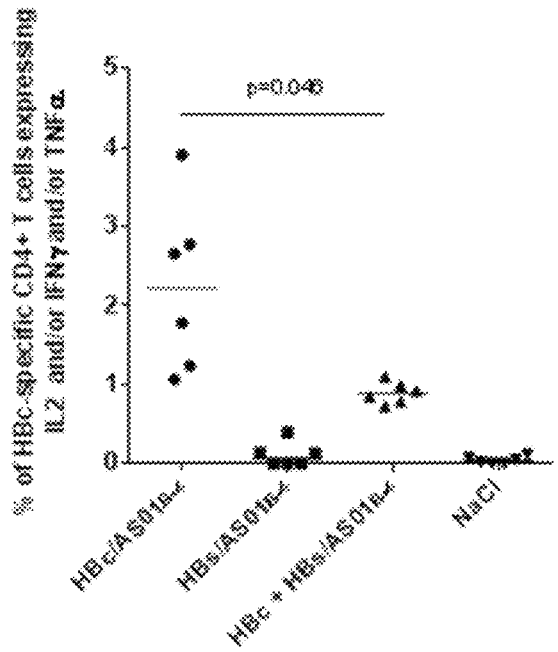
Figure 3B:
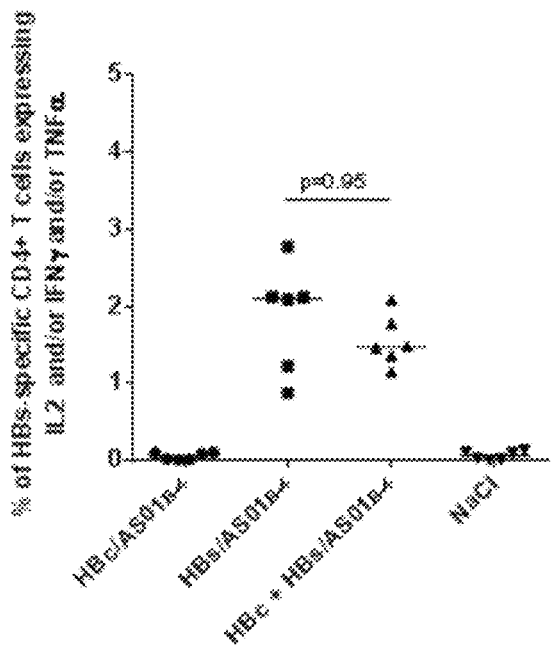

FIG. 3A abd FIG. 3B—HBc and HBs-specific CD4$^+$ T-cell responses at 7 days post-third dose of NaCl, HBc, HBs or HBc-HBs formulated in 50 μl of AS01$_{B-4}$ (pools of 5 animals/group with medians are represented)

Figure 4:
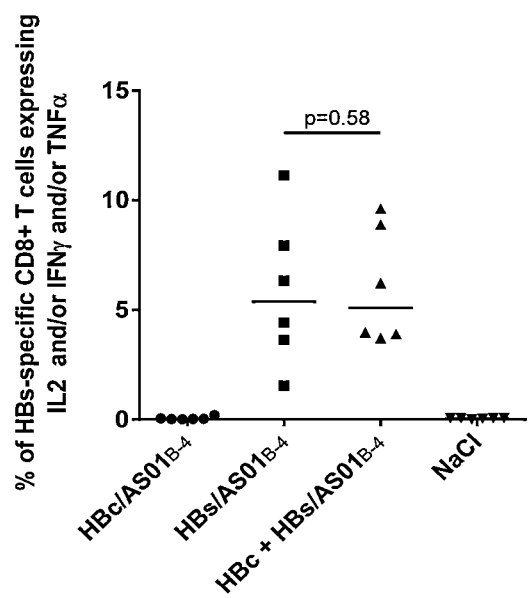

FIG. 4—HBs specific CD8$^+$ T-cell response at 7 days post-third dose of NaCl. HBc, HBs or HBc-HBs formulated in 50 μl of AS01$_{B-4}$ (pools of 5 animals/group with medians are represented).

Figure 5A:
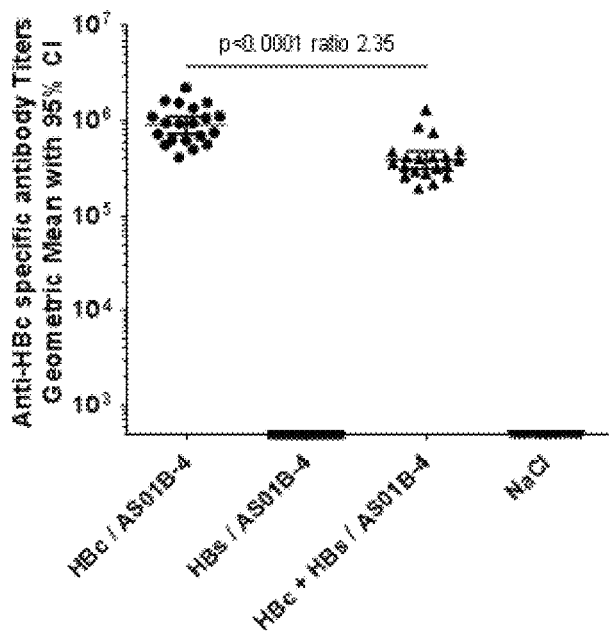
Figure 5B:
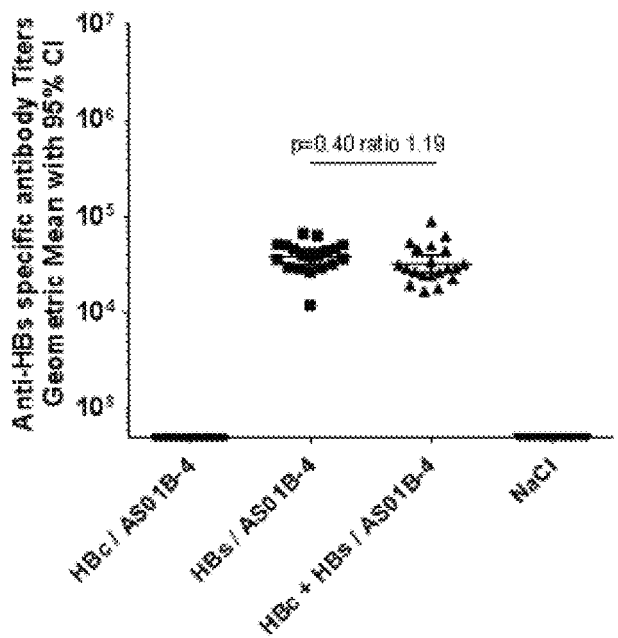

FIG. 5A and FIG. 5B—Anti-HBc and anti-HBs antibody responses at 14 days post-third dose of NaCl, HBc, HBs or HBc-HBs formulated in 50 μl of AS01$_{B-4}$ (individual animals with geomeans and 95% CI are represented).

Figure 6A:
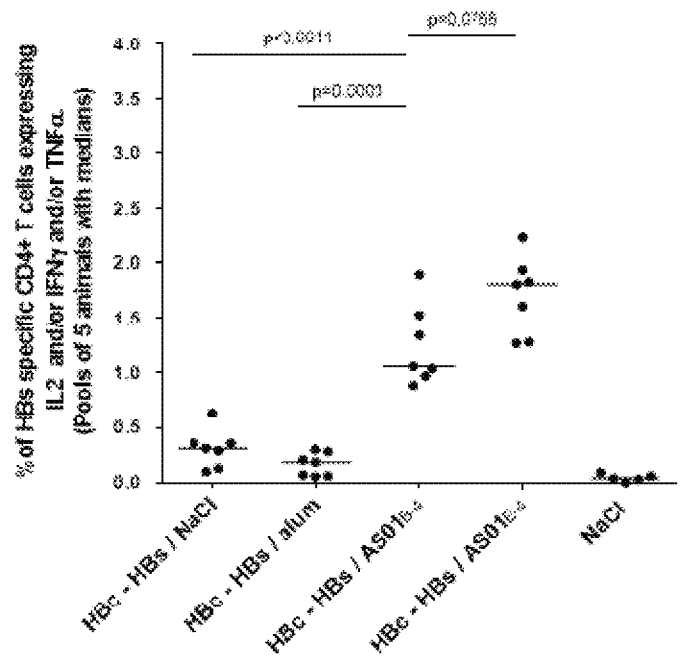
Figure 6B:
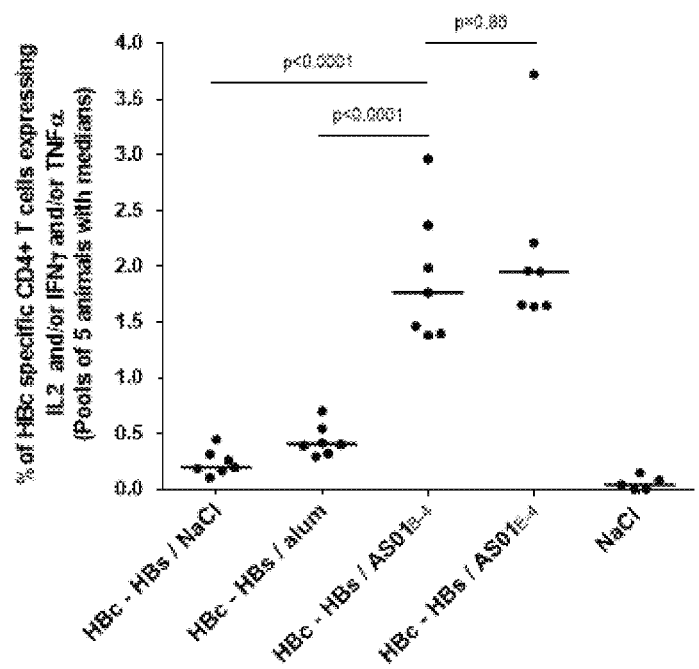
Figure 6C:
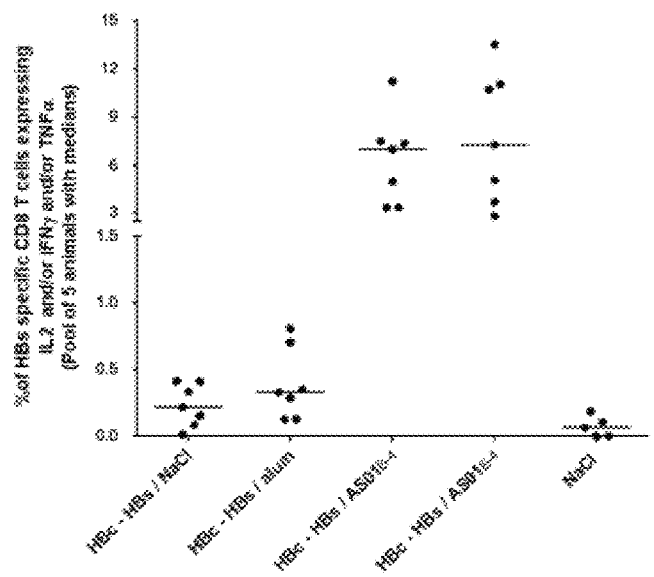

FIG. 6A, FIG. 6B and FIG. 6C—HBs—(A) and HBc—(B) specific CD4+ and HBs-specific CD8+(C) T-cell responses at 7 days post-third dose of NaCl, HBc-HBs, HBc-HBs plus alum, HBc-HBs plus AS01$_{B-4}$ or HBc-HBs plus ASO1$_{E-4}$ (pools of 5 animals/group with medians are represented).

Figure 7A:
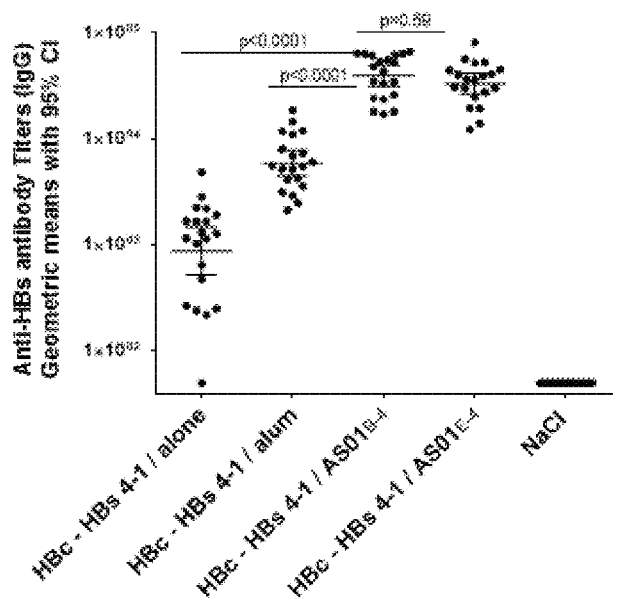
Figure 7B:
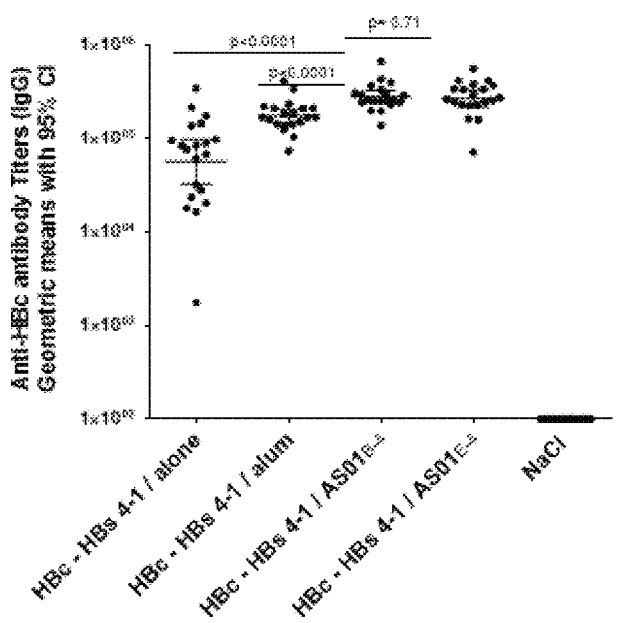

FIG. 7A and FIG. 7B—HBs—(A) and HBc—(B) specific antibody responses at 14 days post-third dose of NaCl, HBc-HBs, HBc-HBs plus alum, HBc-HBs plus AS01$_{B-4}$ or HBc-HBs plus AS01$_{E-4}$ (individual animals with geomeans and 95% CI are represented)

Figure 8A:
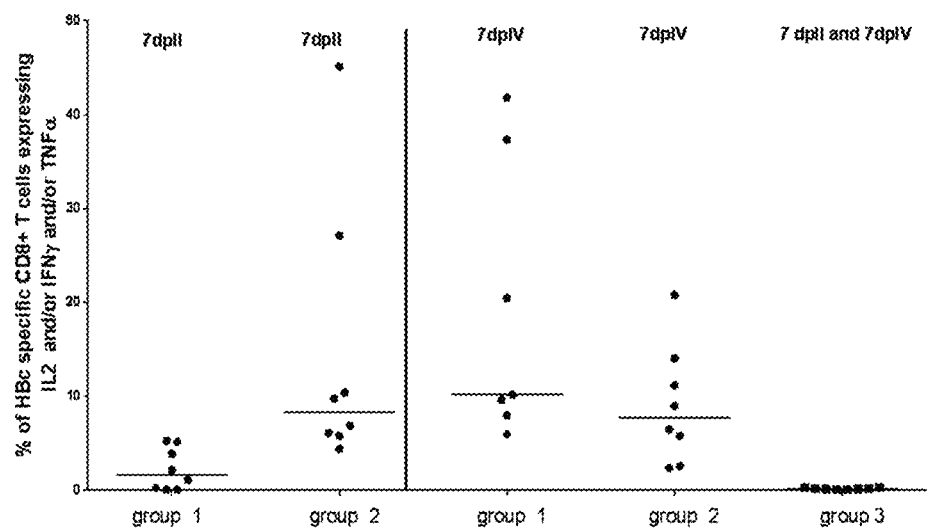
Figure 8B:
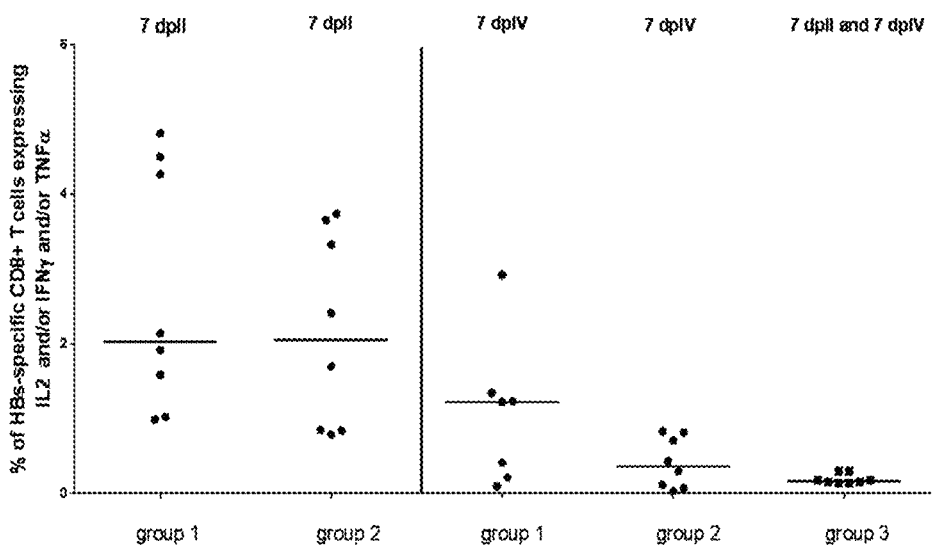

FIG. 8A and FIG 8b—HBc-(A) and HBs-(B) specific CD8$^+$ T-cell responses at 7 days post-second and fourth dose of NaCl, heterologous vector prime-boost with subsequent recombinant proteins or heterologous vector prime-boost with concomitant recombinant proteins (individual animals with medians). Group 1: mice immunized on Day 0 with $10^8$ vp ChAd155-hIi-HBV, on Day 28 with 107 pfu MVA-HBV, on Day 42 and 56 with HBc-HBs 4-1/AS01$_{B-4}$. At 7dpIV one data point is missing due to a technical issue. Group 2: mice immunized on Day 0 with $10^8$ vp ChAd155-hIi-HBV +HBc-HBs 4-1/AS01$_{B-4}$, on Day 28, 42 and 56 with 107 pfu MVA-HBV+HBc-HBs 4-1/AS01$_{B-4}$. Group 3: mice injected on Day 0, 28, 42 and 56 with NaCl.

Figure 9A:
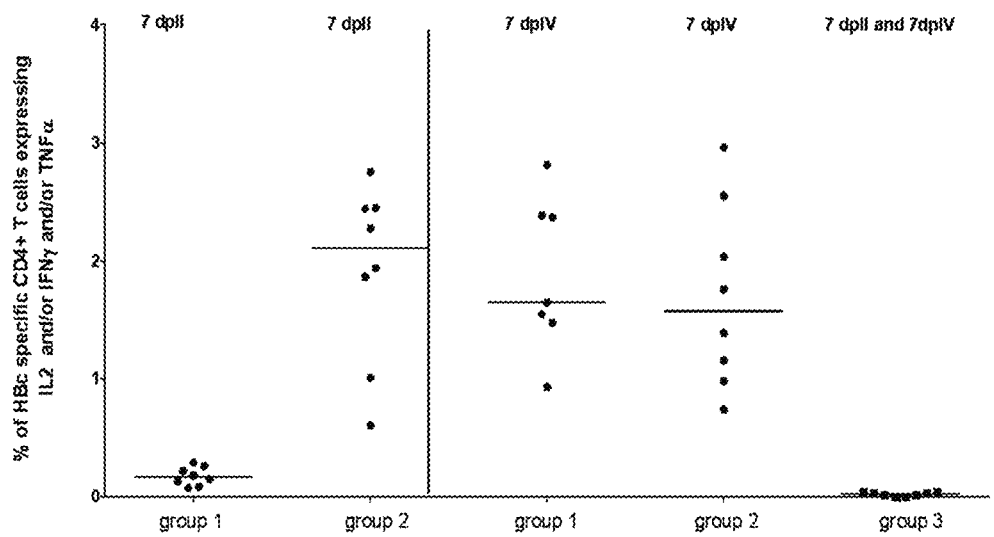
Figure 9B:
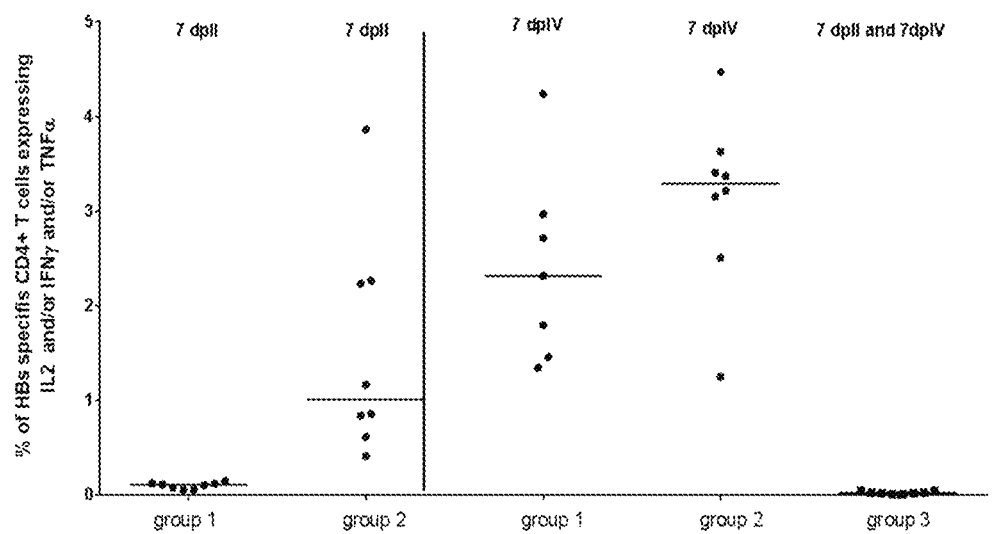

FIG. 9A and FIG. 9B—HBc-(A) or HBs-(B) specific CD4$^+$ T-cell responses at 7 days post-second and fourth dose of NaCl, heterologous vector prime-boost with subsequent recombinant proteins or heterologous vector prime-boost with concomitant recombinant proteins (individual animals with medians). Group 1: mice immunized on Day 0 with 108 vp ChAd155-hIi-HBV, on Day 28 with $10^7$ pfu MVA-HBV, on Day 42 and 56 with HBc-HBs 4-1/AS01$_{B-4}$. At 7dpIV one data point is missing due to a technical issue. Group 2: mice immunized on Day 0 with $10^8$ vp ChAd155-hIi-HBV +HBc-HBs 4-1/AS01$_{B-4}$, on Day 28, 42 and 56 with 107 pfu MVA-HBV+HBc-HBs 4-1/AS01$_{B-4}$.Group 3: mice injected on Day 0, 28, 42 and 56 with NaCl FIG. 10A and FIG. 10B—HBc- and HBs-specific CD4$^+$ (A) and CD8$^+$ (B) T-cells in liver infiltrating lymphocytes 7 days post-fourth dose of NaCl, heterologous vector prime-boost with subsequent recombinant proteins or heterologous vector prime-boost with concomitant recombinant proteins (pools of 3 or 4 animals with medians). Group 1: mice immunized on Day 0 with $10^8$ vp ChAd 155-hIi-HBV, on Day 28 with $10^7$ pfu MVA-HBV, on Day 42 and 56 with HBc-HBs 4-1/AS01$_{B-4}$. At 7dpIV one data point is missing due to a technical issue. Group 2: mice immunized on Day 0 with 10^8 vp ChAd155-hIi-HBV +HBc-HBs 4-1/AS01$_{B-4}$, on Day 28, 42 and 56 with 107 pfu MVA-HBV+HBC-HBs 4-1/AS01$_{B-4}$. Group 3: mice injected on Day 0, 28, 42 and 56 with NaCl.

Figure 11A:
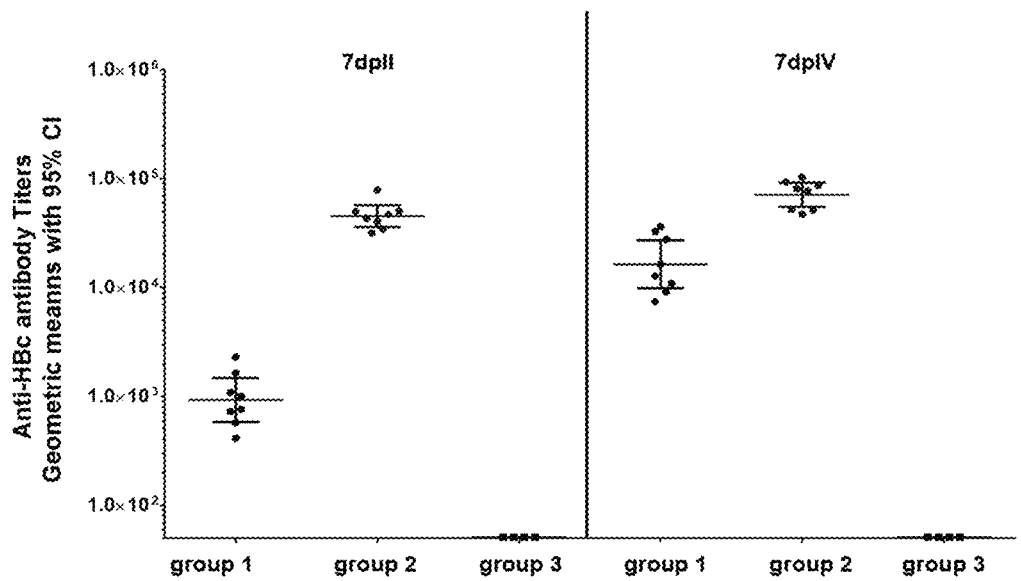
Figure 11B:
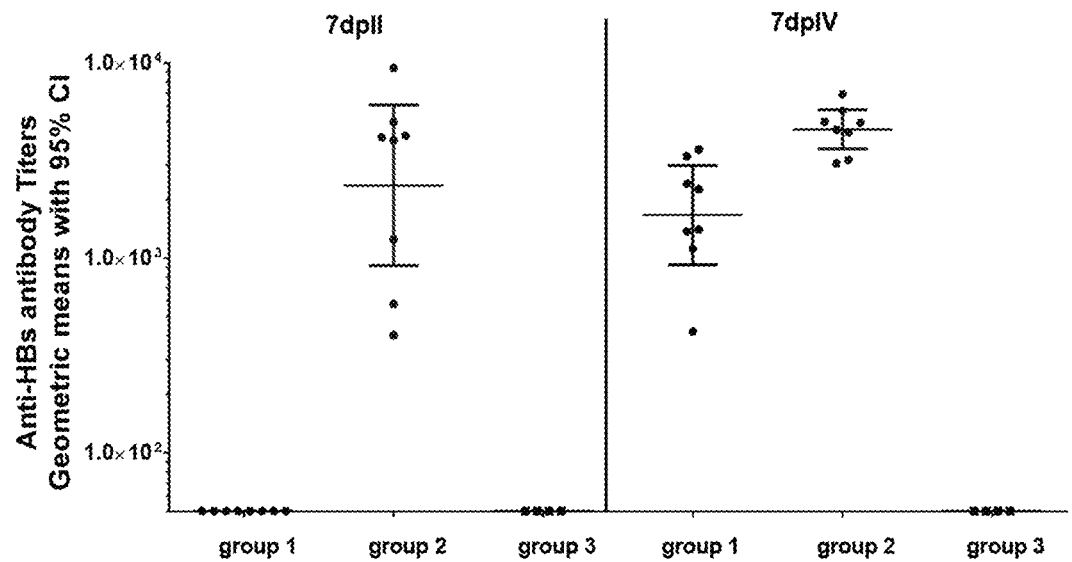

FIG. 11A and FIG. 11B—HBc-specific (A) and HBs-specific (B) antibody response after prime boost vaccine regimens (individual animals with geomeans are represented). Group 1: mice immunized on Day 0 with 10^8 vp ChAd155-hIi-HBV, on Day 28 with 107 pfu MVA-HBV, on Day 42 and 56 with HBc-HBs 4-1/AS01$_{B-4}$. Group 2: mice immunized on Day 0 with 108 vp ChAd155-hIi-HBV +HBc/HBs 4-1/AS01$_{B-4}$, on Day 28, 42 and 56 with 107 pfu MVA-HBV+HBc-HBs 4-1/AS01$_{b-4}$. Group 3: mice injected on Day 0, 28, 42 and 56 with NaCl.

Figure 12:
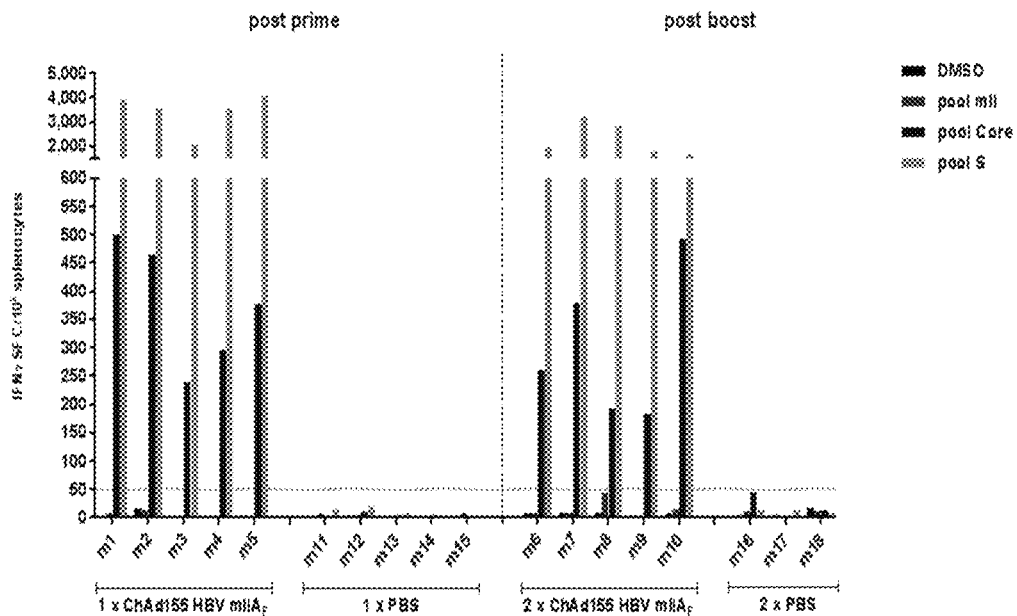

FIG. 12—mIi-, HBc- and HBs-specific IFNγ ELISpot responses, 2 weeks post-first and second injections of PBS or ChAd155-mIi-HBV vector (10^9 vp). mIi-, HBc- and HBs-specific IFN-γ ELISpot responses elicited by 2 administrations of ChAd155-mIi-HBV (10^9 vp) in CB6F1 mice, 2 weeks post-first and second injections (5 animals/group/time-points). The dotted line is the cut-off of the assay.

Figure 13:
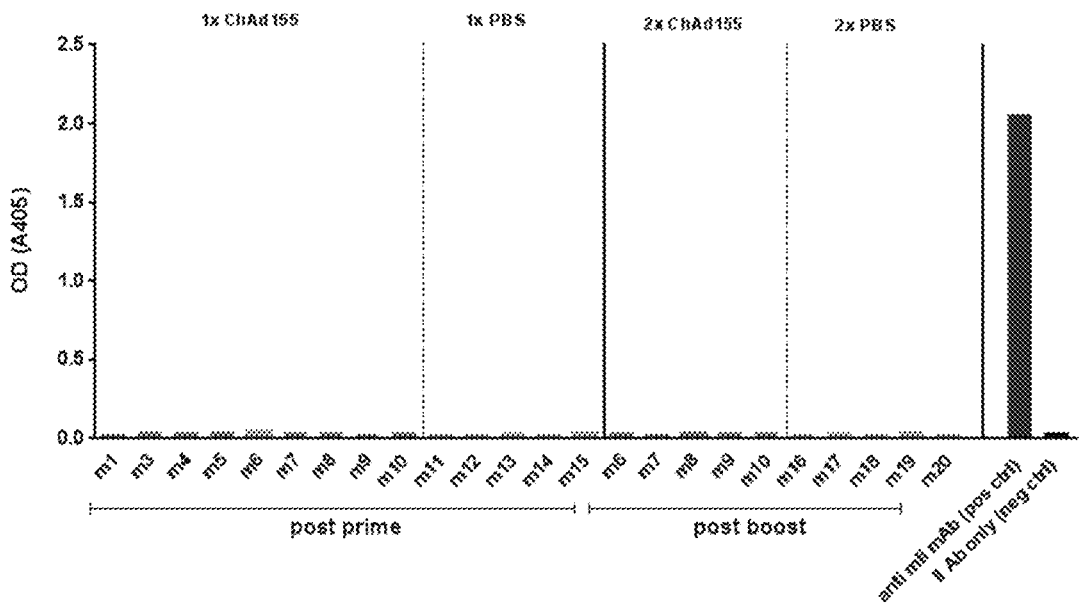

FIG. 13—Anti-mIi antibody responses (ELISA) elicited by 2 administrations of ChAd155-mIi-HBV (10^9vp) in CB6F1 mice, 2 weeks post-first and second injections. Anti-mIi antibody responses (ELISA) elicited by 2 administrations of ChAd155-mIi-HBV (10^9vp) in CB6F1 mice, 2 weeks post-first and second injections (10 animals post-first and 5 animals post-second injection are represented).

Figure 14A:
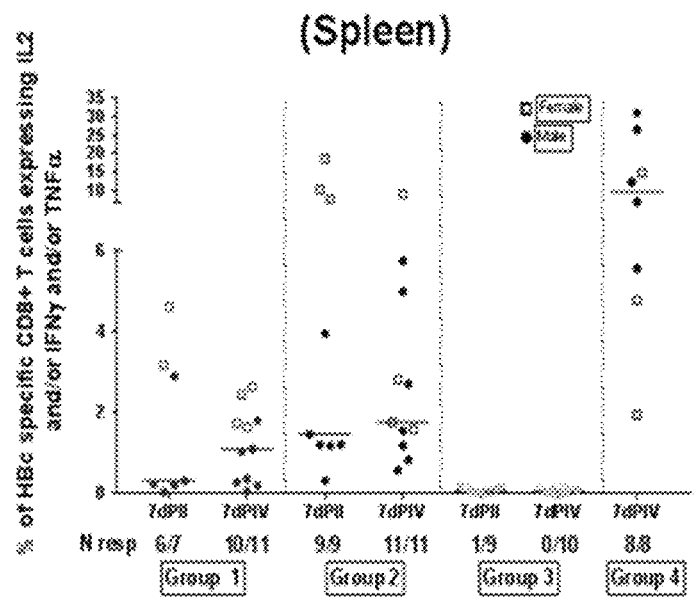
Figure 14B:
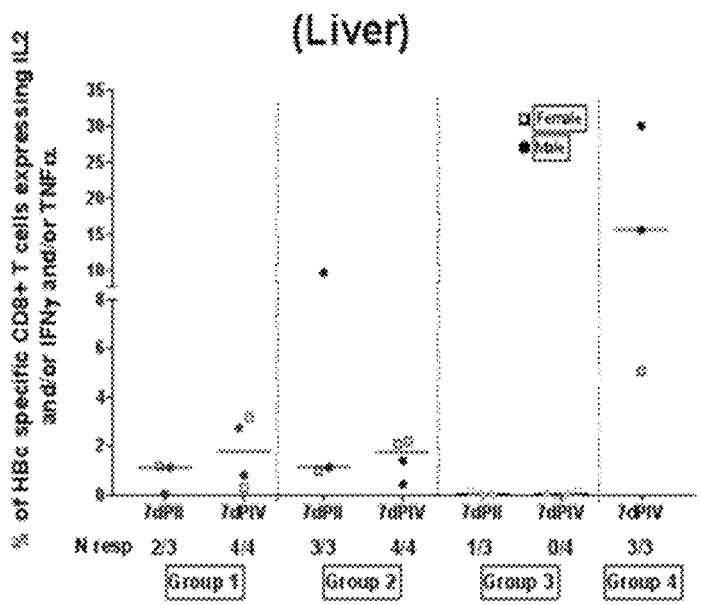

FIG. 14A and FIG. 14B—HBc-specific spleen (A) or liver (B) CD8+ T cells at 7 days post-second dose and 7 days post-fourth dose of NaCl, heterologous vector prime-boost with subsequent recombinant proteins or heterologous vector prime-boost with concomitant recombinant proteins (individual animals with medians).

Figure 15A:
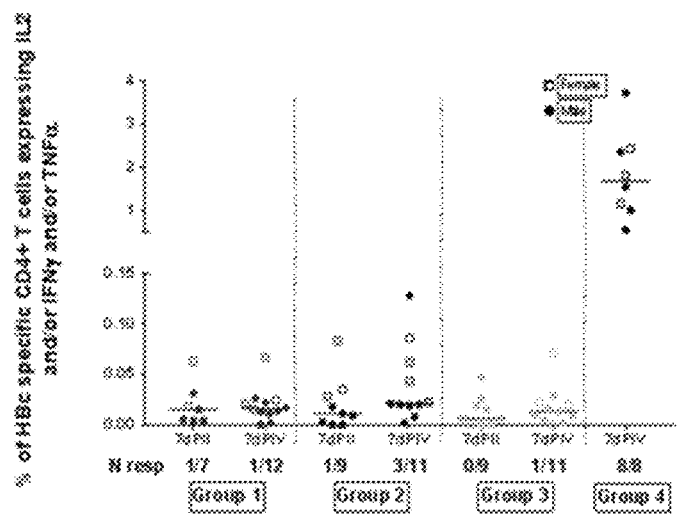
Figure 15B:
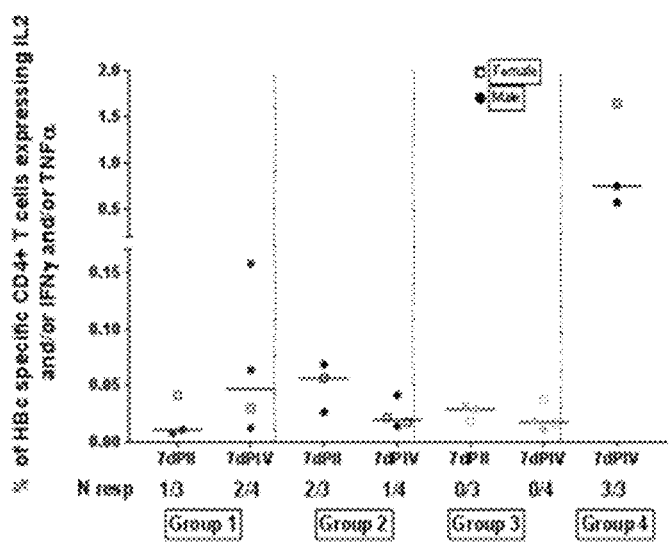

FIG. 15A and FIG. 15B—HBc-specific spleen (A) or liver (B) CD4+ T cells at 7 days post-second dose and 7 days post-fourth dose of NaCl, heterologous vector prime-boost with subsequent recombinant proteins or heterologous vector prime-boost with concomitant recombinant proteins (individual animals with medians).

Figure 16A:
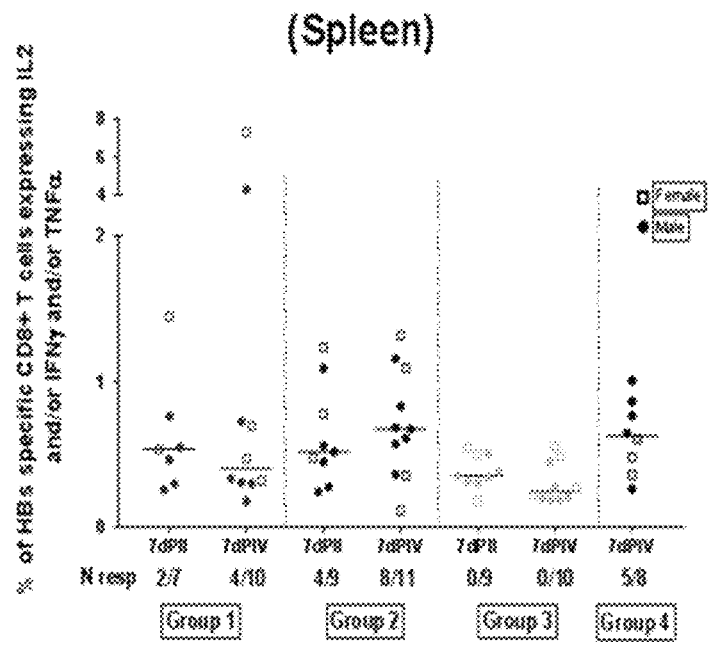
Figure 16B:
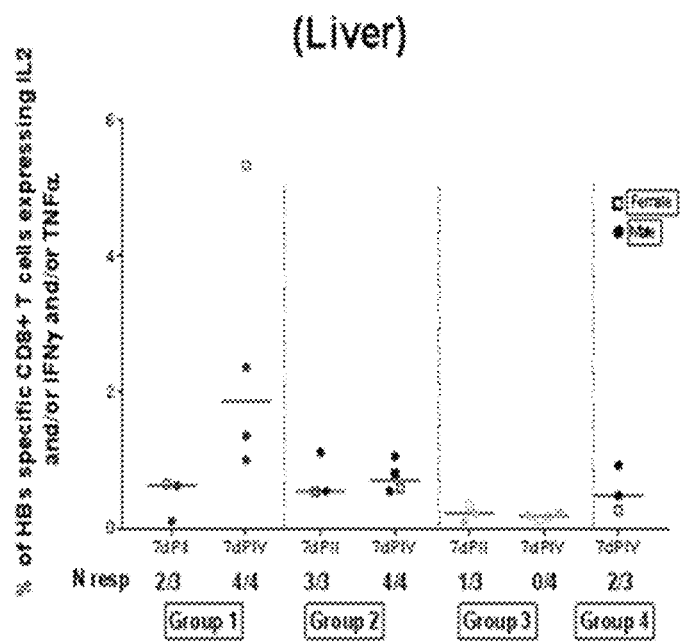

FIG. 16A and FIG. 16B—HBs-specific spleen (A) or liver (B) CD8+ T cells at 7 days post-second dose and 7 days post-fourth dose of NaCl, heterologous vector prime-boost with subsequent recombinant proteins or heterologous vector prime-boost with concomitant recombinant proteins (individual animals with medians).

Figure 17A:
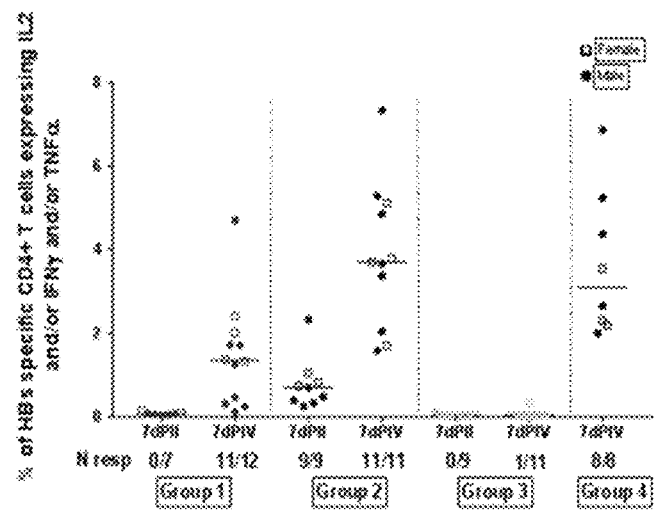
Figure 17B:
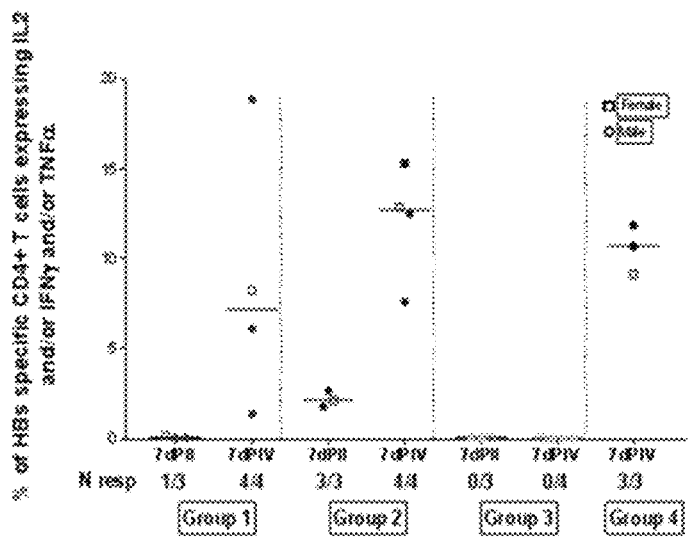

FIG. 17A and FIG17B—HBs-specific spleen (A) or liver (B) CD4+ T cells at 7 days post-second dose and 7 days post-fourth dose of NaCl, heterologous vector prime-boost with subsequent recombinant proteins or heterologous vector prime-boost with concomitant recombinant proteins (individual animals with medians).

Figure 18A:
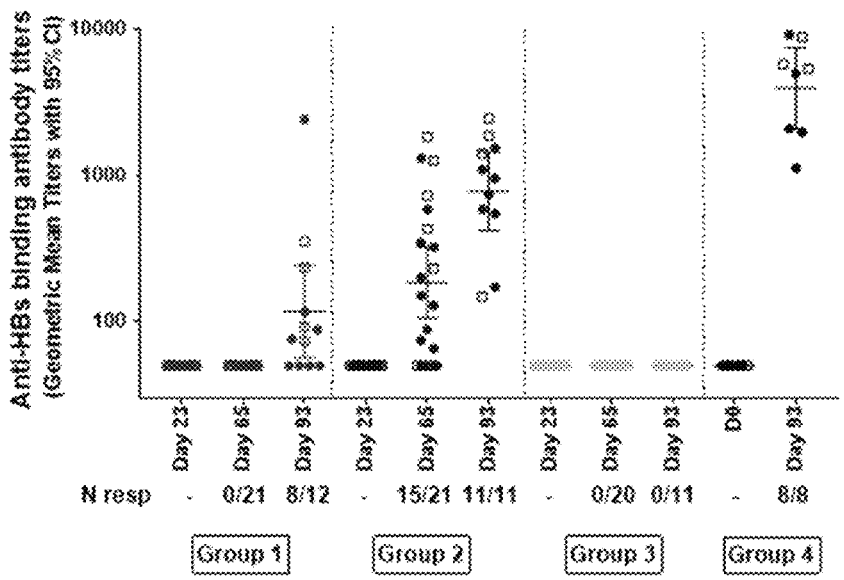
Figure 18B:
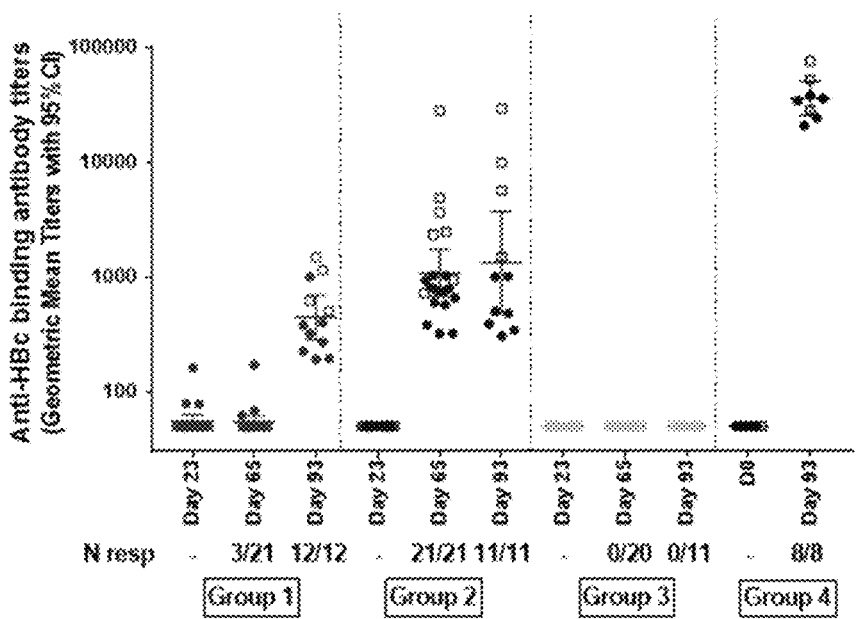

FIG. 18A and FIG. 18B—Anti-HBs (A) and anti-HBc (B) binding antibody responses at Days 23, 65 and 93 (pre-dosing, 7 days post-second dose and 7 days post-fourth dose of NaCl, heterologous vector prime-boost with subsequent recombinant proteins or heterologous vector prime-boost with concomitant recombinant proteins).

Figure 19A:
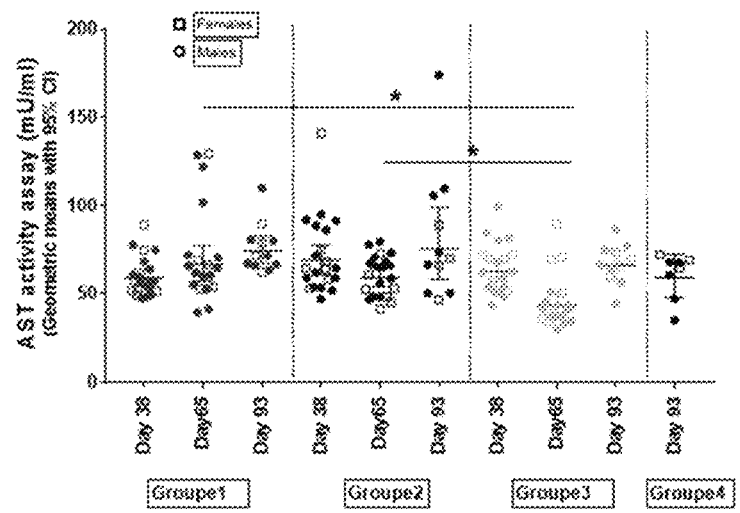
Figure 19B:
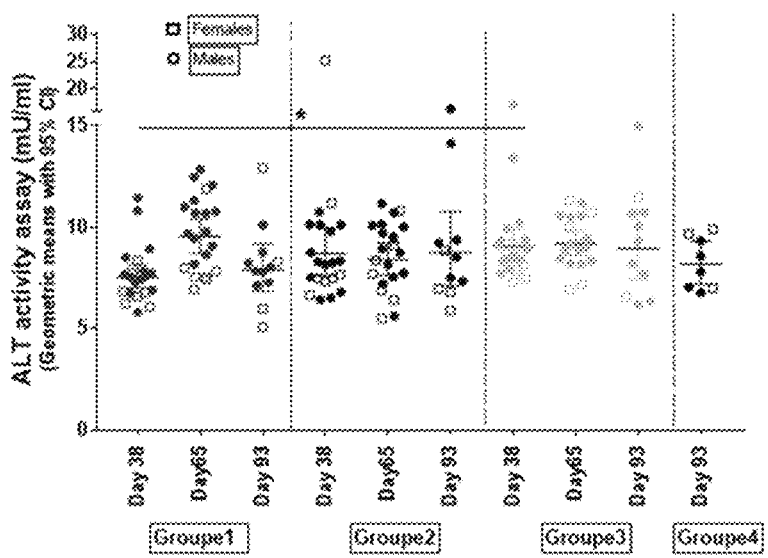

FIG. 19A and FIG. 19B—AST (A) and ALT (B) levels measured in sera from mice (groups 1, 2, 3 and 4) at Days 38, 65, and/or 93 (7 days post-first, second and post-fourth dose of NaCl, heterologous vector prime-boost with subsequent recombinant proteins or heterologous vector prime-boost with concomitant recombinant proteins groups 1, 2, 3) or at day 93 (group 4). At Days 38 and 65, ALT and AST levels were measured in 21 animals/groups and at Day 93, in 12 animals from Group 1, 11 animals from Groups 2 and 3 and 8 animals from Group 4. * represents statistical significance.

Figure 20:
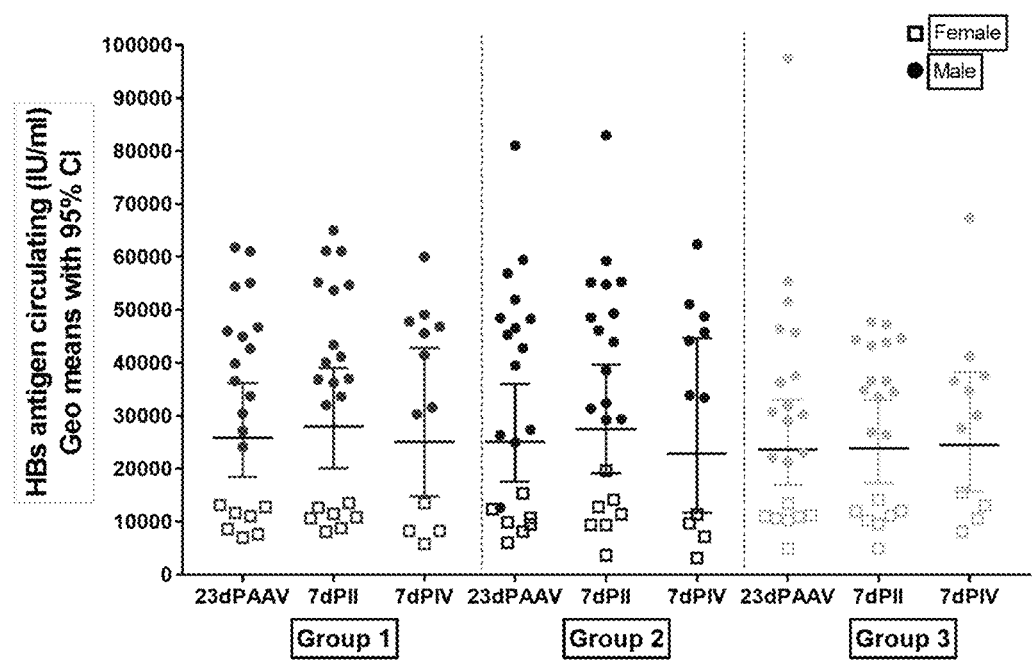

FIG. 20—HBs antigen levels in sera from AAV2/8-HBV injected mice pre-dosing, 7 days post-second dose and 7 days post-fourth dose of NaCl, heterologous vector prime-boost with subsequent recombinant proteins or heterologous vector prime-boost with concomitant recombinant proteins.

Figure 21:
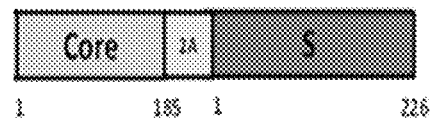

FIG. 21—Structure of HBc-2A-HBs vector insert construct.

Figure 22:
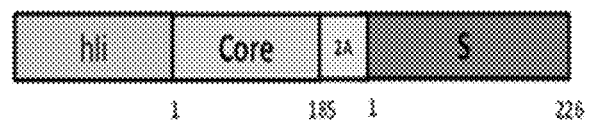

FIG. 22—Structure of hIi-HBc-2A-HBs vector insert construct.

Figure 23A:
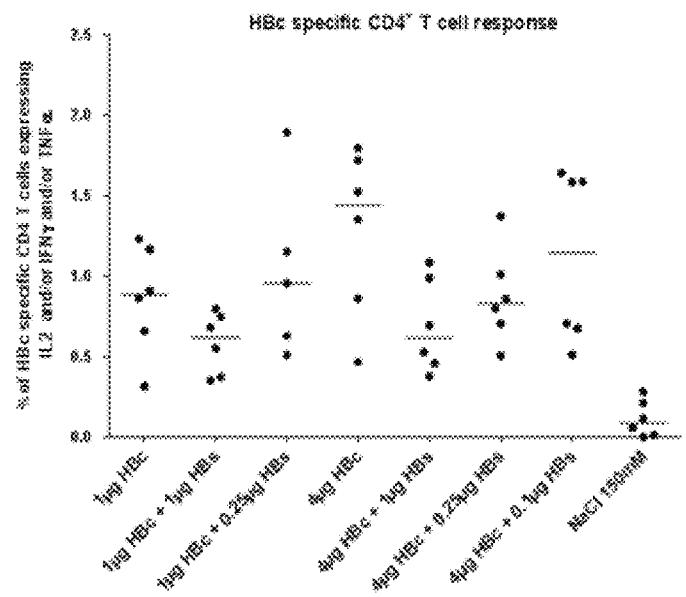
Figure 23B:
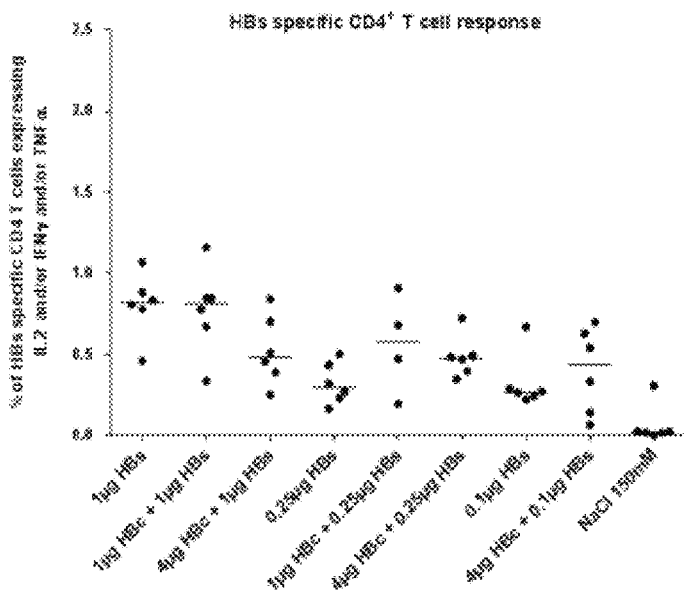

FIG. 23A and FIG 23B—Frequency of HBc- and HBs-specific CD4+ T-cells in the leukocytes of CB6F1 mice 7 days after the 2nd immunization with adjuvanted HBc, HBs and HBc/HBs in various ratios.

Figure 24A:
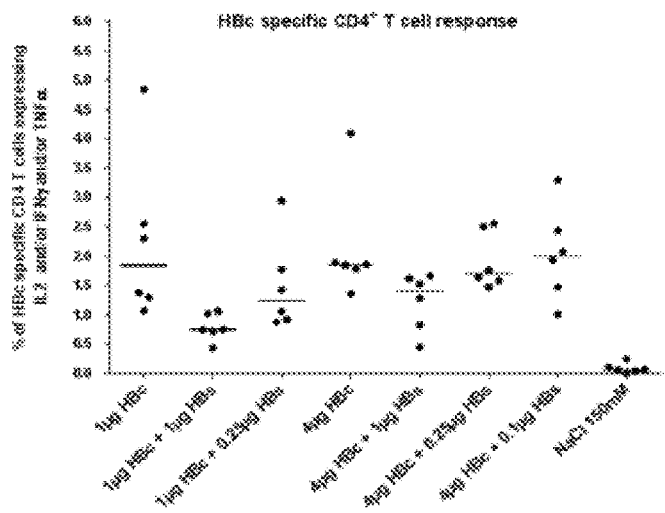
Figure 24B:
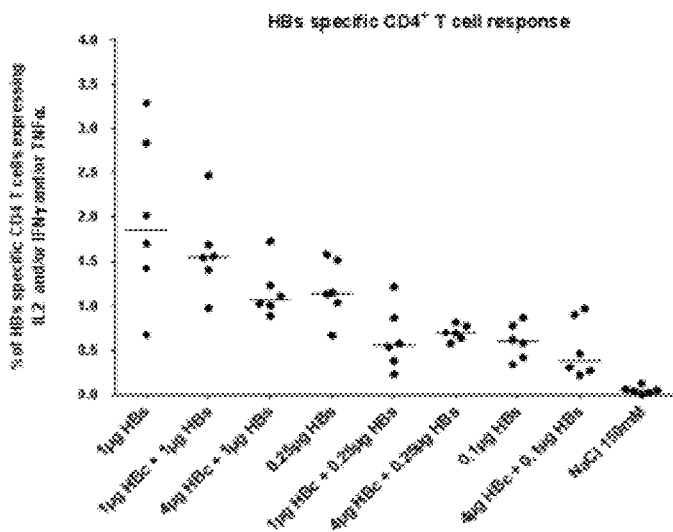

FIG. 24A and FIG. 24B—Frequency of HBc- and HBs-specific CD4+ T-cells in the leukocytes of CB6F1 mice 7 days after the 3rd immunization with adjuvanted HBc, HBs and HBc/HBs in various ratios.

Figure 25A:
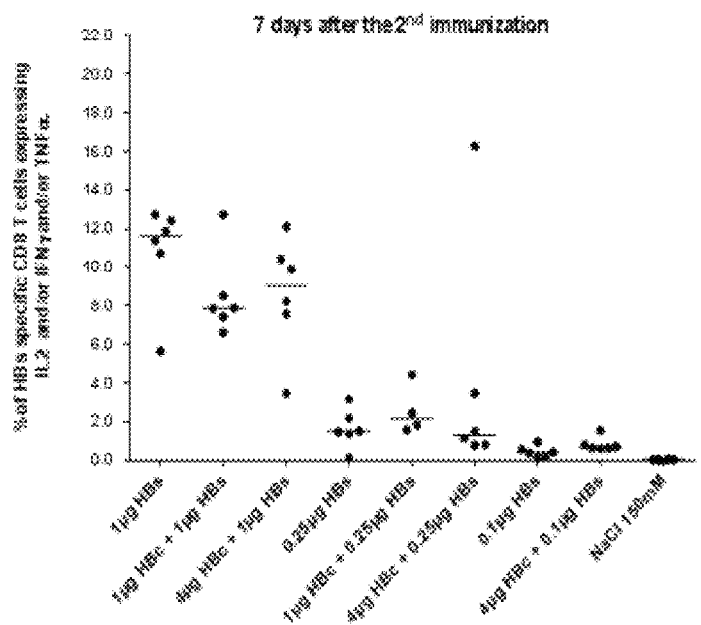
Figure 25B:
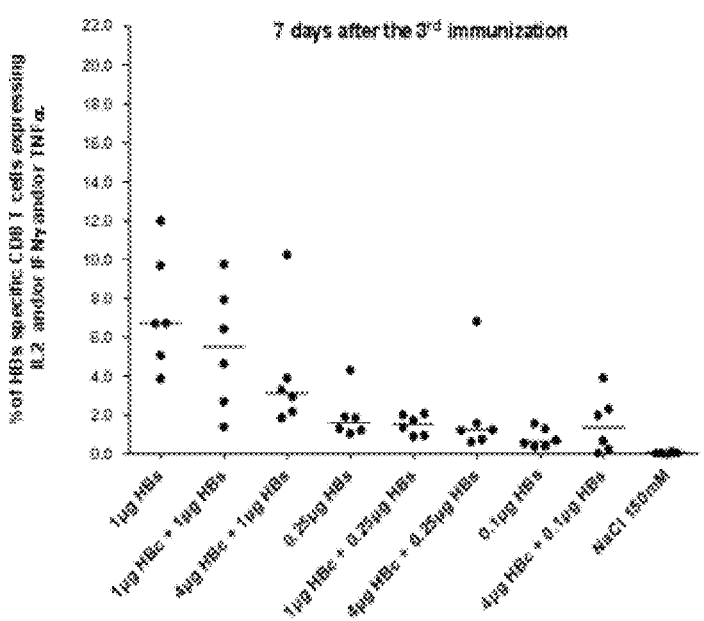

FIG. 25A and FIG. 25B—Frequency of HBs-specific CD8+ T-cells in the leukocytes of CB6F1 mice 7 days after the 2nd and the 3rd immunization with adjuvanted HBc, HBs and HBc/HBs in various ratios.

Figure 26A:
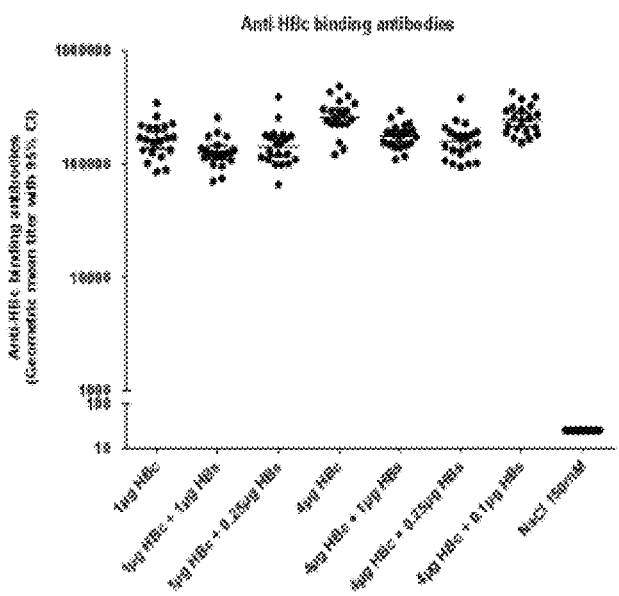
Figure 26B:
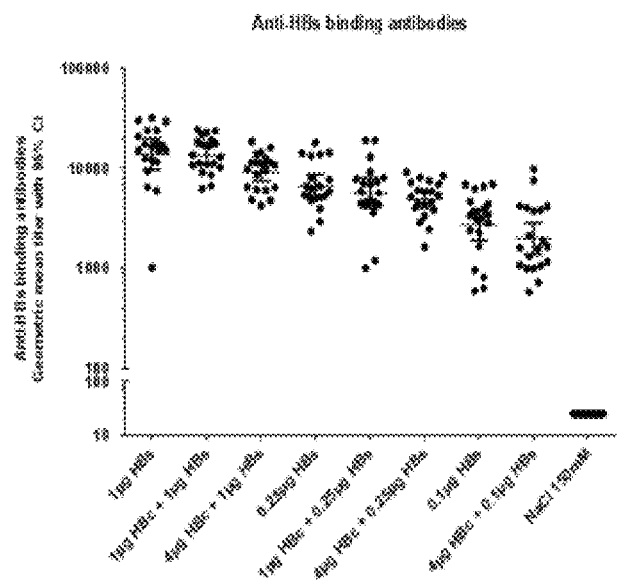

FIG. 26A and FIG. 26B—Anti-HBc and HBs-humoral responses induced in CB6F1 mice at 14 days after the 2nd immunization with adjuvanted HBc, HBs and HBc/HBs in various ratios.

Figure 27A:
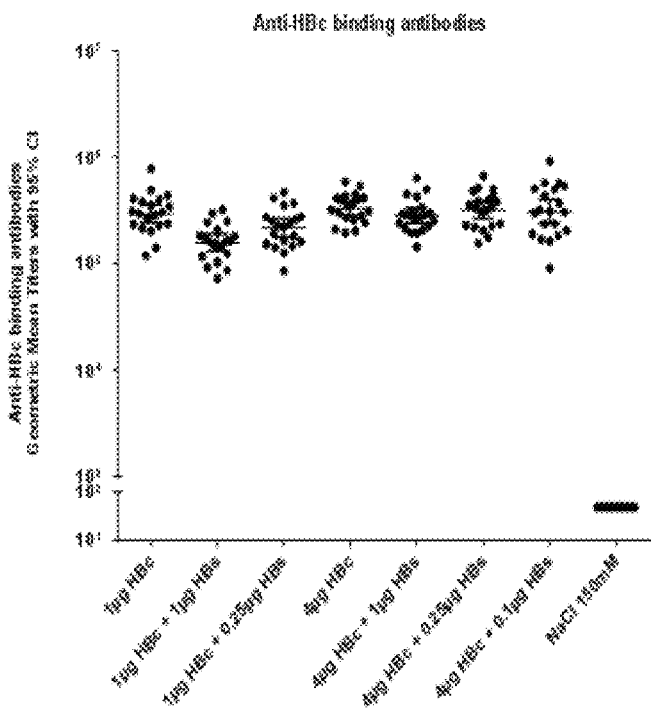
Figure 27B:
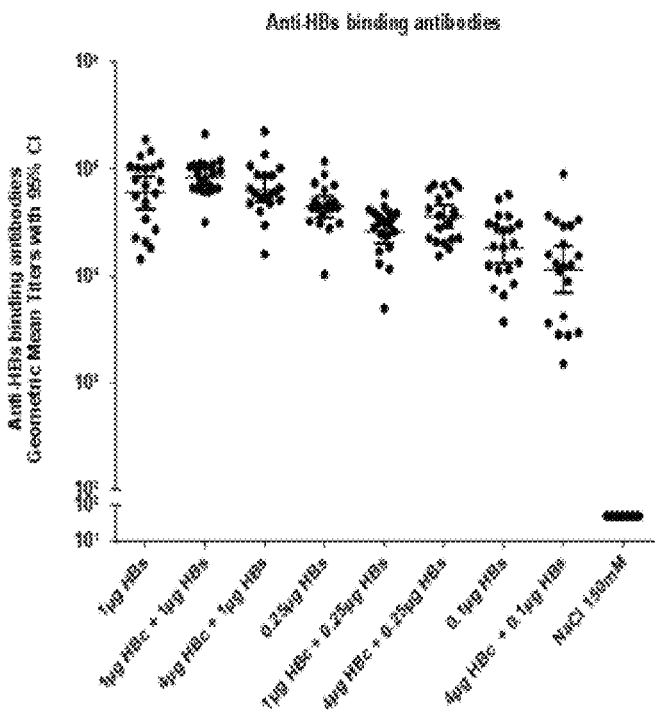

FIG. 27A and FIG. 27B—Anti-HBc and HBs-humoral responses induced in CB6F1 mice at 14 days after the 3rd immunization with adjuvanted HBc, HBs and HBc/HBs in various ratios.

SEQUENCE LISTINGS

SEQ ID NO:1: Amino acid sequence of HBs.
SEQ ID NO:2: Amino acid sequence of HBc truncate.
SEQ ID NO:3: Amino acid sequence of spacer incorporating 2A cleavage region of foot and mouth virus.
SEQ ID NO:4: Nucleotide sequence encoding spacer incorporating 2A cleavage region of foot and mouth virus.
SEQ ID NO:5: Amino acid sequence of HBc-2A-HBs.
SEQ ID NO:6: Nucleotide sequence encoding HBc-2A-HBs.
SEQ ID NO:7: Amino acid sequence of hIi.
SEQ ID NO:8: Nucleotide sequence encoding hIi.
SEQ ID NO:9: Amino acid sequence of hIi-HBc-2A-HBs.
SEQ ID NO:10: Nucleotide sequence encoding hIi-HBc-2A-HBs.
SEQ ID NO:11: Amino acid sequence of HBc.
SEQ ID NO:12: Amino acid sequence of hIi alternate variant.
SEQ ID NO:13: Nucleotide sequence encoding hI alternate variant.
SEQ ID NO:14: Alternative nucleic acid sequence of hIi-HBc-2A-HBs.
SEQ ID NO:15: Alternative amino acid sequence of hIi-HBc-2A-HBs.

DETAILED DESCRIPTION OF THE INVENTION

Definitions

Unless defined otherwise, all technical and scientific terms used herein have the same meanings as commonly understood by one of ordinary skill in the art. For example, the terms used herein are defined as described in "A multilingual glossary of biotechnological terms: (IUPAC Recommendations)", Leuenberger, H. G. W, Nagel, B. and Klbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention. All definitions provided herein in the context of one aspect of the invention also apply to the other aspects of the invention.

The terms "protein", "polypeptide" and "peptide" are used interchangeably herein and refer to any peptide-linked chain of amino acids, regardless of length, co-translational or post-translational modification. A fusion protein (or "chimeric protein") is a recombinant protein comprising two or more peptide-linked proteins. Fusion proteins are created through the joining of two or more genes that originally coded for the separate proteins. Translation of this fusion gene results in a single fusion protein. In relation to a protein or polypeptide, recombinant means that the protein is expressed from a recombinant polynucleotide.

The terms "polynucleotide" and "nucleic acid" are used interchangeably herein and refer to a polymeric macromolecule made from nucleotide monomers. Suitably the polynucleotides of the invention are recombinant. Recombinant means that the polynucleotide is the product of at least one of cloning, restriction or ligation steps, or other procedures that result in a polynucleotide that is distinct from a polynucleotide found in nature.

A heterologous nucleic acid sequence refers to any nucleic acid sequence that is not isolated from, derived from, or based upon a naturally occurring nucleic acid sequence found in the host organism. "Naturally occurring" means a sequence found in nature and not synthetically prepared or modified. A sequence is "derived" from a source when it is isolated from a source but modified (e.g., by deletion, substitution (mutation), insertion, or other modification), suitably so as not to disrupt the normal function of the source gene.

Suitably, the polynucleotides used in the present invention are isolated. An "isolated" polynucleotide is one that is removed from its original environment. For example, a naturally-occurring polynucleotide is isolated if it is separated from some or all of the coexisting materials in the natural system. A polynucleotide is considered to be isolated if, for example, it is cloned into a vector that is not a part of its natural environment or if it is comprised within cDNA.

The term "treating" as used herein in relation to chronic hepatitis B infection refers to the administration of suitable compositions with the intention of reducing the symptoms of CHB, preventing the progression of CHB or reducing the level of one or more detectable markers of CHB. The term "treatment" is to be interpreted accordingly. For example, preventing the progression of CHB may include preventing the onset of liver disease or stabilising pre-existing liver disease, as indicated by ALT (alanine transaminase) levels, liver fibrosis or other suitable detectable markers. Other markers of CHB include the serum HBV DNA level, which is an indicator of viral replication and the serum HBs antigen level, which is an indicator of viral load, thus treating CHB may include reducing the level of serum HBsAg (e.g. as determined by quantitative immunoassay) or HBV DNA (e.g. as determined by the Cobas® HBV assay (Roche) or equivalent) to undetectable levels ("clearing" HBsAg or HBV DNA).

"Concomitant" administration as used herein refers to administration during the same ongoing immune response and "concomitantly" is to be interpreted accordingly. Preferably both components are administered at the same time (such as concomitant administration of a composition comprising a vector and a composition comprising a protein), however, one component could be administered within a few minutes (for example, at the same medical appointment or doctor's visit), or within a few hours of the other component. Such administration is also referred to as co-administration. Concomitant administration of separate components may occur via the same route of administration e.g. intramuscular injection. Alternatively, concomitant administration of separate components may occur via different routes of administration e.g. intramuscular injection and intradermal injection, intramuscular and intranasal administration, inhalation and subcutaneous administration etc. In some embodiments, concomitant administration may refer to the administration of an adenoviral vector, and a protein component. In other embodiments, co-administration refers to the administration of an adenoviral vector and another viral vector, for example a poxvirus such as MVA. In other embodiments, co-administration refers to the administration of an adenoviral vector and a protein component, in which the protein component is adjuvanted.

"Sequential" administration refers to administration of a first composition, followed by administration of a second composition a significant time later. The period of time between two sequential administrations is between 1 week and 12 months, for example between 2 weeks and 12 weeks, for example, 1 week, 2 weeks, 4 weeks, 6 weeks 8 weeks or 12 weeks, 6 months or 12 months. More particularly, it is between 4 weeks and 8 weeks, for example the period of time between sequential administrations may be 4 weeks. Thus, sequential administration encompasses a first and a subsequent administration in a prime-boost setting, i.e. when the administration of the second composition is not carried out during the ongoing immune response engendered by the first administration.

"Immunogenic combination" as used herein refers to a plurality of separately formulated immunogenic compositions administered sequentially and/or concomitantly in a single immunisation regimen, e.g. a prime-boost regimen, each separately formulated immunogenic composition being a component of the immunogenic combination.

With regard to percentage homologies, looking at a pairwise alignment of two sequences, aligned identical residues ('identities') between the two sequences can be observed, A percentage of identity (or homology), can be calculated by multiplying by 100 (a) the quotient between the number of identities and the full length of the reference sequence (i.e. Percentage identity=(Number of identities×100)/Length of reference sequence.

COMPOSITIONS AND COMBINATIONS

In one aspect of the present invention, there is provided an immunogenic composition comprising a ChAd vector selected from the group consisting of ChAd3, ChAd63, ChAd83, ChAd155, ChAd157, Pan 5, Pan 6, Pan 7 (also referred to as C7) and Pan 9, in particular, ChAd63 or ChAd155, which includes a vector insert encoding HBc and HBs. In one embodiment, the polynucleotides encoding HBs and HBc are separated by a sequence encoding the 2A cleaving region of the foot and mouth disease virus (FMDV). In certain embodiments, the polynucleotides encoding HBs and HBc are separated by a sequence encoding a spacer which incorporates the 2A cleaving region of FMDV. In certain embodiments, HBc is fused to hIi. In a particular embodiment, the composition comprises a ChAd155 vector which comprises a polynucleotide vector insert encoding hIi, HBc, 2A and HBs, for example, an insert encoding a construct having the structure shown in FIG. 22. In certain embodiments, the vector insert encodes HBc (e.g. SEQ ID NO:11 or an amino acid sequence at least 98% homologous thereto) and HBs (e.g. SEQ ID NO:1 or an amino acid sequence at least 98% homologous thereto), separated by a sequence encoding a spacer which incorporates the 2A cleaving region of the foot and mouth disease virus (e.g. SEQ ID NO:3 or an amino acid sequence at least 98% homologous thereto). In certain embodiments, HBc (e.g. SEQ ID NO:11 or an amino acid sequence at least 98% homologous thereto) is fused to hIi (e.g. SEQ ID NO:7 or an amino acid sequence at least 98% homologous thereto or SEQ ID NO:12 or an amino acid sequence at least 98% homologous thereto). For example, HBc (e.g. SEQ ID NO:11) is fused to hIi (e.g. SEQ ID NO:7), or HBc (e.g. SEQ ID NO:11) is fused to hIi (e.g. SEQ ID NO:12). In one specific embodiment, the vector is a ChAd155 vector. In one embodiment, the composition comprises a ChAd155 vector which comprises a polynucleotide vector insert encoding the amino acid sequence of SEQ ID NO.9. In one embodiment, the composition comprises a ChAd155 vector which comprises a polynucleotide vector insert having the nucleotide sequence given in SEQ ID NO:10. In one embodiment, the composition comprises a ChAd155 vector which comprises a polynucleotide vector insert encoding the amino acid sequence of SEQ ID NO.15. In one embodiment, the composition comprises a ChAd155 vector which comprises a polynucleotide vector insert having the nucleotide sequence given in SEQ ID NO:14.

In one aspect of the present invention, there is provided an immunogenic composition comprising an MVA vector which includes a vector insert encoding HBc and HBs, separated by a sequence encoding the 2A cleaving region of the foot and mouth disease virus (FMDV). In certain embodiments, the polynucleotides encoding HBs and HBc are separated by a sequence encoding a spacer which incorporates the 2A cleaving region of FMDV. In a particular embodiment, the composition comprises an MVA vector which comprises a polynucleotide vector insert encoding HBc, 2A and HBs, for example, an insert encoding a construct having the structure shown in FIG. 21. In certain embodiments, the vector insert encodes HBc (e.g. SEQ ID NO:11 or an amino acid sequence at least 98% homologous thereto) and HBs (e.g. SEQ ID NO:1 or an amino acid sequence at least 98% homologous thereto), separated by a sequence encoding a spacer which incorporates the 2A cleaving region of the foot and mouth disease virus (e.g. SEQ ID NO:3 or an amino acid sequence at least 98% homologous thereto). In one embodiment, the composition comprises an MVA vector which comprises a polynucleotide vector insert encoding the amino acid sequence of SEQ ID NO.5. In one embodiment, the composition comprises an MVA vector which comprises a polynucleotide vector insert having the nucleotide sequence given in SEQ ID NO:6.

In one aspect of the present invention, there is provided an immunogenic composition comprising a full length recombinant hepatitis B surface antigen (HBs), a recombinant hepatitis B virus core antigen (HBc) truncated at the C-terminal, and an adjuvant comprising MPL and QS-21. In certain embodiments, the truncated recombinant HBc comprises the assembly domain of HBc, for example including 145-149 amino acids of the assembly domain of a wild-type core antigen protein, e.g. amino acids 1-145, 1-146, 1-147, 1-148 or amino acids 1-149 of a wild-type hepatitis B core antigen protein. In one embodiment, the composition comprises a full length recombinant HBs, amino acids 1-149 of HBc and an adjuvant comprising MPL and QS-21. In certain embodiments the recombinant protein HBs and HBc antigens are in the form of virus-like particles. In one embodiment, the composition comprises recombinant HBc and recombinant HBs in a 1:1 ratio. In another embodiment the ratio of HBc to HBs in the composition is greater than 1, for example the ratio of HBc to HBs may be 1.5:1, 2:1, 2.5:1, 3:1, 3.5:1, 4:1, 4.5:1, 5:1, 5.5:1, 6:1 or more, especially 3:1 to 5:1, such as 3:1, 4:1 or 5:1, particularly a ratio of 4:1. In particular embodiments, the composition comprises recombinant HBc and recombinant HBs in a ratio of 4:1 or more. In certain embodiments, the composition comprises a full length recombinant hepatitis B surface antigen (HBs) (e.g. SEQ ID NO:1 or an amino acid sequence at least 98% homologous thereto), a recombinant hepatitis B virus core antigen (HBc) truncated at the C-terminal, and an adjuvant comprising MPL and QS-21. In certain embodiments, the truncated recombinant HBc comprises the assembly domain of HBc, for example amino acids 1-149 of HBc (e.g. SEQ ID NO:2 or an amino acid sequence at least 98% homologous thereto). For example, the composition may comprise a full length recombinant HBs (SEQ ID NO: 1), amino acids 1-149 of HBc (SEQ ID NO: 2) and an adjuvant comprising MPL, QS-21 and liposomes composed of dioleoyl phosphatidylcholine (DOPC) and cholesterol in a phosphate buffered saline solution.

In a further aspect, there is provided an immunogenic combination comprising:
a) a composition comprising a replication-defective chimpanzee adenoviral (ChAd) vector comprising a polynucleotide encoding a hepatitis B surface antigen (HBs) and a nucleic acid encoding a hepatitis B virus core antigen (HBc);
b) a composition comprising a Modified Vaccinia Virus Ankara (MVA) vector comprising a polynucleotide encoding a hepatitis B surface antigen (HBs) and a nucleic acid encoding a hepatitis B virus core antigen (HBc); and
c) a composition comprising a recombinant hepatitis B surface antigen (HBs), recombinant hepatitis B virus core antigen (HBc) and an adjuvant.

In one embodiment, the composition of part a) of the immunogenic combination comprises a ChAd vector selected from the group consisting of ChAd3, ChAd63, ChAd83, ChAd155, ChAd157, Pan 5, Pan 6, Pan 7 (also referred to as C7) and Pan 9, in particular, ChAd63 or ChAd155, which includes a vector insert encoding HBc and HBs. In one embodiment, the polynucleotides encoding HBs and HBc are separated by a sequence encoding the 2A cleaving region of the foot and mouth disease virus (FMDV). In certain embodiments, the polynucleotides encoding HBs and HBc are separated by a sequence encoding a spacer which incorporates the 2A cleaving region of FMDV. In certain embodiments, HBc is fused to hIi. In a particular embodiment, the composition of part a) of the immunogenic combination comprises a ChAd155 vector which comprises a polynucleotide vector insert encoding hIi, HBc, 2A and HBs, for example, an insert encoding a construct having the structure shown in FIG. 22. In certain embodiments, the vector insert encodes HBc (e.g. SEQ ID NO:11 or an amino acid sequence at least 98% homologous thereto) and HBs (e.g. SEQ ID NO:1 or an amino acid sequence at least 98% homologous thereto), separated by a sequence encoding a spacer which incorporates the 2A cleaving region of the foot and mouth disease virus (e.g. SEQ ID NO:3 or an amino acid sequence at least 98% homologous thereto). In certain embodiments, HBc (e.g. SEQ ID NO:11 or an amino acid sequence at least 98% homologous thereto) is fused to hIi (e.g. SEQ ID NO:7 or an amino acid sequence at least 98% homologous thereto or SEQ ID NO:12 or an amino acid sequence at least 98% homologous thereto). For example, HBc (e.g. SEQ ID NO:11) is fused to hIi (e.g. SEQ ID NO:7), or HBc (e.g. SEQ ID NO:11) is fused to hIi (e.g. SEQ ID NO:12). In one specific embodiment, the vector is a ChAd155 vector. In one embodiment, the composition of part a) of the immunogenic combination comprises a ChAd155 vector which comprises a polynucleotide vector insert encoding the amino acid sequence of SEQ ID NO.9. In one embodiment, the composition of part a) of the immunogenic combination comprises a ChAd155 vector which comprises a polynucleotide vector insert having the nucleotide sequence given in SEQ ID NO:10. In one embodiment, the composition of part a) of the immunogenic combination comprises a ChAd155 vector which comprises a polynucleotide vector insert encoding the amino acid sequence of SEQ ID NO.15. In one embodiment, the composition of part a) of the immunogenic combination comprises a ChAd155 vector which comprises a polynucleotide vector insert having the nucleotide sequence given in SEQ ID NO:14.

In one embodiment, the composition of part b) of the immunogenic combination comprises an MVA vector which includes a vector insert encoding HBc and HBs, separated by a sequence encoding the 2A cleaving region of the foot and mouth disease virus (FMDV). In certain embodiments, the polynucleotides encoding HBs and HBc are separated by a sequence encoding a spacer which incorporates the 2A cleaving region of FMDV. In a particular embodiment, the composition of part b) of the immunogenic combination comprises an MVA vector which comprises a polynucleotide vector insert encoding HBc, 2A and HBs, for example, an insert encoding a construct having the structure shown in FIG. 21. In certain embodiments, the vector insert encodes HBc (e.g. SEQ ID NO:11 or an amino acid sequence at least 98% homologous thereto) and HBs (e.g. SEQ ID NO:1 or an amino acid sequence at least 98% homologous thereto), separated by a sequence encoding a spacer which incorporates the 2A cleaving region of the foot and mouth disease virus (e.g. SEQ ID NO:3 or an amino acid sequence at least 98% homologous thereto). In one embodiment, the composition of part b) of the immunogenic combination comprises an MVA vector which comprises a polynucleotide vector insert encoding the amino acid sequence of SEQ ID NO.5. In one embodiment, the composition of part b) of the immunogenic combination comprises an MVA vector which comprises a polynucleotide vector insert having the nucleotide sequence given in SEQ ID NO:6.

In one embodiment, the composition of part c) of the immunogenic combination comprises a full length recombinant hepatitis B surface antigen (HBs), a recombinant hepatitis B virus core antigen (HBc) truncated at the C-terminal, and an adjuvant comprising MPL and QS-21. In certain embodiments, the truncated recombinant HBc comprises the assembly domain of HBc, for example including 145-149 amino acids of the assembly domain of a wild-type core antigen protein, e.g. amino acids 1-145, 1-146, 1-147, 1-148 or amino acids 1-149 of a wild-type hepatitis B core antigen protein. In one embodiment, the composition of part c) of the immunogenic combination comprises a full length recombinant HBs, amino acids 1-149 of HBc and an adjuvant comprising MPL and QS-21. In certain embodiments the recombinant protein HBs and HBc antigens are in the form of virus-like particles. In one embodiment, the composition comprises recombinant HBc and recombinant HBs in a 1:1 ratio. In another embodiment the ratio of HBc to HBs in the composition is greater than 1, for example the ratio of HBc to HBs may be 1.5:1, 2:1, 2.5:1, 3:1, 3.5:1, 4:1, 4.5:1, 5:1, 5.5:1, 6:1 or more, especially 3:1 to 5:1, such as 3:1, 4:1 or 5:1, particularly a ratio of 4:1. In particular embodiments, the composition of part c) of the immunogenic combination comprises recombinant HBc and recombinant HBs in a ratio of 4:1 or more. In certain embodiments, the composition comprises a full length recombinant hepatitis B surface antigen (HBs) (e.g. SEQ ID NO:1), a recombinant hepatitis B virus core antigen (HBc) truncated at the C-terminal, and an adjuvant comprising MPL and QS-21. In certain embodiments, the truncated recombinant HBc comprises the assembly domain of HBc, for example amino acids 1-149 of HBc (e.g. SEQ ID NO:2). For example, the composition of part c) of the immunogenic combination comprises a full length recombinant HBs (SEQ ID NO: 1), amino acids 1-149 of HBc (SEQ ID NO: 2) and an adjuvant comprising MPL, QS-21 and liposomes composed of dioleoyl phosphatidylcholine (DOPC) and cholesterol, for example in a phosphate buffered saline solution.

Thus, in one particular embodiment, the present invention provides an immunogenic combination comprising:
a) a composition comprising a ChAd155 vector which comprises a polynucleotide vector insert encoding hIi, HBc, 2A and HBs;
b) a composition comprising an MVA vector comprising a polynucleotide vector insert encoding HBc, 2A and HBs; and
c) a composition comprising a recombinant HBs protein, a recombinant truncated HBc protein and an adjuvant comprising MPL, QS-21 and liposomes composed of dioleoyl phosphatidylcholine (DOPC) and cholesterol.

In one such embodiment, the immunogenic combination comprises:
a) a composition comprising a ChAd155 vector which comprises a polynucleotide vector insert encoding the amino acid sequence of SEQ ID NO:9 or encoding the amino acid sequence of SEQ ID NO:15;
b) a composition comprising an MVA vector comprising a polynucleotide vector insert encoding the amino acid sequence of SEQ ID NO:5; and
c) a composition comprising a recombinant HBs protein of SEQ ID NO:1, a recombinant truncated HBc protein of SEQ ID NO:2 and an adjuvant comprising MPL, QS-21 and liposomes composed of dioleoyl phosphatidylcholine (DOPC) and cholesterol.

In another embodiment, the immunogenic combination comprises:
a) a composition comprising a ChAd155 vector which comprises a polynucleotide vector insert of SEQ ID NO:10 or a polynucleotide vector insert of SEQ ID NO:14;

b) a composition comprising an MVA vector comprising a polynucleotide vector insert of SEQ ID NO.6; and
c) a composition comprising a recombinant HBs protein of SEQ ID NO:1, a recombinant truncated HBc protein of SEQ ID NO:2 and an adjuvant comprising MPL, QS-21 and liposomes composed of dioleoyl phosphatidylcholine (DOPC) and cholesterol.

In a further aspect, the present invention provides a kit comprising the following components:
a) a composition comprising a replication-defective chimpanzee adenoviral (ChAd) vector comprising a polynucleotide encoding a hepatitis B surface antigen (HBs) and a nucleic acid encoding a hepatitis B virus core antigen (HBc);
b) a composition comprising a Modified Vaccinia Virus Ankara (MVA) vector comprising a polynucleotide encoding a hepatitis B surface antigen (HBs) and a nucleic acid encoding a hepatitis B virus core antigen (HBc); and
c) a composition comprising a recombinant hepatitis B surface antigen (HBs), recombinant hepatitis B virus core antigen (HBc) and an adjuvant, with instructions for administration of the components sequentially or concomitantly for the treatment of CHB.

In one embodiment, the composition of component a) of the kit comprises a ChAd vector selected from the group consisting of ChAd3, ChAd63, ChAd83, ChAd155, ChAd157, Pan 5, Pan 6, Pan 7 (also referred to as C7) and Pan 9, in particular, ChAd63 or ChAd155, which includes a vector insert encoding HBc and HBs. In one embodiment, the polynucleotides encoding HBs and HBc are separated by a sequence encoding the 2A cleaving region of the foot and mouth disease virus (FMDV). In certain embodiments, the polynucleotides encoding HBs and HBc are separated by a sequence encoding a spacer which incorporates the 2A cleaving region of FMDV. In certain embodiments, HBc is fused to hIi. In a particular embodiment, the composition of component a) of the kit comprises a ChAd155 vector which comprises a polynucleotide vector insert encoding hIi, HBc, 2A and HBs, for example, an insert encoding a construct having the structure shown in FIG. 22. In certain embodiments, the vector insert encodes HBc (e.g. SEQ ID NO:11 or an amino acid sequence at least 98% homologous thereto) and HBs (e.g. SEQ ID NO:1 or an amino acid sequence at least 98% homologous thereto), separated by a sequence encoding a spacer which incorporates the 2A cleaving region of the foot and mouth disease virus (e.g. SEQ ID NO:3 or an amino acid sequence at least 98% homologous thereto). In certain embodiments, HBc (e.g. SEQ ID NO:11 or an amino acid sequence at least 98% homologous thereto) is fused to hIi (e.g. SEQ ID NO:7 or an amino acid sequence at least 98% homologous thereto or SEQ ID NO:12 or an amino acid sequence at least 98% homologous thereto). For example, HBc (e.g. SEQ ID NO:11) is fused to hIi (e.g. SEQ ID NO:7), or HBc (e.g. SEQ ID NO:11) is fused to hIi (e.g. SEQ ID NO:12). In one specific embodiment, the vector is a ChAd155 vector. In one embodiment, the composition of component a) of the kit comprises a ChAd155 vector which comprises a polynucleotide vector insert encoding the amino acid sequence of SEQ ID NO.9. In one embodiment, the composition of component a) of the kit comprises a ChAd155 vector which comprises a polynucleotide vector insert having the nucleotide sequence given in SEQ ID NO:10. In one embodiment, the composition component a) of the kit comprises a ChAd155 vector which comprises a polynucleotide vector insert encoding the amino acid sequence of SEQ ID NO.15. In one embodiment, the composition of component a) of the kit comprises a ChAd155 vector which comprises a polynucleotide vector insert having the nucleotide sequence given in SEQ ID NO:14.

In one embodiment, the composition of component b) of the kit comprises an MVA vector which includes a vector insert encoding HBc and HBs, separated by a sequence encoding the 2A cleaving region of the foot and mouth disease virus (FMDV). In certain embodiments, the polynucleotides encoding HBs and HBc are separated by a sequence encoding a spacer which incorporates the 2A cleaving region of FMDV. In a particular embodiment, the composition of component b) of the kit comprises an MVA vector which comprises a polynucleotide vector insert encoding HBc, 2A and HBs, for example, an insert encoding a construct having the structure shown in FIG. 21. In certain embodiments, the vector insert encodes HBc (e.g. SEQ ID NO:11 or an amino acid sequence at least 98% homologous thereto) and HBs (e.g. SEQ ID NO:1 or an amino acid sequence at least 98% homologous thereto), separated by a sequence encoding a spacer which incorporates the 2A cleaving region of the foot and mouth disease virus (e.g. SEQ ID NO:3 or an amino acid sequence at least 98% homologous thereto). In one embodiment, the composition of component b) of the kit comprises an MVA vector which comprises a polynucleotide vector insert encoding the amino acid sequence of SEQ ID NO.5. In one embodiment, the composition component b) of the kit comprises an MVA vector which comprises a polynucleotide vector insert having the nucleotide sequence given in SEQ ID NO:6.

In one embodiment, the composition component c) of the kit comprises a full length recombinant hepatitis B surface antigen (HBs), a recombinant hepatitis B virus core antigen (HBc) truncated at the C-terminal, and an adjuvant comprising MPL and QS-21. In certain embodiments, the truncated recombinant HBc comprises the assembly domain of HBc, for example including 145-149 amino acids of the assembly domain of a wild-type core antigen protein, e.g. amino acids 1-145, 1-146, 1-147, 1-148 or amino acids 1-149 of a wild-type hepatitis B core antigen protein. In one embodiment, the composition of component c) of the kit comprises a full length recombinant HBs, amino acids 1-149 of HBc and an adjuvant comprising MPL and QS-21. In certain embodiments the recombinant protein HBs and HBc antigens are in the form of virus-like particles. In one embodiment, the composition comprises recombinant HBc and recombinant HBs in a 1:1 ratio. In another embodiment the ratio of HBc to HBs in the composition is greater than 1, for example the ratio of HBc to HBs may be 1.5:1, 2:1, 2.5:1, 3:1, 3.5:1, 4:1, 4.5:1, 5:1, 5.5:1, 6:1 or more, especially 3:1, 4:1 or 5:1, particularly a ratio of 4:1. In particular embodiments, the composition of component c) of the kit comprises recombinant HBc and recombinant HBs in a ratio of 4:1 or more. In certain embodiments, the composition comprises a full length recombinant hepatitis B surface antigen (HBs) (e.g. SEQ ID NO:1), a recombinant hepatitis B virus core antigen (HBc) truncated at the C-terminal, and an adjuvant comprising MPL and QS-21. In certain embodiments, the truncated recombinant HBc comprises the assembly domain of HBc, for example amino acids 1-149 of HBc (e.g. SEQ ID NO:2). For example, the composition of component c) of the kit comprises a full length recombinant HBs (SEQ ID NO: 1), amino acids 1-149 of HBc (SEQ ID NO: 2) and an adjuvant comprising MPL, QS-21 and liposomes composed of dioleoyl phosphatidylcholine (DOPC) and cholesterol, for example in a phosphate buffered saline solution.

In one embodiment the kit comprises the following components:
- a) a composition comprising a ChAd155 vector which comprises a polynucleotide vector insert of SEQ ID NO:10 or a polynucleotide vector insert of SEQ ID NO:14;
- b) a composition comprising an MVA vector comprising a polynucleotide vector insert of SEQ ID NO:6; and
- c) a composition comprising a recombinant HBs protein of SEQ ID NO:1, a recombinant truncated HBc protein of SEQ ID NO:2 and an adjuvant comprising MPL, QS-21 and liposomes composed of dioleoyl phosphatidylcholine (DOPC) and cholesterol, with instructions for administration of the components sequentially or concomitantly for the treatment of CHB.

Regimens

The present disclosure describes a vaccine regimen which provides for a heterologous prime-boost schedule with two viral vectors coding for the hepatitis B core (HBc) and the hepatitis B surface (HBs) antigens in order to induce a strong CD8+ T-cell response, with sequential or concomitant administration of adjuvanted recombinant HBc and HBs proteins in order to induce strong antigen-specific CD4+ T-cell and antibody responses. The present disclosure further describes immunogenic compositions and combinations which may find use as vaccine compositions. Such compositions and combinations may be used in the disclosed regimens. The disclosed vaccine compositions and regimens successfully restored HBs- and HBc-specific antibody and CD8+ T cell responses as well as HBs-specific CD4+ T cell responses, without associated signs of liver alteration side effects, in a mouse model which recapitulates virological and immunological characteristics of human chronic HBV infection.

The immunogenic compositions and immunogenic combinations described herein may find use in a method of treating chronic hepatitis B infection (CHB) in a human, comprising the steps of:
- a) administering to the human a composition comprising a replication-defective chimpanzee adenoviral (ChAd) vector comprising a polynucleotide encoding a hepatitis B surface antigen (HBs) and a nucleic acid encoding a hepatitis B virus core antigen (HBc);
- b) administering to the human a composition comprising a Modified Vaccinia Virus Ankara (MVA) vector comprising a polynucleotide encoding a hepatitis B surface antigen (HBs) and a nucleic acid encoding a hepatitis B virus core antigen (HBc); and
- c) administering to the human a composition comprising a recombinant hepatitis B surface antigen (HBs), recombinant hepatitis B virus core antigen (HBc) and an adjuvant.

In one embodiment, the steps of the method are carried out sequentially, with step a) preceding step b) and step b) preceding step c). Optionally, step c) may be repeated. In certain embodiments the period of time between the steps of the method is 2 to 12 weeks, for example 2 weeks, 3 weeks, 4 weeks, 5 weeks, 6 weeks, 7 weeks, 8 weeks, 9 weeks, 10 weeks, 11 weeks or 12 weeks. In one embodiment the period of time between the steps of the method is 4 to 8 weeks. In one embodiment, the period of time between sequential administrations of compositions according to the method is 4 weeks. In another embodiment, step c) is carried out concomitantly with step a) and/or with step b). In certain embodiments, concomitant steps b) and c) may be repeated. In a further embodiment, step c is repeated and the steps of the method are carried out in the following order: step a), step b), step c), step c). In certain embodiments the period of time between the steps of the method is 2 to 12 weeks, for example 2 weeks, 3 weeks, 4 weeks, 5 weeks, 6 weeks, 7 weeks, 8 weeks, 9 weeks, 10 weeks, 11 weeks or 12 weeks. In one embodiment the period of time between the steps of the method is 4 to 8 weeks. In one embodiment, the period of time between sequential administrations of compositions according to the method is 4 weeks.

In another aspect, the immunogenic compositions and immunogenic combinations may find use in a method of treating chronic hepatitis B infection (CHB) in a human, comprising the steps of:
- a) administering to the human i) a composition comprising a replication-defective chimpanzee adenoviral (ChAd) vector comprising a polynucleotide encoding a hepatitis B surface antigen (HBs) and a nucleic acid encoding a hepatitis B virus core antigen (HBc) and, concomitantly, ii) a composition comprising a recombinant hepatitis B surface antigen (HBs), recombinant hepatitis B virus core antigen (HBc) and an adjuvant; and
- b) administering to the human i) a composition comprising a Modified Vaccinia Virus Ankara (MVA) vector comprising a polynucleotide encoding a hepatitis B surface antigen (HBs) and a nucleic acid encoding a hepatitis B virus core antigen (HBc) and, concomitantly, a composition comprising a recombinant hepatitis B surface antigen (HBs), recombinant hepatitis B virus core antigen (HBc) and an adjuvant.

In one embodiment, the steps of the method are carried out sequentially, with step a) preceding step b). Optionally, step b) may be repeated. Optionally, step a) may be repeated. In one embodiment, the method steps are carried out in the order: step a) followed by step a) followed by step b). Alternatively, the method steps may be carried out in the order: step a) followed by step b) followed by step a). Optionally, step b) may be repeated. In one embodiment, the method steps are carried out in the order: step a) followed by step b) followed by step b). In an alternative embodiment, the method steps are carried out in the order: step b) followed by step a) followed by step b). Optionally, step b) may be repeated more than once. Optionally both step a) and step b) may be repeated. In one embodiment, the method steps are carried out in the order: step a) followed by step b) followed by step b) followed by step b). In a further embodiment, the method steps are carried out in the order: step a) followed by step a) followed by step b) followed by step b), optionally followed by step b). In certain embodiments the period of time between the steps of the method is 2 to 12 weeks, for example 2 weeks, 3 weeks, 4 weeks, 5 weeks, 6 weeks, 7 weeks, 8 weeks, 9 weeks, 10 weeks, 11 weeks or 12 weeks. In one embodiment the period of time between the steps of the method is 4 to 8 weeks. In one embodiment, the period of time between sequential administrations of compositions according to the method is 4 weeks.

Antigens

At least nine genotypes (A through I) of HBV have been identified, differing in their genome by more than 8%. Within a given HBV genotype, multiple geno-subtypes have been identified, differing by 4-8%. The antigens for use in the disclosed methods are suitably selected to provide immunological coverage across multiple, preferably all HBV genotypes. The hepatitis B core protein antigen (HBc) is highly conserved across genotypes and geno-subtypes and the hepatitis B surface protein antigen (HBs) sequence is suitably selected to include key cross-genotype-preserved B-cell epitopes which allow for induction of broad neutralizing responses. Suitably, the sequences of the HBc and of the HBs for use in the disclosed methods and compositions are based upon those from genotype/subtype A2.

Suitably, the HBs antigen for use in the disclosed methods and compositions is derived from the small, middle or large surface antigen protein. In particular, a suitable HBs antigen comprises the small (S) protein of HBV adw2 strain, genotype A. For example, a suitable HBs antigen has the 226 amino acids of amino acid sequence SEQ ID NO:1. When used as recombinant protein, the HBs antigen preferably assembles into virus-like particles. This antigen is included in well-studied marketed hepatitis-B prophylactic vaccines (Engerix B, Fendrix, Twinrix and others), and has been demonstrated to be protective against hepatitis B, across genotypes. Preferably the recombinant HBs protein antigen is expressed from yeast and purified for use in the vaccine compositions and methods of the present invention. Suitable methods for expression and purification are known, for example from EP1307473B1.

The hepatitis B core protein (HBc) is the major component of the nucleocapsid shell packaging the viral genome. This protein (183-185 aa long) is expressed in the cytoplasm of infected cells and remains unglycosylated. HBc comprises a 149 residue assembly domain and a 34-36 residue RNA-binding domain at the C terminus. The HBc antigen for use in the disclosed methods and compositions may be full length or may comprise a C-terminally truncated protein (lacking the RNA-binding C-terminus), for example including 145-149 amino acids of the assembly domain of a wild-type core antigen protein, e.g. amino acids 1-145, 1-146, 1-147, 1-148 or amino acids 1-149 of a wild-type hepatitis B core antigen protein. The truncated protein retains the ability to assemble into nucleocapsid particles. A suitable HBc antigen for use in the disclosed methods and compositions has an amino acid sequence from HBV adw2 strain, genotype A. When used as recombinant protein, the HBc antigen is suitably truncated from the wild-type at the C-terminus, in particular, the antigen may be amino acids 1-149 of HBc, for example, may have the amino acid sequence of SEQ ID NO:2. Preferably the recombinant HBc protein antigen is expressed from *E. coli* and purified for use in the vaccine compositions and methods of the present invention. Methods for recombinant expression of viral proteins in *E. coli* are well known in the art.

When used as recombinant protein, the HBc antigen preferably assembles into virus-like particles. When expressed from a viral vector, the HBc antigen may be full-length or truncated, for example is suitably a full length HBc antigen (e.g. SEQ ID NO:11). Suitable doses of recombinant HBs protein antigen for use in the methods disclosed herein are from 10 ug per dose to 100 ug per dose, such as 10 ug, 15 ug, 20 ug, 25 ug, 30 ug, 35 ug, 40 ug, 45 ug, 50 ug, 55 ug, 60 ug, 65 ug, 70 ug, 75 ug, 80 ug, 85 ug, 90 ug, 95 ug, or 100 ug per dose. Suitable doses of recombinant HBc antigen protein for use in the methods disclosed herein are from 10 ug per dose to 100 ug per dose, such as 10 ug, 15 ug, 20 ug, 25 ug, 30 ug, 35 ug, 40 ug, 45 ug, 50 ug, 55 ug, 60 ug, 65 ug, 70 ug, 75 ug, 80 ug, 85 ug, 90 ug, 95 ug, or 100 ug per dose.

Antigens are substances which induce an immune response in the body, especially the production of antibodies. Antigens may be of foreign, i.e. pathogenic, origin or stem from the organism itself, the latter are referred to as self- or auto antigens. Antigens can be presented on the surface of antigen presenting cells by MHC molecules. There are two classes of MHC molecules, MHC class I (MHC-I) and MHC-class-II (MHC-II). The MHC-II molecules are membrane-bound receptors which are synthesized in the endoplasmic reticulum and leave the endoplasmic reticulum in a MHC class II compartment. In order to prevent endogenous peptides, i.e. self-antigens, from binding to the MHC-II molecule and being presented to generate an immune response, the nascent MHC-II molecule combines with another protein, the invariant chain, which blocks the peptide-binding cleft of the MHC-II molecule. The human invariant chain (hIi, also known as CD74 when expressed on the plasma membrane), is an evolutionarily conserved type II membrane protein which has several roles within the cell and throughout the immune system [Borghese, 2011]. When the MHC class II compartment fuses to a late endosome containing phagocytosed and degraded foreign proteins, the invariant chain is cleaved to leave only the CLIP region bound to the MHC-II molecule. In a second step, CLIP is removed by an HLA-DM molecule leaving the MHC-II molecule free to bind fragments of the foreign proteins. Said fragments are presented on the surface of the antigen-presenting cell once the MHC class II compartment fuses with the plasma membrane, thus presenting the foreign antigens to other cells, primarily T-helper cells.

It is known that the immune response against an antigen is increased when an adenovirus expression system encoding a fusion of invariant chain and said antigen is used for vaccination (see WO2007/062656, which also published as US2011/0293704 and is incorporated by reference for the purpose of disclosing invariant chain sequences), i.e. the invariant chain enhances the immunogenicity of the antigen and an invariant chains such as hIi is sometimes referred to as a "genetic adjuvant" in recognition of this effect. Moreover, said adenoviral construct has proven useful for priming an immune response in the context of prime-boosting vaccination regimens (see WO2014/141176, which also published as US2016/0000904; and WO2010/057501, which also published as US2010/0278904 and is incorporated by reference for the purpose of disclosing invariant chain sequences and adenoviral vectors encoding invariant chain sequences). In particular, the hIi sequence and hIi has the potential to increase $CD8^+$ T-cell responses [Spencer, 2014; Capone, 2014]. In certain embodiments, a nucleotide sequence included within a vector for use in the methods, uses and compositions disclosed herein may include a nucleotide sequence coding for hIi. The amino acid sequence for hIi as can be included in the disclosed adenoviral vector ChAd155-hIi-HBV is set out in SEQ ID NO:7, and an alternative sequence is set out in SEQ ID NO:12. Nucleotide sequences encoding these amino acid sequences are set out in SEQ ID NO:8 and SEQ ID NO:13. Suitably, a nucleotide sequence coding for hIi is fused to the nucleotide sequence coding for the HBc antigen so as to produce a fusion protein in which an hIi polypeptide is N-terminally fused to the HBc antigen.

Vectors

In addition to the polynucleotide encoding the antigen proteins (also referred to herein as the "insert"), the vectors for use in the methods and compositions disclosed herein may also include conventional control elements which are operably linked to the encoding polynucleotide in a manner that permits its transcription, translation and/or expression in a cell transfected with the vector. Thus, the vector insert polynucleotide which encodes the protein antigens is incorporated into an expression cassette with suitable control elements.

Expression control elements include appropriate transcription initiation, termination, promoter and enhancer sequences; efficient RNA processing signals such as splicing and polyadenylation (poly A) signals including rabbit beta-globin polyA; sequences that stabilize cytoplasmic mRNA; sequences that enhance translation efficiency (e.g., Kozak consensus sequence); sequences that enhance protein stability; and when desired, sequences that enhance secretion of the encoded product.

A promoter is a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and mammals (including humans). A great number of expression control sequences, including promoters which are internal, native, constitutive, inducible and/or tissue-specific, are known in the art and may be utilized.

Examples of constitutive promoters include, the TBG promoter, the retroviral Rous sarcoma virus (RSV) LTR promoter (optionally with the RSV enhancer), the cytomegalovirus (CMV) promoter (optionally with the CMV enhancer, see, e.g., Boshart et al, Cell, 41:521-530 (1985)), the CASI promoter, the SV40 promoter, the dihydrofolate reductase promoter, the β-actin promoter, the phosphoglycerol kinase (PGK) promoter, and the EF1a promoter (Invitrogen). Suitably the promoter is an CMV promoter or variant thereof, more suitably a human CMV (HCMV) promoter or variant thereof.

Adenoviral Vectors

Adenovirus has been widely used for gene transfer applications due to its ability to achieve highly efficient gene transfer in a variety of target tissues and its large transgene capacity. Conventionally, E1 genes of adenovirus are deleted and replaced with a transgene cassette consisting of the promoter of choice, cDNA sequence of the gene of interest and a poly A signal, resulting in a replication defective recombinant virus. Human adenovirus vectors have been shown to be potent vectors for the induction of CD8⁺ T-cell response to transgene, in animal models as well as in humans. Adenoviruses have a broad tropism and have the capability to infect replicating as well as non-replicating cells. The main limitation for clinical application of vectors based of human adenovirus is the high prevalence of neutralizing antibodies in the general population. Adenoviruses isolated from alternative species have been considered as potential vaccine vectors to circumvent the issue of the pre-existing anti-adenovirus immunity in humans. Among them, simian adenoviruses derived from chimpanzees, gorillas or bonobos may be suitable for use in delivering antigens and eliciting a targeted T cell and/or humoral response to those antigens in humans. Simian adenoviruses including those derived from chimpanzees have been tested in clinical research. Chimpanzee adenoviral vectors have low/no seroprevalence in the human population, are not known to cause pathological illness in humans and some ChAd vectors can be grown to high titres in cell lines previously used for production of clinical-grade material such as human embryonic kidney cells 293 (HEK 293).

A replication-incompetent or replication-defective adenovirus is an adenovirus which is incapable of replication because it has been engineered to comprise at least a functional deletion (or "loss-of-function" mutation), i.e. a deletion or mutation which impairs the function of a gene without removing it entirely, e.g. introduction of artificial stop codons, deletion or mutation of active sites or interaction domains, mutation or deletion of a regulatory sequence of a gene etc, or a complete removal of a gene encoding a gene product that is essential for viral replication, such as one or more of the adenoviral genes selected from E1A, E1B, E2A, E2B, E3 and E4 (such as E3 ORF1, E3 ORF2, E3 ORF3, E3 ORF4, E3 ORF5, E3 ORF6, E3 ORF7, E3 ORF8, E3 ORF9, E4 ORF7, E4 ORF6, E4 ORF5, E4 ORF4, E4 ORF3, E4 ORF2 and/or E4 ORF1). Suitably the E1 and E3 genes are deleted. More suitably the E1, E3 and E4 genes are deleted.

Suitable vectors for use in the methods and compositions disclosed herein are replication-defective chimpanzee adenoviral vectors, for example ChAd3, ChAd63, ChAd83, ChAd155, ChAd157, Pan 5, Pan 6, Pan 7 (also referred to as C7) or Pan 9. Examples of such strains are described in WO03/000283, WO2005/071093, WO2010/086189 and WO2016/198621. The ChAd155 vector (see WO2016/198621 which is incorporated by reference for the purpose of disclosing ChAd155 vector sequences and methods) belongs to the same phylogenetic adenovirus group as the ChAd3 vector (group C). In one embodiment, a vector for use in the methods and compositions disclosed herein is a ChAd vector of phylogenetic group C, for example ChAd3 or ChAd155. In one specific embodiment, a method of treating chronic hepatitis B disclosed herein comprises the step of administering to a human a composition comprising a ChAd155 vector comprising a polynucleotide encoding a hepatitis B surface antigen (HBs) and a nucleic acid encoding a hepatitis B virus core antigen (HBc). A suitable dose of a ChAd vector for use in the methods disclosed herein is $1 \times 10^8$-$1 \times 10^{11}$ vial particles (vp) per dose, for example about $1 \times 10^8$, $5 \times 10^8$, $1 \times 10^9$, $5 \times 10^9$, $1 \times 10^{10}$, $5 \times 10^{10}$ or $1 \times 10^{11}$ viral particles (vp) per dose.

More specifically, in one embodiment a vector for use in the methods and compositions disclosed herein is a replication-defective Chimpanzee Adenovirus vector ChAd155 encoding a fusion of sequences derived from two HBV proteins: HBc (core, nucleocapsid protein) and HBs (small surface antigen). In certain specific embodiments, the vector is ChAd155 encoding HBc and HBs, separated by SEQ ID NO:3, a spacer which incorporates a sequence encoding the 2A cleaving region of the foot and mouth disease virus (resulting in a 23 amino acid tail at the C-terminal of the upstream protein and a single proline at the N-terminal of the downstream protein), for processing of the HBc and HBs into separate proteins. Cleavage of the core from the surface antigens permits proper folding of HBs, allowing generation of an antibody response to the surface antigen. Alternatively, the adenoviral vector may be a dual-promoter (bi-cistronic) vector to allow independent expression of the HBs and HBc antigens.

In certain embodiments, the N-terminal part of the gene encoding the HBc protein may be fused to the gene encoding the human Major Histocompatibility Complex (MHC) class II-associated Invariant chain, p35 isoform (i.e. hIi or CD74). Thus, a particular ChAd155 vector for use in the methods and compositions disclosed herein comprises a polynucleotide vector insert encoding a construct having the structure shown in FIG. 22, comprising hIi, HBc, 2A and HBs. The amino acid sequence of such a construct is given in SEQ ID NO:9 and a nucleotide sequence encoding the amino acid sequence of the construct is given in SEQ ID NO:10. The amino acid sequence of an alternative such construct is given in SEQ ID NO:15 and a nucleotide sequence encoding the amino acid sequence of the construct is given in SEQ ID NO:14.

Modified Vaccinia Virus Ankara (MVA) Vector

Modified Vaccinia Virus Ankara (MVA), replication-deficient in humans and other mammals, is derived from the vaccinia virus. It belongs to the poxvirus family and was initially developed to improve the safety of smallpox vaccination by passage of vaccinia virus over 570 times in chicken embryo fibroblast (CEF) cells, resulting in multiple deletions after which the virus was highly attenuated and replication-deficient in humans and other mammals. The replication defect occurs at a late stage of virion assembly such that viral and recombinant gene expression is unimpaired making MVA an efficient single round expression vector incapable of causing infection in mammals. MVA has subsequently been extensively used as a viral vector to induce antigen-specific immunity against transgenes, both in animal models and in humans. A description of MVA can be found in Mayr A, et. al. (1978) and in Mayr, A. et. al., (1975).

In one embodiment, MVA is derived from the virus seed batch 460 MG obtained from 571th passage of Vaccinia Virus on CEF cells. In another embodiment, MVA is derived from the virus seed batch MVA 476 MG/14/78. In a further embodiment, MVA is derived or produced prior to 31 Dec. 1978 and is free of prion contamination. A suitable dose of a MVA vector for use in the methods disclosed herein is $1 \times 10^6$-$1 \times 10^9$ plaque forming units (pfu) per dose, for example about $1 \times 10^6$, $2 \times 10^6$, $5 \times 10^6$, $1 \times 10^7$, $2 \times 10^7$, $5 \times 10^7$, $1 \times 10^8$, $2 \times 10^8$, $5 \times 10^8$ or $1 \times 10^9$ pfu per dose.

In one specific embodiment, a vector for use in the methods and compositions disclosed herein is MVA encoding a fusion of sequences derived from two HBV proteins: HBc (core nucleocapsid protein) and HBs (small surface antigen). In certain embodiments, a vector for use in the methods and compositions disclosed herein is MVA encoding HBc and HBs, separated by a nucleotide sequence encoding SEQ ID NO:3, a spacer which incorporates a sequence encoding the 2A cleaving region of the foot and mouth disease virus (resulting in a 23 amino acid tail at the C-terminal of the upstream protein and a single proline at the N-terminal of the downstream protein), for processing of the HBc and HBs into separate proteins. Thus, a particular MVA vector for use in the methods and compositions disclosed herein comprises a polynucleotide vector insert encoding a construct having the structure shown in FIG. 21, comprising HBc, 2A and HBs. The amino acid sequence of such a construct is given in SEQ ID NO.5 and a nucleotide sequence encoding the amino acid insert construct is given in SEQ ID NO:6.

Pharmaceutical Compositions

The immunogenic compositions disclosed herein, which find use in the disclosed methods, are suitably pharmaceutically acceptable compositions. Suitably, a pharmaceutical composition will include a pharmaceutically acceptable carrier.

The immunogenic compositions which comprise ChAd or MVA vectors may be prepared for administration by suspension of the viral vector particles in a pharmaceutically or physiologically acceptable carrier such as isotonic saline or other isotonic salts solution. The appropriate carrier will be evident to those skilled in the art and will depend in large part upon the route of administration.

The compositions which comprise recombinant protein antigens may be prepared by isolation and purification of the proteins from the cell culture in which they are expressed, suspension in a formulation buffer which includes one or more salts, surfactants and/or cryoprotectants, and lyophilized. For example, a suitable formulation buffer may include a sugar, or a mixture of sugars e.g. sucrose, trehalose or sucralose as a cryoprotectant and a non-ionic copolymer e.g. a poloxamer as a surfactant. For administration, lyophilised recombinant protein formulations are reconstituted in a pharmaceutically or physiologically acceptable carrier such as isotonic saline or other isotonic salts solution for injection or inhalation. The appropriate carrier will be evident to those skilled in the art and will depend in large part upon the route of administration. The reconstituted composition may also include an adjuvant or mixture of adjuvants. in one embodiment, the lyophilised recombinant proteins are reconstituted in a liquid adjuvant system formulation.

The term "carrier", as used herein, refers to a pharmacologically inactive substance such as but not limited to a diluent, excipient, or vehicle with which the therapeutically active ingredient is administered. Liquid carriers include but are not limited to sterile liquids, such as saline solutions in water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. Examples of suitable pharmaceutical carriers are described in "Remington's Pharmaceutical Sciences" by E. W. Martin.

Compositions for use in the methods disclosed herein may include, in addition to the vector or recombinant proteins of the composition, an adjuvant system. The term "adjuvant" refers to an agent that augments, stimulates, activates, potentiates, or modulates the immune response to an antigen of the composition at either the cellular or humoral level, e.g. immunologic adjuvants stimulate the response of the immune system to the antigen, but have no immunological effect by themselves. The immunogenic compositions disclosed herein may include an adjuvant as a separate ingredient in the formulation, whether or not a vector comprised in the composition also encodes a "genetic adjuvant" such as hIi.

Suitable adjuvants are those which can enhance the immune response in subjects with chronic conditions and subverted immune competence. CHB patients are characterised by their inability to mount an efficient innate and adaptive immune response to the virus, which rends efficient vaccine development challenging. In these patients, one key function of an adjuvanted vaccine formulation should aim to direct the cell-mediated immune response towards a T Helper 1 (Th1) profile recognised to be critical for the removal of intracellular pathogens.

Examples of suitable adjuvants include but are not limited to inorganic adjuvants (e.g. inorganic metal salts such as aluminium phosphate or aluminium hydroxide), organic non-peptide adjuvants (e.g. saponins, such as QS21, or squalene), oil-based adjuvants (e.g. Freund's complete adjuvant and Freund's incomplete adjuvant), cytokines (e.g. IL-1β, IL-2, IL-7, IL-12, IL-18, GM-CFS, and INF-γ) particulate adjuvants (e.g. immuno-stimulatory complexes (ISCOMS), liposomes, or biodegradable microspheres), virosomes, bacterial adjuvants (e.g. monophosphoryl lipid A (MPL), such as 3-de-O-acylated monophosphoryl lipid A (3D-MPL), or muramyl peptides), synthetic adjuvants (e.g. non-ionic block copolymers, muramyl peptide analogues, or synthetic lipid A), synthetic polynucleotides adjuvants (e.g. polyarginine or polylysine) and immunostimulatory oligonucleotides containing unmethylated CpG dinucleotides ("CpG"). In particular, the adjuvant(s) may be organic non-peptide adjuvants (e.g. saponins, such as QS21, or squalene) and/or bacterial adjuvants (e.g. monophosphoryl lipid A (MPL), such as 3-de-O-acylated monophosphoryl lipid A (3D-MPL).

One suitable adjuvant is monophosphoryl lipid A (MPL), in particular 3-de-O-acylated monophosphoryl lipid A (3D-MPL). Chemically it is often supplied as a mixture of 3-de-O-acylated monophosphoryl lipid A with either 4, 5, or 6 acylated chains. It can be purified and prepared by the methods taught in GB 2122204B, which reference also discloses the preparation of diphosphoryl lipid A, and 3-O-deacylated variants thereof. Other purified and synthetic lipopolysaccharides have been described [U.S. Pat. No. 6,005,099 and EP0729473B1; Hilgers, 1986; Hilgers, 1987; and EP0549074B1].

Saponins are also suitable adjuvants [Lacaille-Dubois, 1996]. For example, the saponin Quil A (derived from the bark of the South American tree *Quillaja saponaria* Molina), and fractions thereof, are described in U.S. Pat. No. 5,057,540 and Kensil, 1996; and EP 0 362 279 B1. Purified fractions of Quil A are also known as immunostimulants, such as QS21 and QS17; methods of their production are disclosed in U.S. Pat. No. 5,057,540 and EP 0 362 279 B1. Use of QS21 is further described in Kensil, 1991. Combinations of QS21 and polysorbate or cyclodextrin are also known (WO 99/10008). Particulate adjuvant systems comprising fractions of QuilA, such as QS21 and QS7 are described in WO 96/33739 and WO 96/11711.

Adjuvants such as those described above may be formulated together with carriers, such as liposomes, oil in water emulsions, and/or metallic salts (including aluminum salts such as aluminum hydroxide). For example, 3D-MPL may be formulated with aluminum hydroxide (EP 0 689 454) or oil in water emulsions (WO 95/17210); QS21 may be formulated with cholesterol containing liposomes (WO 96/33739), oil in water emulsions (WO 95/17210) or alum (WO 98/15287).

Combinations of adjuvants may be utilized in the disclosed compositions, in particular a combination of a monophosphoryl lipid A and a saponin derivative (see, e.g., WO 94/00153; WO 95/17210; WO 96/33739; WO 98/56414; WO 99/12565; WO 99/11241), more particularly the combination of QS21 and 3D-MPL as disclosed in WO 94/00153, or a composition where the QS21 is quenched in cholesterol-containing liposomes (DQ) as disclosed in WO 96/33739. A potent adjuvant formulation involving QS21, 3D-MPL & tocopherol in an oil in water emulsion is described in WO 95/17210 and is another formulation which may find use in the disclosed compositions. Thus, suitable adjuvant systems include, for example, a combination of monophosphoryl lipid A, preferably 3D-MPL, together with an aluminium salt (e.g. as described in WO00/23105). A further exemplary adjuvant comprises QS21 and/or MPL and/or CpG. QS21 may be quenched in cholesterol-containing liposomes as disclosed in WO 96/33739.

Accordingly, a suitable adjuvant for use in the disclosed immunogenic compositions is AS01, a liposome based adjuvant containing MPL and QS-21. The liposomes, which are the vehicles for the MPL and QS-21 immuno-enhancers, are composed of dioleoyl phosphatidylcholine (DOPC) and cholesterol in a phosphate buffered saline solution. AS01$_{B-4}$ is a particularly preferred variant of the AS01 adjuvant, composed of immuno-enhancers QS-21 (a triterpene glycoside purified from the bark of *Quillaja saponaria*) and MPL (3-D Monophosphoryl lipid A), with DOPC/cholesterol liposomes, as vehicles for these immuno-enhancers, and sorbitol in a PBS solution. In particular, a single human dose of AS01$_{B-4}$ (0.5 mL) contains 50 µg of QS-21 and 50 µg of MPL. AS01$_{E-4}$ corresponds to a two-fold dilution of AS01B-4. i.e. it contains 25 µg of QS-21 and 25 µg of MPL per human dose.

In one embodiment, there is provided an immunogenic composition comprising a recombinant hepatitis B surface antigen (HBs), a truncated recombinant hepatitis B virus core antigen (HBc) and an adjuvant comprising MPL and QS-21. In one embodiment, the immunogenic composition comprises a recombinant HBs, a truncated recombinant HBc and an AS01 adjuvant. In a particular embodiment the immunogenic combination comprises a composition comprising a truncated recombinant HBc and a recombinant HBs in a ratio of 4:1 or more, and an AS01 adjuvant, for example AS01$_{B-4}$ or AS01$_{E-4}$.

In one embodiment, there is provided an immunogenic combination comprising:
a) a composition comprising a replication-defective chimpanzee adenoviral (ChAd) vector comprising a polynucleotide encoding a hepatitis B surface antigen (HBs) and a nucleic acid encoding a hepatitis B virus core antigen (HBc);
b) a composition comprising a Modified Vaccinia Virus Ankara (MVA) vector comprising a polynucleotide encoding a hepatitis B surface antigen (HBs) and a nucleic acid encoding a hepatitis B virus core antigen (HBc); and
c) a composition comprising a recombinant hepatitis B surface antigen (HBs), recombinant hepatitis B virus core antigen (HBc) and an adjuvant comprising MPL, QS-21 and liposomes composed of dioleoyl phosphatidylcholine (DOPC) and cholesterol.

In another embodiment, there is provided an immunogenic combination comprising:
a) a composition comprising a replication-defective chimpanzee adenoviral (ChAd) vector comprising a polynucleotide encoding a hepatitis B surface antigen (HBs) and a nucleic acid encoding a hepatitis B virus core antigen (HBc);
b) a composition comprising a Modified Vaccinia Virus Ankara (MVA) vector comprising a polynucleotide encoding a hepatitis B surface antigen (HBs) and a nucleic acid encoding a hepatitis B virus core antigen (HBc); and
c) a composition comprising a truncated recombinant HBc and a full length recombinant HBs in a ratio of 4:1 or more and an adjuvant comprising MPL, QS-21 and liposomes composed of dioleoyl phosphatidylcholine (DOPC) and cholesterol.

In another embodiment, there is provided an immunogenic combination comprising:
a) a composition comprising a replication-defective chimpanzee adenoviral (ChAd) vector comprising a polynucleotide encoding a hepatitis B surface antigen (HBs) and a nucleic acid encoding a hepatitis B virus core antigen (HBc);
b) a composition comprising a Modified Vaccinia Virus Ankara (MVA) vector comprising a polynucleotide encoding a hepatitis B surface antigen (HBs) and a nucleic acid encoding a hepatitis B virus core antigen (HBc); and
c) a composition comprising a truncated recombinant HBc and a full length recombinant HBs in a ratio of 4:1 or more and an AS01 adjuvant.

In another embodiment, there is provided an immunogenic combination comprising:
- a) a composition comprising a replication-defective chimpanzee adenoviral (ChAd) vector comprising a polynucleotide encoding a hepatitis B surface antigen (HBs) and a nucleic acid encoding a hepatitis B virus core antigen (HBc);
- b) a composition comprising a Modified Vaccinia Virus Ankara (MVA) vector comprising a polynucleotide encoding a hepatitis B surface antigen (HBs) and a nucleic acid encoding a hepatitis B virus core antigen (HBc); and
- c) a composition comprising a truncated recombinant HBc consisting of amino acids 1-149 of HBc (e.g. SEQ ID NO:2) and full length recombinant HBs (e.g. SEQ ID NO:1), in a 4:1 ratio and AS01B-4.

In one embodiment, there is provided an immunogenic combination comprising:
- a) a composition comprising a replication-defective ChAd155 vector comprising a polynucleotide encoding a hepatitis B surface antigen (HBs) and a nucleic acid encoding a hepatitis B virus core antigen (HBc);
- b) a composition comprising a Modified Vaccinia Virus Ankara (MVA) vector comprising a polynucleotide encoding a hepatitis B surface antigen (HBs) and a nucleic acid encoding a hepatitis B virus core antigen (HBc); and
- c) a composition comprising a recombinant hepatitis B surface antigen (HBs), recombinant hepatitis B virus core antigen (HBc) and an adjuvant comprising MPL, QS-21 and liposomes composed of dioleoyl phosphatidylcholine (DOPC) and cholesterol.

In another embodiment, there is provided an immunogenic combination comprising:
- a) a composition comprising a replication-defective ChAd155 vector comprising a polynucleotide encoding a HBs and a polynucleotide encoding a HBc separated by polynucleotide encoding a linker incorporating the 2A cleavage region of the foot and mouth disease virus;
- b) a composition comprising an MVA vector comprising a polynucleotide encoding a HBs and a polynucleotide encoding a HBc separated by polynucleotide encoding a linker incorporating the 2A cleavage region of the foot and mouth disease virus; and
- c) a composition comprising a truncated recombinant HBc and a full length recombinant HBs in a ratio of 4:1 or more and an adjuvant comprising MPL, QS-21 and liposomes composed of dioleoyl phosphatidylcholine (DOPC) and cholesterol.

In another embodiment, there is provided an immunogenic combination comprising:
- a) a composition comprising a replication-defective ChAd155 vector comprising a polynucleotide encoding a HBs and a polynucleotide encoding a human invariant chain (hIi) fused to the N-terminal of HBc;
- b) a composition comprising an MVA vector comprising a polynucleotide encoding a HBs and a polynucleotide encoding a HBc separated by polynucleotide encoding a linker incorporating the 2A cleavage region of the foot and mouth disease virus; and
- c) a composition comprising a truncated recombinant HBc and a full length recombinant HBs in a ratio of 4:1 or more and an AS01 adjuvant.

In certain embodiments, the vector insert of the ChAd vector of component a) of the immunogenic combination encodes HBc (e.g. SEQ ID NO:11 or an amino acid sequence at least 98% homologous thereto) and HBs (e.g. SEQ ID NO:1 or an amino acid sequence at least 98% homologous thereto), separated by a sequence encoding a spacer which incorporates the 2A cleaving region of the foot and mouth disease virus (e.g. SEQ ID NO:3 or an amino acid sequence at least 98% homologous thereto). In certain embodiments, HBc (e.g. SEQ ID NO:11 or an amino acid sequence at least 98% homologous thereto) is fused to hIi (e.g. SEQ ID NO:7 or an amino acid sequence at least 98% homologous thereto or SEQ ID NO:12 or an amino acid sequence at least 98% homologous thereto). For example, HBc (e.g. SEQ ID NO:11) is fused to hIi (e.g. SEQ ID NO:7), or HBc (e.g. SEQ ID NO:11) is fused to hIi (e.g. SEQ ID NO:12).

In certain embodiments, the vector insert of the MVA vector of component b) of the immunogenic combination encodes HBc (e.g. SEQ ID NO:11 or an amino acid sequence at least 98% homologous thereto) and HBs (e.g. SEQ ID NO:1 or an amino acid sequence at least 98% homologous thereto), separated by a sequence encoding a spacer which incorporates the 2A cleaving region of the foot and mouth disease virus (e.g. SEQ ID NO:3 or an amino acid sequence at least 98% homologous thereto). For example, the vector insert encodes HBc (e.g. SEQ ID NO:11) and HBs (e.g. SEQ ID NO:1), separated by a sequence encoding a spacer which incorporates the 2A cleaving region of the foot and mouth disease virus (e.g. SEQ ID NO:3).

In another embodiment, there is provided an immunogenic combination comprising:
- a) a composition comprising a replication-defective ChAd155 vector a polynucleotide vector insert encoding the amino acid sequence of SEQ ID NO:9 or a polynucleotide vector insert encoding the amino acid sequence of SEQ ID NO:15;
- b) a composition comprising an MVA vector comprising a polynucleotide vector insert encoding the amino acid sequence of SEQ ID NO:5; and
- c) a composition comprising a truncated recombinant HBc consisting of amino acids 1-149 of HBc (e.g. SEQ ID NO:2) and full length recombinant HBs (e.g. SEQ ID NO:1) in a 4:1 ratio, and $AS01_{B-4}$.

In another embodiment, there is provided an immunogenic combination comprising:
- a) a composition comprising a replication-defective ChAd155 vector a polynucleotide vector insert comprising SEQ ID NO:10 or a polynucleotide vector insert comprising SEQ ID NO:14;
- b) a composition comprising an MVA vector comprising a polynucleotide vector insert comprising SEQ ID NO.6; and
- c) a composition comprising a truncated recombinant HBc consisting of amino acids 1-149 of HBc (e.g. SEQ ID NO:2) and full length recombinant HBs (e.g. SEQ ID NO:1) in a 4:1 ratio, and $AS01_{B-4}$.

Administration

In certain embodiments, the disclosed immunogenic compositions and immunogenic combinations are administered via intranasal, intramuscular, subcutaneous, intradermal, or topical routes. Preferably, administration is via an intramuscular route.

An intranasal administration is the administration of the immunogenic composition to the mucosa of the complete respiratory tract including the lung. More particularly, the composition is administered to the mucosa of the nose. In one embodiment, an intranasal administration is achieved by means of spray or aerosol. Intramuscular administration refers to the injection of a composition into any muscle of an individual. Exemplary intramuscular injections are administered into the deltoid, vastus lateralis or the ventrogluteal and dorsogluteal areas. Preferably, administration is into the deltoid. Subcutaneous administration refers to the injection of the composition into the hypodermis. Intradermal administration refers to the injection of a composition into the dermis between the layers of the skin. Topical administration is the administration of the composition to any part of the skin or mucosa without penetrating the skin with a needle or a comparable device. The composition may be administered topically to the mucosa of the mouth, nose, genital region and/or rectum. Topical administration includes administration means such as sublingual and/or buccal administration. Sublingual administration is the administration of the composition under the tongue (for example, using an oral thin film (OTF)). Buccal administration is the administration of the vector via the buccal mucosa of the cheek.

The immunogenic compositions and combinations disclosed herein take may find use in a prime-boost immunisation regimen. Accordingly, herein disclosed are compositions for use in a method of treatment of CHB which is a prime-boost immunisation method. In many cases, a single administration of an immunogenic composition is not sufficient to generate the number of long-lasting immune cells which is required for effective protection or for therapeutically treating a disease. Consequently, repeated challenge with a biological preparation specific for a specific pathogen or disease may be required in order to establish lasting and protective immunity against said pathogen or disease or to treat or functionally cure a given disease. An administration regimen comprising the repeated administration of an immunogenic composition or vaccine directed against the same pathogen or disease is referred to as a "prime-boost regimen". In one embodiment, a prime-boost regimen involves at least two administrations of an immunogenic composition directed against hepatitis B. The first administration of the immunogenic composition is referred to as "priming" and any subsequent administration of the same immunogenic composition, or an immunogenic composition directed against the same pathogen, is referred to as "boosting". It is to be understood that 2, 3, 4 or even 5 administrations for boosting the immune response are also contemplated. The period of time between prime and boost is, optionally, 1 week, 2 weeks, 4 weeks, 6 weeks 8 weeks or 12 weeks. More particularly, it is 4 weeks or 8 weeks. If more than one boost is performed, the subsequent boost is administered 1 week, 2 weeks, 4 weeks, 6 weeks, 8 weeks or 12 weeks, 6 months or 12 months after the preceding boost. For example, the interval between any two boosts may be 4 weeks or 8 weeks.

The immunogenic compositions disclosed herein may be administered in a therapeutic regimen which involves administration of a further immunogenic component, each formulated in different compositions (e.g. an immunogenic combination). The compositions are favourably administered co-locationally at or near the same site. For example, the components can be administered intramuscularly, to the same side or extremity ("co-lateral" administration) or to opposite sides or extremities ("contra-lateral" administration). For example, in contra-lateral administration, a first composition may be administered to the left deltoid muscle and a second composition may be administered, sequentially or concomitantly, to the right deltoid muscle. Alternatively, in co-lateral administration, a first composition may be administered to the left deltoid muscle and a second composition may be administered, sequentially or concomitantly, also to the left deltoid muscle.

General Manufacturing Processes

ChAd155-hIi-HBV

The DNA fragment inserted as the transgene in the recombinant replication-defective simian (chimpanzee-derived) adenovirus group C vector ChAd155 is derived from two HBV protein antigens, the core nucleocapsid protein antigen HBc and the small surface antigen HBs, separated by the self-cleaving 2A region of the foot-and-mouth disease virus (FMDV) [Donnelly et al. 2001]. The 2A region of FMDV allows processing of the HBc-HBs fusion into separate protein antigens. In addition, the N-terminal part of the gene encoding the HBc protein has been fused to the gene encoding the human Major Histocompatibility Complex (MHC) class II-associated invariant chain p35 isoform (hIi). A schematic representation of the hIi-HBV transgene sequence is provided in (FIG. 22).

The 2A region (18 amino acids) has been supplemented with a spacer of 6 amino acids at its N-terminus; spacers of this nature have been reported to increase the efficiency of 2A mediated cleavage. The region 2A-mediated protease cleavage occurs at the C-terminus of 2A just ahead of the last proline in the 2A amino acid sequence. The proline remains at the N-terminus of the HBs protein, while the 23 amino acids preceding the proline cleavage site remain with the hIi-HBc-2A polypeptide.

The expression of the transgene thereby results, following protease processing, in the production of two separate polypeptides: hIi-HBc-spacer-2A and HBs. For brevity the hIi-HBc-spacer-2A polypeptide is referred to as the hIi-HBc protein. When expressed in cell culture, the hIi-HBc antigen is detected in the cell culture supernatant whilst the HBs protein is detected in the intracellular fraction.

The expression cassette encoding the antigenic proteins, operatively linked to regulatory components in a manner which permits expression in a host cell, is assembled into the ChAd155 vector plasmid construct as previously described (see WO2016/198621 which is incorporated by reference for the purpose of disclosing ChAd155 vector sequences and methods) to give ChAd155-hIi-HBV. The hIi-HBV transgene is under the transcriptional control of human cytomegalovirus (hCMV) promoter and bovine growth hormone poly-adenylation signal (BGH pA). The expression cassette encodes the HBs, HBc and hIi amino acid sequences, in which the hIi sequence is fused to the HBc N-terminal of HBc and the HBs and HBc sequences are separated by a spacer which incorporates a 2A cleaving region of the foot and mouth disease virus, for processing of the HBc and HBs into separate proteins.

To generate recombinant ChAd155 adenoviruses which are replication deficient, the function of the deleted gene region required for replication and infectivity of the adenovirus must be supplied to the recombinant virus by a helper virus or cell line, i.e., a complementation or packaging cell line. A particularly suitable complementation cell line is the Procell92 cell line. The Procell92 cell line is based on HEK 293 cells which express adenoviral E1 genes, transfected with the Tet repressor under control of the human phosphoglycerate kinase-1 (PGK) promoter, and the G418-resistance gene (Vitelli et al. *PLOS One* (2013) 8(e55435):1-9). Procell92.S is adapted for growth in suspension conditions and is useful for producing adenoviral vectors expressing toxic proteins.

Production of the ChAd155-hIi-HBV Drug Substance:

The manufacturing of the ChAd155-hIi-HBV viral particles (Drug Substance) involves culture of Procell-92.S cells at 5e5 cell/ml cell density at infection. The cells are then infected with ChAd155-hIi-HBV Master Viral Seed (MVS) using a multiplicity of infection of 200 vp/cell. The ChAd155-hIi-HBV virus harvest is purified following cell lysis, lysate clarification and concentration (filtration steps) by a multi-step process which includes anion exchange chromatography.

Vaccine Formulation and Filling

The purified ChAd155-hIi-HBV bulk Drug Substance is subsequently processed as follows:

Dilution of the purified ChAd155-hIi-HBV Drug Substance in the formulation buffer.

Sterile filtration.

Filling of the final containers.

The ChAd155-hIi-HBV vaccine is a liquid formulation contained in vials. The formulation buffer includes Tris (10 mM), L-Histidine (10 mM), NaCl (75 mM), MgCl (1 mM) and EDTA (0.1 mM) with sucrose (5% w/v), polysorbate-80 (0.02% w/v) and ethanol (0.5% w/v), adjusted to pH 7.4 with HCl (water for injection to final volume).

MVA-HBV:

MVA-HBV is a recombinant modified vaccinia virus Ankara (MVA) carrying two different proteins of HBV: Core and S proteins, separated by 2A peptide. The MVA-HBV construct was generated from the MVA-Red vector system [Di Lullo et al. 2010], derived from the MVA virus seed batch from attenuation passage 571 (termed MVA-571) that was described by Professor Anton Mayr [Mayr, A. et al. 1978].

The MVA-HBV transgene encodes the core nucleocapsid protein HBc and the small surface antigen HBs of HBV. The HBc-HBs sequence is separated by the self-cleaving 2A region of the foot-and-mouth disease virus that allows processing of the fusion protein into separate HBc and HBs antigens as described above for the adenoviral vector. A schematic representation of the transgene is provided in FIG. 21.

The expression of the transgene, following protease processing, results in the production of two separate polypeptides: HBc-spacer-2A and HBs. For brevity the HBc-spacer-2A polypeptide is referred to as the HBc protein.

The expression cassette was subcloned into the MVA shuttle vector p94-elisaRen generating the transfer vector p94-HBV. p94-HBV contains the antigen expression cassette under the vaccinia P7.5 early/late promoter control and flanked by FlankIII-2 region and FlankIII-1 regions to allow insertion in the del III of MVA by homologous recombination.

The production of the recombinant virus was based on two events of in vivo recombination in CEF cells Briefly, primary chick embryo fibroblasts (CEF) were infected with MVA-Red and then transfected with p94-HBV carrying the antigen transgene (as well as the EGFP marker gene under control of the synthetic promoter sP). The first recombination event occurs between homologous sequences (FlankIII-1 and -2 regions) present in both the MVA-Red genome and the transfer vector p94-HBV and results in replacement of the Hcred protein gene with transgene/eGFP cassette. Infected cells containing MVA-Green intermediate are isolated by FACS sorting and used to infect fresh CEF. The intermediate recombinant MVA, resulting from first recombination, carries both the transgene and the eGFP cassette but is instable due to the presence of repeated Z regions.

Thus, a spontaneous second recombination event involving Z regions occurs and removes the eGFP cassette. The resulting recombinant MVA is colourless and carries the transgene cassette.

Finally, markerless recombinant virus (MVA-HBV) infected cells were sorted by FACS, MVA-HBV was cloned by terminal dilution, and expanded in CEF by conventional methods.

Production of the MVA-HBV Drug Substance

The MVA-HBV viral particles (Drug Substance) is manufactured in primary cell cultures of chicken embryo fibroblast (CEF) cells to a cell density between 1E6 and 2E6 cell/ml, and then infected with MVA-HBV Master Viral Seed (MVS) at a multiplicity of infection between 0.01 and 0.5 PFU/cell. The MVA-HBV virus harvest is purified by a multi-step process based on pelleting by centrifugation, resuspension and fractional gradient centrifugation steps.

Vaccine Formulation and Filling

The purified MVA-HBV bulk Drug Substance is subsequently processed as follows:

Dilution of the purified MVA-HBV DS in the formulation buffer.

Filling of the final containers.

The MVA-HBV vaccine is a liquid formulation contained in vials. The formulation buffer includes Tris (hydroxymethyl) amino methane pH7.7 (10 mM), NaCl (140 mM), and water for injection to final volume.

HBs-HBc recombinant protein mix:

Production of HBc Drug Substance

The HBc recombinant protein (Drug Substance) manufacturing process consists of inoculating a pre-culture flask using the recombinant *E. coli* working seed, followed by a fermentation process and a multi-step purification process including harvesting, extraction, clarification and multiple chromatography and filtration steps.

Production of the HBs Drug Substance

The HBs recombinant protein (Drug Substance) manufacturing process consists of inoculating a pre-culture flask using the recombinant *S. cerevisiae* working seed, followed by a fermentation process and a multi-step purification process including harvesting, extraction, clarification and multiple chromatography and filtration steps.

Vaccine Formulation and Filling

The purified HBs Drug Substance and HBc Drug Substance is diluted in the formulation buffer including sucrose as cryoprotectant and poloxamer as surfactant, filled and lyophilized in 4 mL clear glass vial.

EXAMPLES

Objectives of the Non-Clinical Development

Strong and functional $CD8^+$ and $CD4^+$ T cell responses, particularly to the HBcAg, have been associated with HBV clearance and resolving infection [Boni, 2012; Li, 2011; Liang, 2011; Lau, 2002; Bertoletti, 2012]. Furthermore, anti-S antibodies prevent HBV spread to non-infected hepatocytes and may be key to control post-treatment rebound of HBV replication [Rehermann 2005; Neumann 2010]. The proposed vaccination regimen includes a heterologous prime-boost schedule with two viral vectored vaccines (ChAd155-hIi-HBV and MVA-HBV) coding for the hepatitis B core (HBc) and the hepatitis B surface (HBs) antigens in order to induce a strong $CD8^+$ T-cell response, together with sequential or concomitant administration of $AS01_{B-4}$-adjuvanted HBc-HBs proteins in order to induce strong antigen-specific $CD4^+$ T-cell and antibody responses in CHB patients. This vaccine-induced immune response, should ultimately translate to a substantial decrease in HBsAg concentration or HBsAg loss (i.e. HBsAg concentration below detectable level) considered as a marker for complete and durable control of HBV infection.

The main objectives of the non-clinical development were:
- To demonstrate the immunogenicity in naïve and HBV-tolerant mice of the investigational vaccine components e.g. ChAd155-hIi-HBV, MVA-HBV and HBc-HBs/AS01$_{B-4}$ to guide the choice of the vector constructs, the inclusion of hIi, the composition of the protein formulation including Adjuvant System selection, and the schedule of immunization.
- To demonstrate the safety of the full vaccine regimen in HBV tolerant mice (non-GLP study) and in a repeated dose GLP toxicity study conducted in NZW rabbits
- To document the biodistribution of the vectors in vaccinated animals (GLP studies).

Non-clinical Strategy and Rationale for Choice of the Animal Models

An immunogenicity package was first generated in healthy mice, to guide the choice of the vector constructs, the protein formulation including Adjuvant System selection, and the schedule of immunization.

Most of the preclinical experiments were conducted in in-bred CB6F1 (hybrid of C57Bl/6 and BALB/c mice) mice, a model used previously to evaluate T-cell responses elicited by AS01 adjuvanted candidate vaccines and adenoviral vectors [Lorin, 2015] to support the choice of the vector constructs, the protein formulation including Adjuvant System selection, and the schedule of immunization.

HLA.A2/DR1 mice (transgenic for the human HLA-A2 and HLA-DR1 molecules) were used to evaluate the ability of the candidate vaccine to induce HBc-specific CD8$^+$ T-cell responses, as no such responses were detected against this antigen in in-bred CB6F1 mice. This is most likely due to the absence of the H2-K$^b$ MHC-I-restricted immuno-dominant epitope (MGLKFRQL) in the HBc sequence of the investigational vaccine, which is based on the sequence of HBV genotype A/subtype adw, with a one amino-acid difference where an Isoleucine (I) replaces the Phenylalanine (F) in the epitope (MGLKIRQL), as reported by Riedl et al [Riedl, 2014]. HBV specific CD4$^+$ T-cells and antibodies were evaluated in the same HLA.A2/DR1 mice.

The animal models available to assess the efficacy of a therapeutic vaccine are limited as HBV naturally infects only chimpanzees and humans. Mouse models have been developed where the whole HBV genome is expressed either through the integration of the viral genome in the host genome (HBV transgenic mice) or through infection with replicative HBV DNA, or vectors expressing the HBV genome. Although these do not reproduce the chronic HBV pathogenesis, viral replicative intermediates and proteins can be detected in the liver, and immune tolerance is observed.

The AAV2/8-HBV-transduced HLA.A2/DR1 murine model recapitulates virological and immunological characteristics of chronic HBV infection and was selected [Dion, 2013; Martin, 2015]
- to demonstrate that the vaccine regimen can overcome the tolerance to HBs and HBc antigens.
- to evaluate the impact of liver infiltrating HBc-specific CD8+ T-cells, potentially targeting hepatocytes expressing the HBcAg, on the histology of the liver (Hematoxylin-eosin [H&E] staining) and ALT/AST levels.

Finally, standard animal models for bio-distribution (Sprague-Dawley rats) and toxicology studies (NZW rabbits) have been selected to evaluate the candidate vaccines because, although they are not models of infection, they are capable of mounting pharmacologically-relevant immune responses to vector-expressed and recombinant proteins, and are well-accepted species for toxicity testing of vaccines. These species have also been previously used in the toxicology testing programs for AS01$_B$ adjuvant and its immuno-enhancers, MPL and QS-21.

Non-Clinical Pharmacology

A number of preclinical studies were conducted to demonstrate immunogenicity in naive and HBV-tolerant animals of the investigational vaccine components e.g. ChAd155-hIi-HBV, MVA-HBV and HBc-HBs/AS01$_{B-4}$, after intramuscular administration. The antigen-specific immunogenicity profile was first evaluated separately for the viral vectors (ChAd155-hIi-HBV and MVA-HBV) and the HBV recombinant protein adjuvanted investigational vaccine (HBc-HBs/AS01$_{B-4}$). The immunogenicity and safety profile of the full vaccine regimen as intended in the FTiH (first time in humans) was evaluated in a second phase.

Materials

Doses of AS01 Adjuvant System Used in the Non-Clinical Immunogenicity Studies

The AS01$_{B-4}$ Adjuvant System is composed of immuno-enhancers QS-21 (a triterpene glycoside purified from the bark of *Quillaja saponaria*) and MPL (3-D Monophosphoryl lipid A), with liposomes as vehicles for these immuno-enhancers and sorbitol. In particular, a single human dose of AS01$_{B-4}$ (0.5 mL) contains 50 μg of QS-21 and 50 μg of MPL. $\frac{1}{10}^{th}$ of a human dose i.e. 50 μl is the volume injected in mice (corresponding to 5 μg QS-21 and MPL).

The AS01$_{E-4}$ Adjuvant System corresponds to a two-fold dilution of the AS01$_{B-4}$ dilution. $\frac{1}{10}^{th}$ of a human dose i.e. 50 μl is the volume injected in mice (corresponding to 2.5 μg QS-21 and MPL).

Cellular Immune Response—Intracellular Cytokine Staining (ICS)

Fresh pools of peripheral blood leukocytes (PBLs), splenocytes or liver infiltrating lymphocytes collected at different time points, were stimulated ex vivo for 6 hours with pools of 15-mers, overlapping of 11aa, covering the HBc or HBs sequence. The HBc and HBs-specific cellular responses were evaluated by ICS measuring the amount of CD4$^+$ or CD8$^+$ T-cells expressing IFN-γ and/or IL-2 and/or tumor necrosis factor (TNF)-α. The technical acceptance criteria to take into account ICS results include the minimal number of acquired CD8$^+$ T or CD4$^+$ T cells being >3000 events. Alternatively, IFN-γ-ELISpot was performed after restimulation of splenocytes with the same peptides as for the ICS.

Humoral Immune Response—Enzyme-Linked Immunosorbent Assay (ELISA)

HBc- and HBs-specific antibody responses were measured by ELISA on sera from immunized mice at different time points. Briefly, 96-well plates were coated with HBc or HBs antigens. Individual serum samples were then added in serial dilutions and incubated for 2 hours. A biotinylated anti-mouse F(ab)'2 fragment was then added and the antigen-antibody complex was revealed by incubation with a streptavidin horseradish peroxidase complex and a peroxidase substrate ortho-phenylenediamine dihydrochlorid/$H_2O_2$. For each time point and each antigen (HBc, HBs), an analysis of variance (ANOVA) model was fitted on log 10 titres including group, study and interaction as fixed effects and using a heterogeneous variance model (identical variances were not assumed between groups). This model was used to estimate geometric means (and their 95% CIs) as well as the geometric mean ratios and their 95% CIs. As no pre-defined criteria were set, the analysis is descriptive and 95% CIs of ratios between groups were computed without adjustment for multiplicity.

ALT/AST Measure

The levels of ALT and AST in mouse sera were quantified using the following commercial kits:
Alanine Aminotransferase Activity Assay Kit Sigma Aldrich Cat # MAK052
Aspartate Aminotransferase Activity Assay Kit Sigma Aldrich Cat # MAK055

Serum HBs Antigen Quantification

The circulating HBs antigen in mouse sera was quantified using the Monolisa Anti-HBs PLUS from BIO-RAD (cat # 72566) and an international standard (Abbott Diagnostics).

Histopathology Analysis

The livers (one lobe per liver) were collected and preserved in 10% formaldehyde fixative. All samples for microscopic examination were trimmed based on RITA guidelines [Ruehl-Fehlert, 2003; Kittel 2004; Morawietz 2004], embedded in paraffin wax, sectioned at a thickness of approximately 4 microns and stained with H&E. Grading of histological activity (necro-inflammatory lesions) and fibrosis was performed according to the METAVIR scoring system [Bedossa, 1996; Mohamadnejad, 2010; Rammeh, 2014]. Grading of inflammatory cell foci was done according to the Desmet score, as described by Buchmann eta/ [Buchmann, 2013].

Statistical analysis performed in each study is detailed in the sections pertaining to each individual study.

Example 1—Evaluation of ChAd155-HBV (with and without hIi) Prime and MVA-HBV Boost in HLA.A2/DR1 Transgenic Mouse Model Objectives The main objective of this experiment was to determine whether priming with one dose of ChAd155-HBV (with or without hIi) followed by a booster dose of MVA-HBV, was able to induce a strong $CD8^+$ T cell response against HBc in HLA.A2/DR1 mice which are transgenic for human MHC-I/II molecules. In addition, a head-to-head comparison between ChAd155-HBV with and without hIi was performed to investigate the potential of the hIi sequence to further increase HBc-specific $CD8^+$ T-cell responses, as previously reported for other antigens [Spencer, 2014; Capone, 2014]. HBs-specific $CD8^+$ T-cell responses as well as HBc- and HBs-specific $CD4^+$ T-cell and antibody responses were also evaluated.

Study Design

HLA.A2/DR1 mice (11 mice per group) were immunized with $10^8$ vp of ChAd155-HBV (with and without hIi) through intramuscular route at Day 0 and boosted with $10^7$ pfu of MVA-HBV (without hIi) at Day 28 (Table 1). Mice were sacrificed at 14 days post first immunization (14 dpI) (prime) or 7 days post second immunization (7 dpII) (boost) to determine the HBc- and HBs-specific humoral and cellular immune responses in serum and spleen, respectively.

TABLE 1

Study design of ChAd155-HBV (with and without hIi) prime/MVA-HBV (without hIi) boost experiment in HLA.A2/DR1 mice.

| Groups | Prime | Boost | Sacrifice |
|---|---|---|---|
| 1 | $10^8$ vp ChAd155-HBV (Day 0) | $10^7$ pfu MVA-HBV (Day 28) | 14 dpI and 7 dpII |
| 2 | $10^8$ vp ChAd155-hIi-HBV (Day 0) | $10^7$ pfu MVA-HBV (Day 28) | 14 dpI and 7 dpII |
| 3 | NaCl (Day 0) | NaCl (Day 28) | 14 dpI and 7 dpII |

Statistical Analysis

An ANOVA model was fitted on log 10 $CD8^+$ T-cell frequencies including 2 groups (with or without hIi) and experiments (results of 3 experiments post-prime and results of 2 experiments post-boost) as fixed parameters and using a heterogeneous variance model. This model was used to estimate geometric means (and their 95% CIs) as well as the geometric mean ratios and their 95% CIs.

Results

HBc- and HBs-Specific T-Cell Response

Both ChAd155-HBV and ChAd155-hIi-HBV vectors induced an HBc-specific $CD8^+$ T-cell response (FIG. 1A). Presence of hIi tends to induce a higher $CD8^+$ T-cell response against the HBc antigen. MVA-HBV boost of mice immunized with ChAd155-hIi-HBV induced a 3 fold increase in HBc-specific $CD8^+$ T-cell responses while no increase was observed for the ChAd155-HBV group.

Both vectors induced HBs-specific $CD8^+$ T-cell responses and the MVA-HBV booster effect was more pronounced in mice primed with the ChAd155-HBV construct (FIG. 1B).

HBc- and HBs-specific $CD4^+$ T-cell responses were low (data not shown).

The results of this experiment were consistent with those of two other similar independent experiments (data not shown). Although each independent study was not statistically powered to compare groups due to limitations related to the availability of animals, a meta-analysis over the 3 studies was conducted to compare the HBc-specific $CD8^+$ T-cell responses induced by ChAd155-HBV versus ChAd155-hIi-HBV, after priming and after MVA-HBV boost.

The statistical analysis showed that the HBc-specific $CD8^+$ T-cell responses induced by the prime-boost regimen using the ChAd155-hIi-HBV construct were significantly higher than those elicited by the prime-boost regimen using ChAd155-HBV, after prime and after the MVA-HBV boost, supporting the use of the human invariant chain sequence fused to the HBc sequence.
a. 14 day post dose I, the geometric mean ratio (hIi/no hIi) was estimated to 3.27 (95% CI: 1.57-6.79)
b. 7 day post dose II, the geometric mean ratio (hIi/no hIi) was estimated to 6.25 (95% CI: 2.11-18.51)

HBc and HBs-Specific Antibody Responses

Immunization with ChAd155-HBV but not ChAd155-hIi-HBV induced HBc-specific antibodies. After the MVA-HBV booster, the anti-HBc antibody response was comparable between groups primed with ChAd155-HBV or ChAd155-hIi-HBV (FIG. 2). No HBs-specific antibody response was detected (data not shown).

Conclusion

ChAd155-hIi-HBV induced the highest $CD8^+$ T-cell response against HBc when compared to ChAd155-HBV and this response was further increased after MVA-HBV boost.

Example 2—HBc-HBs/AS01$_{B-4}$ Immunogenicity Study in Inbred Mice (CB6F1)

Objectives

The main objective of this immunogenicity study was to determine whether HBc and HBs proteins were able to induce both HBc- and HBs-specific humoral and T cell responses when co-formulated in AS01$_{B-4}$.

Study Design

CB6F1 mice (30 mice per group), 6 to 8 weeks old, were immunized three times intra-muscularly at Day 0, 14 and 28 with HBc, HBs or HBc-HBs formulated in 50 µl of AS01$_{B-4}$ (listed in Table 2 below). The HBc- and HBs-specific T cell responses were measured on fresh PBLs 7 days post-second and third dose, and the anti-HBs and anti-HBc antibody responses were measured at 14 days post second and third dose.

TABLE 2

Treatment groups

| Groups | Antigen |
| --- | --- |
| 1 | 1 µg HBc/AS01$_{B-4}$ (HBc/AS01$_{B-4}$) |
| 2 | 1 µg HBs/AS01$_{B-4}$ (HBs/AS01$_{B-4}$) |
| 3 | 1 µg HBc + 1 µg HBs/AS01$_{B-4}$ (HBc-HBs/AS01$_{B-4}$) |
| 4 | NaCl |

Statistical Analysis

The statistical analysis was done using an ANOVA on the log 10 values with 1 factor (group) using a heterogeneous variance model, i.e. identical variances were not assumed for the different levels of the factor. This analysis has been done by timepoint (Post $2^{nd}$ and Post $3^{rd}$ immunization), by T cell response (CD4$^+$ and CD8$^+$ T cells) and antigen specificity (HBs and HBc). Estimates of the geometric mean ratios between groups and their 95% confidence intervals (CI) were obtained using back-transformation on log 10 values. Adjustment for multiplicity was performed using Tukey's method. Multiplicity adjusted 95% confidence intervals were provided.

Results

HBc and HBs-Specific T-cell Responses

Immunization of mice with HBc/AS01$_{B-4}$, HBs/AS01$_{B-4}$ or HBc-HBs/AS01$_{B-4}$ induced a potent CD4$^+$ T-cell response against both antigens (FIG. 3A and FIG. 3B). The magnitude of the HBc-specific CD4$^+$ T-cell response was significantly lower (2.3 fold, P-value=0.0468) for the HBc-HBs/AS01$_{B-4}$ formulation compared to the HBc/AS01$_{B-4}$, suggesting an interference of HBs on HBc-specific T-cell responses. Nevertheless, the level of HBc-specific CD4$^+$ T-cells was still considered as strong, well above that in the control group. No such interference was observed on the level of HBs-specific CD4$^+$ T-cell response.

The HBs/AS01$_{B-4}$ or HBc-HBs/AS01$_{B-4}$ formulations induced a strong HBs-specific CD8$^+$ T-cell response (FIG. 4). None of the vaccine candidates induced a detectable HBc-specific CD8$^+$ T-cell response, (data not shown) as expected with this mouse model because of the absence in the HBc sequence of our vaccine candidate of the H2-K$^b$ MHC-I restricted immuno-dominant epitope—MGLKFRQL—as reported by others [Riedl, 2014].

HBc and HBs-Specific Antibody Response

High levels of anti-HBc and/or anti-HBs antibodies were induced by each of the three formulations (see FIG. 5A and FIG. 5B). A significantly lower level of anti-HBc antibody response was observed in HBc-HBs/AS01$_{B-4}$ formulation compared to HBc/AS01$_{B-4}$ (2.35 fold, P<0.0001). In contrast, the presence of HBc in the HBc-HBs/AS01$_{B-4}$ combination did not negatively impact the anti-HBs antibody response (FIG. 5A and FIG. 5B).

Conclusion

All formulations (HBs/AS01$_{B-4}$, HBc/AS01$_{B-4}$ and HBc-HBs/AS01$_{B-4}$) were immunogenic and induced both cellular and humoral responses against both antigens, except for HBc-specific CD8$^+$ T cell responses (as expected in this model). The anti-HBc response elicited by the HBc-HBs/AS01$_{B-4}$ formulation was lower than the one elicited by HBc/AS01$_{B-4}$, suggesting interference linked to the presence of HBs in this mouse model. This interference was further evaluated; see Example 7 where a ratio 4 to 1 of HBc to HBs was able to restore the anti-HBc immune response (antibody and specific CD4$^+$ T-cells) without impacting the anti-HBs antibody response. This formulation, HBc-HBs 4-1/AS01$_{B-4}$ was selected for subsequent nonclinical immunogenicity studies with adjuvanted protein formulations.

Example 3—Adjuvant Comparison Experiment in Inbred Mice (CB6F1)

Objectives

The main purpose of this experiment was to compare the ability of HBc and HBs antigens, at a ratio of 4 to 1 formulated with different adjuvants (Alum, AS01$_{B-4}$ or AS01$_{E-4}$) or without adjuvant, to induce a strong CD4$^+$ T-cell and humoral response against both antigens.

Study Design

CB6F1 mice (35 mice for Groups 1-4 and 25 mice for Group 5), 6 to 8 weeks old, were immunized three times intra-muscularly at Days 0, 14 and 28 with HBc-HBs antigens (4 µg-1 µg) formulated with alum, AS01$_{B-4}$ or AS01$_{E-4}$ (listed in Table 3 below). The AS01$_{E-4}$ Adjuvant System contains half of the quantities of the immuno-enhancers QS-21 and MPL compared to AS01$_{B-4}$. The HBc- and HBs-specific T cell responses were measured on fresh PBLs 7 days post-second and third dose, after ex vivo 6-hour re-stimulation with pools of peptides and the anti-HBs and anti-HBc antibody responses were measured by ELISA at 14 days post second and third dose.

TABLE 3

Treatment groups

| Groups | Antigen |
| --- | --- |
| 1 | HBc-HBs 4-1 |
| 2 | HBc-HBs 4-1/Alum |
| 3 | HBc-HBs 4-1/AS01$_{B-4}$ |
| 4 | HBc-HBs 4-1/AS01$_{E-4}$ |
| 5 | NaCl |

Statistical Analysis

For the statistical analysis, an ANOVA model was fitted on log 2 T cell frequencies and on log 10 antibody titers including group as fixed effect and using a heterogeneous variance model (identical variances were not assumed between groups, NaCl group being excluded from the analysis). This model was used to estimate geometric means (and their 95% CIs) as well as the geometric mean ratios (AS01$_B$ over the 3 other groups) and their 95% CIs. A Dunnett's adjustment was applied for HBc- and HBs-specific CD4$^+$ T cell frequencies (primary endpoint) and anti-HBs antibody titers (secondary endpoint) measured at 14 days post-third dose. For other responses/time points, the analyses are descriptive and no adjustment was applied.

Results

HBc- and HBs-Specific T-cell Responses

AS01-adjuvanted formulations elicited significantly higher HBc specific CD4+ T-cell responses compared to alum-adjuvanted and non-adjuvanted formulations (FIG. 6B). No statistically significant difference was observed between $AS01_{B-4}$ and $AS01_{E-4}$ formulations. As previously observed in CB6F1 mice, HBc-specific CD8+ T-cell response was undetectable whatever the formulation tested (data not shown).

The HBs-specific CD4+ (FIG. 6A) and CD8+ (FIG. 6C) T-cell responses were significantly higher for the AS01-adjuvanted formulations compared to alum-adjuvanted and non-adjuvanted formulations. No statistically significant difference was observed between $AS01_{B-4}$ and $AS01_{E-4}$ formulations.

HBc and HBs-Specific Antibody Responses

AS01-adjuvanted formulations elicited significantly higher anti-HBc and anti-HBs total IgG responses compared to alum-adjuvanted and non-adjuvanted formulations (FIG. 7A and FIG. 7B). Total IgG antibody responses elicited by the $AS01_{B-4}$ and the $AS01_{E-4}$-adjuvanted formulations were not statistically different.

Conclusion

Overall, the AS01 adjuvant system ($AS01_{E-4}$ or $AS01_{B-4}$) induced the highest humoral and cellular responses against HBc and HBs, as compared to Alum-based or non-adjuvanted formulations in CB6F1 mice.

Example 4—Immunogenicity Evaluation of ChAd155-hIi-HBV/MVA-HBV/HBs-HBc/$AS01_{B-4}$ Vaccine Regimens in HLA.A2/DR1 Transgenic Mice Objectives The objective of this study was to evaluate the immunogenicity of different vaccine regimens consisting of a prime/boost with ChAd155-hIi-HBV/MVA-HBV viral vectors followed by or co-administered with two doses of HBc-HBs 4-1/$AS01_{B-4}$ proteins.

Study Design

The first group of mice (N=16) was immunized at Day 0 with ChAd155-hIi-HBV followed by MVA-HBV 28 days later. Two doses of HBc-HBs 4-1 μg/$AS01_{B-4}$ were injected 14 days apart after this prime/boost viral vector regimen (Table 4). The second group of mice (N=16) was immunized at Day 0 with ChAd155-hIi-HBV and HBc-HBs 4-1/$AS01_{B-4}$ followed 28 days later by a boost with MVA-HBV co-administered with HBc-HBs 4-1/$AS01_B$. Two subsequent co-immunizations of MVA-HBV and HBc-HBs 4-1/$AS01_B$ were performed 14 days apart (Table 4). The third group of mice (N=8) was injected with NaCl as negative control. Mice were sacrificed at 7 days post second (7 dpII) and post fourth immunization (7 dpIV) to determine the HBc- and HBs-specific humoral (sera) and cellular immune responses (on splenocytes and liver infiltrating lymphocytes).

This study was descriptive and no statistical sample size justification and analysis were performed.

TABLE 4

| Treatment groups | | | | | |
|---|---|---|---|---|---|
| Groups | Day 0 | Day 28 | Day 42 | Day 56 | Sacrifice |
| 1 | $10^8$ vp ChAd155-hIi-HBV | $10^7$ pfu MVA-HBV | HBc-HBs 4-1/$AS01_{B-4}$ | HBc-HBs 4-1/$AS01_{B-4}$ | 7 dpII and 7 dpIV |
| 2 | $10^8$ vp ChAd155-hIi-HBV + HBc-HBs 4-1/ $AS01_{B-4}$ | $10^7$ pfu MVA-HBV + HBc-HBs 4-1/ $AS01_{B-4}$ | $10^7$ pfu MVA-HBV + HBc-HBs 4-1/ $AS01_{B-4}$ | $10^7$ pfu MVA-HBV + HBc-HBs 4-1/ $AS01_{B-4}$ | 7 dpII and 7 dpIIV |
| 3 | NaCl | NaCl | NaCl | NaCl | 7 dpII and 7 dpIV |

Results

HBc- and HBs-Specific CD8+ T-cell Response (Splenocytes)

Co-administration of HBc-HBs 4-1/$AS01_{B-4}$ with the ChAd155-hIi-HBV vector as prime and with the MVA-HBV vector as boost (Group 2) induced a 4 fold increase of HBc-specific CD8+ T-cell response when compared to injection of ChAd155-hIi-HBV/MVA-HBV only (Group 1) at 7 dpII (FIG. 8A). Similar CD8+ T-cell response against HBs was induced in both groups (FIG. 8B).

At 7dpIV, HBc- but not HBs-specific CD8+ T-cell response was clearly boosted after subsequent administrations of HBc-HBs/$AS01_{B-4}$ (5 fold increase compared to 7 dpII) (Group 1). No further increase of HBc- or HBs-specific CD8+ T-cells was observed when two additional doses of MVA-HBV/HBc-HBs 4-1/$AS01_{B-4}$ were co-administered (Group 2).

HBc- and HBs-Specific CDC T-Cell Response (Splenocytes)

Low levels of HBc- and HBs-specific CD4+ T-cells were detected after prime-boost ChAd155-hIi-HBV/MVA-HBV immunization (median 0.17% and 0.11%, respectively) (Group 1) while a potent response against both antigens was observed when HBc-HBs 4-1/$AS01_{B-4}$ was co-administered with prime-boost ChAd155-hIi-HBV/MVA-HBV (Group 2) at 7 dpII (FIG. 9A and FIG. 9B).

Subsequent administrations of HBc-HBs 4-1/$AS01_{B-4}$ after ChAd155-hIi-HBV/MVA-HBV prime-boost (Group 1) substantially enhanced both HBc- and HBs specific CD4+ T-cells responses (median 1.64% and 2.32%, respectively) at 7 dpIV. Finally, a robust increase of HBs-specific CD4+ T-cells was observed when two additional doses of MVA-HBV and HBc-HBs/$AS01_{B-4}$ were co-administered to the mice already vaccinated with the prime boost ChAd155-hIi-HBV/MVA-HBV co-administered with HBc-HBs/$AS01_{B-4}$ (Group 2) at same time point. The HBc-specific CD4+ T-cells remained at the same level as at 7 dpost II in that same group.

HBc- and HBs-Specific T-Cell Responses Measured in Liver Infiltrating Lymphocytes 7 days post-last immunization, the presence of vaccine-induced T-cell responses in the liver was investigated by ICS. In order to have a sufficient number of liver infiltrating lymphocytes to perform the in vitro re-stimulation and ICS, pools of cells recovered after perfusion of 3 or 4 livers were constituted for each data point. Due to the low number of data points, no statistical analysis was performed, and the results are descriptive.

Figure 10A:
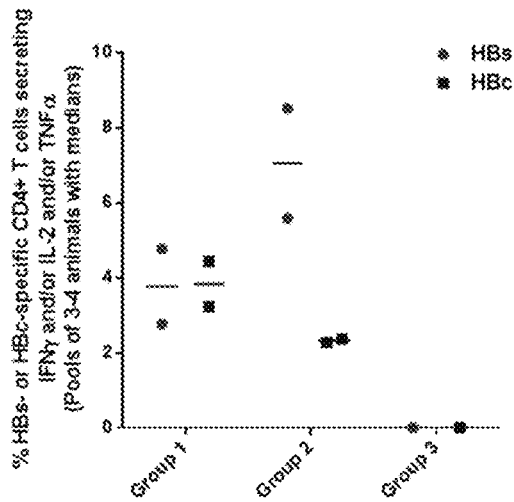
Figure 10B:
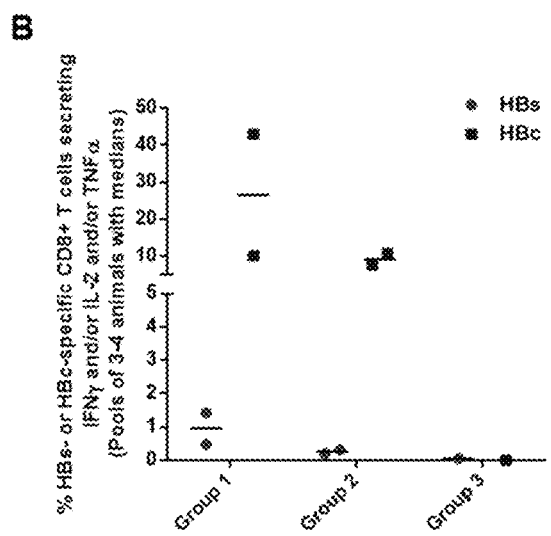

Both vaccine regimens elicited HBc- and HBs-specific CD4+ T-cells detectable in the liver of vaccinated mice (FIG. 10A and FIG. 10B). Strong HBc-specific CD8+ T-cell responses were measured in the livers of animals vaccinated with both vaccine regimens, while much lower frequencies of HBs-specific CD8+ T-cells were measured.

HBc- and HBs-Specific Antibody Response

Co-administration of ChAd155-hIi-HBV/MVA-HBV with HBc-HBs 4-1/AS01$_{B-4}$ (Group 2) induced the highest amount of anti-HBc antibodies at 7 dpII (FIG. 11A and FIG. 11B). Subsequent injections of MVA-HBV+HBc-HBs/AS01$_{B-4}$ did not further increase the level of anti-HBc antibody response (7 dpIV). A clear increase of anti-HBc-specific antibody response was observed at 7 dpIV after injections of HBc-HBs/AS01$_{B-4}$ in mice preliminary immunized with ChAd155-hIi-HBV and MVA-HBV (Group 1). The presence of the HBc-HBs/AS01$_{B-4}$ component seemed to be important in the schedule to elicit potent anti-HBs antibodies as no anti-HBs antibody response was detected in animals after immunization with ChAd155-hIi-HBV/MVA-HBV (FIG. 11A and FIG. 11B). The highest magnitude of response was observed in the co-ad group (Group 2) after last immunization.

Conclusions

In HLA.A2/DR1 transgenic mice, ChAd155-hIi-HBV/MVA-HBV elicited low but detectable HBc-specific CD4+ T-cell responses which were clearly enhanced by HBc-HBs 4-1/AS01$_{B-4}$. The initial prime-boost immunization with ChAd155-hIi-HBV/MVA-HBV induced potent HBc- and HBs-specific CD8+ T-cell responses, with the HBc-specific responses further increased after HBc-HBs/AS01$_{B-4}$ boost given sequentially.

Interestingly, when ChAd155-hIi-HBV/MVA-HBV were co-administered with HBc-HBs 4-1/AS01$_{B-4}$, high levels of HBc- and HBs-specific CD4+ and CD8+ T-cells were induced as well as antibodies after only two immunizations. Further immunizations with MVA-HBV+HBc-HBs/AS01$_{B-4}$ did not further increase the levels of these responses.

Moreover, vaccine-induced HBc- and HBs-specific CD4+ and CD8+ T-cells were also detected in the liver of animals vaccinated with both vaccine regimens.

Example 5—Evaluation of T and B-cell Tolerance to the "Invariant Chain" Sequence Ii Encoded by the ChAd155 Vector: Use of a ChAd155 Construct Coding for the Mouse Ii Sequence (mIi) in CB6F1 mice Objectives An immunogenicity study was conducted in CB6F1 mice to investigate T- and B-cell tolerance to the "invariant chain" sequence Ii in a homologous model using a ChAd155 construct coding for the mouse Ii sequence (mIi): ChAd155-mIi-HBV.

Study Design

Induction of autologous mIi-specific immune responses was evaluated by IFN-γ ELISpot (in splenocytes) and by ELISA (in blood serum) after 2 intramuscular immunizations (Day 0 and 14) with a high dose ($10^9$ vp) of the ChAd155-mIi-HBV vector (Table 5).

TABLE 5

Treatment groups

| Groups | Formulations |
|---|---|
| 1 | ChAd155-mIi-HBV ($10^9$ vp) at Days 0 and 14 |
| 2 | PBS at Days 0 and 14 |

Methods

For T-cell responses, 15 mer peptides overlapping by 11 amino acids encompassing the murine Ii sequence and arranged into a pool were used as antigen in the IFN-γ-ELISpot assay. For antibody responses, a commercially available murine Ii recombinant protein and a monoclonal antibody specific for murine Ii were respectively used to coat the ELISA plates and as positive control. As a positive control of "vaccine take", HBc- and HBs-specific T-cell responses were monitored in the IFN-γ-ELISpot assay.

Results

A potent HBc-specific T-cell response and a lower but detectable HBs-specific T-cell response were measured post-first and second immunization with ChAd155-mIi-HBV. Of note, the HBc Kb-restricted dominant Class I epitope (MGLKFRQL) was added in this construct to allow monitoring of the HBc-specific CD8+ T-cell response in this mouse strain and splenocytes were re-stimulated with this particular sequence in the ELISpot assay. No anti-mIi antibodies (FIG. 13) and no mIi-specific T-cells (FIG. 12) were detected in any animals at 2 weeks post-first or second immunization, suggesting that the immune tolerance to the mIi sequence was preserved.

Example 6—Evaluation of the Immunogenicity and Safety of ChAd155-hIi-HBV/MVA-HBV/HBc-HBs/AS01$_{B-4}$ Vaccine Regimens in AAV2/8-HBV Transduced HLA.A2/DR1 Mice Objectives The AAV2/8-HBV-transduced HLA.A2/DR1 murine model recapitulates virological and immunological characteristics of chronic HBV infection. In this model, the liver of mice is transduced with an adeno-associated virus serotype 2/8 (AAV2/8) vector carrying a replication-competent HBV DNA genome.

A single tail vein injection of $5 \times 10^{10}$ vg (viral genome) of the AAV2/8-HBV vector leads to HBV replication and gene expression in the liver of AAV2/8-HBV-transduced mice [Dion; 2013]. HBV DNA replicative intermediates, HBV RNA transcripts and HBc antigens are detected in the liver up to 1 year post-injection without associated significant liver inflammation. HBs and HBe antigens and HBV DNA can be detected in the sera up to 1 year. Furthermore, establishment of immune tolerance to HBV antigens is observed in this surrogate model of chronic HBV infection The objectives of this study conducted in AAV2/8-HBV transduced HLA.A2/DR1 mice were
- to demonstrate that the vaccine regimen can overcome the tolerance to HBs and HBc antigens.
- To evaluate the impact of liver infiltrating HBc-specific CD8+ T-cells, potentially targeting hepatocytes expressing the HBcAg, on the histology of the liver (H&E staining) and AST and ALT levels, as surrogate parameters for the liver function.

Study Design

Two different vaccine regimens, based on sequential immunization with ChAd155-hIi-HBV and MVA-HBV (both encoding the HBV core [HBc] and surface [HBs] antigens), either alone or in combination with HBc-HBs 4-1/AS01$_{B-4}$ followed by two additional doses HBc-HBs 4-1/AS01$_{B-4}$ (either alone or in combination with MVA-HBV), were tested (Table 6).

HLA.A2/DR1 mice from groups 1, 2 and 3 were transduced with $5 \times 10^{10}$ vg of AAV2/8-HBV vector (intravenous administration) at Day 0, while Group 4 served as a positive control for immunogenicity (no establishment of tolerance prior to vaccination).

Animals from Group 1 (N=21) were immunized at Day 31 with ChAd155-hIi-HBV followed by MVA-HBV at Day 58. Two doses of HBc-HBs 4-1 μg/AS01$_{B-4}$ were injected at Days 72 and 86 after this prime/boost viral vector regimen (Table 6).

Animals from Group 2 (N=21) were immunized at Day 31 with ChAd155-hIi-HBV and co-administrated with HBc-HBs 4-1/AS01$_{B-4}$ followed at Day 58 by a boost with MVA-HBV co-administered with HBc-HBs 4-1/AS01$_B$. Two subsequent co-immunizations of MVA-HBV and HBc-HBs 4-1/AS01$_B$ were performed at Days 72 and 86 (Table 6).

Animals from Group 3 (N=21) were injected with NaCl on Day 31, 58, 72 and 86 as negative control.

Animals from Group 4 (N=8) received the same vaccine regimen as Group 2 (except that they were not transduced with AAV2/8-HBV).

All vaccines were administered intramuscularly.

The level of HBs circulating antigen was measured in sera at Days 23, 65 and 93 (groups 1, 2 and 3).

HBs- and HBc-specific antibody responses were measured in sera from all animals at Days 23 (post-AAV2/8-HBV transduction), 65 (7 days post-second immunization) and 93 (7 days post-fourth immunization) by ELISA. The HBs- and HBc-specific CD4$^+$ and CD8$^+$ T cell responses were evaluated at Days 65 (9 animals/group) and 93 (12 animals/group) in splenocytes and liver infiltrating lymphocytes, after ex vivo re-stimulation and ICS (Groups 1, 2 and 3). These immunogenicity read-outs were performed only at Day 93 for animals from Group 4 (8 animals).

With regards to liver-related safety parameters, the levels of AST and ALT were measured in sera at Days 38, 65 and 93 and microscopic examination of liver sections stained with H&E was performed at Days 65 and 93 to detect potential vaccine-related histopathological changes or inflammation (Groups 1, 2 and 3).

derived from this model. All these statistics are presented with a two-sided 95% confidence interval. Multiplicity was not taken into account when computing these GMRs.

All analyses were performed using SAS 9.2

Humoral Responses

Descriptive statistics were performed to calculate the number of responders. The cut-off for responsiveness for anti-HBc or anti-HBs antibody responses was defined based on the geometric mean titers calculated in Group 3 (AAV2/8-HBV transduction but no vaccination).

Cellular Response

Descriptive analyses were performed to define the number of responders for either HBc-, HBs-specific CD4$^+$ or CD8$^+$ T cells. The cut-off for responsiveness was defined as the 95th percentile of measurements made in Group 3 (AAV2/8-HBV transduction but no vaccination).

Results

HBc-specific CD8$^+$ and CD4$^+$ T Cells

In AAV2/8-HBV-transduced HLA-A2/DR1 mice, the background level of HBc-specific CD8$^+$ or CD4$^+$ T cells was very low to undetectable without immunization at all the time-points tested (Group 3).

The immunization with ChAd155-hIi-HBV and MVA-HBV vectors, either alone (Group 1) or in combination with HBc-HBs 4-1/AS01$_{B-4}$ (Group 2) induced HBc-specific CD8$^+$ T cells (6/7 and 9/9 responders respectively at 7 days post-II), demonstrating a bypass of the tolerance to the HBc antigen (FIG. 14A). The two additional doses of HBc-HBs 4-1/AS01$_{B-4}$ either alone or in combination with MVA-HBV, only modestly increased these HBc-specific CD8$^+$ T cell responses as measured at 7 days post-fourth dose reaching median frequencies of 1% in Group 1 and 1.45% in Group 2. The frequencies of HBc-specific CD8$^+$ T cells induced by the same vaccine regimen as in Group 2, were higher in non-transduced HLA.A2/DR1 mice from Group 4 (8/8 responders, with frequencies ~4 fold higher at 7 days

TABLE 6

Treatment groups

| Groups | N* | Day 0 | Day 31 | Day 58 | Day 72 | Day 86 |
|---|---|---|---|---|---|---|
| 1 | 21 | AAV2/8-HBV | 10$^8$ vp ChAd155-hIi-HBV | 10$^7$ pfu MVA-HBV | HBc-HBs 4-1 μg/AS01$_{B-4}$ | HBc-HBs 4-1 μg/AS01$_{B-4}$ |
| 2 | 21 | AAV2/8-HBV | 10$^8$ vp ChAd155-hIi-HBV + HBc-HBs 4-1 μg/AS01$_{B-4}$ | 10$^7$ pfu MVA-HBV + HBc-HBs 4-1 μg/AS01$_{B-4}$ | 10$^7$ pfu MVA-HBV + HBc-HBs 4-1 μg/AS01$_{B-4}$ | 10$^7$ pfu MVA-HBV + HBc-HBs 4-1 μg/AS01$_{B-4}$ |
| 3 | 21 | AAV2/8-HBV | NaCl | NaCl | NaCl | NaCl |
| 4 | 8 | No vector | 10$^8$ vp ChAd155-hIi-HBV + HBc-HBs 4-1 μg/AS01$_{B-4}$ | 10$^7$ pfu MVA-HBV + HBc-HBs 4-1 μg/AS01$_{B-4}$ | 10$^7$ pfu MVA-HBV + HBc-HBs 4-1 μg/AS01$_{B-4}$ | 10$^7$ pfu MVA-HBV + HBc-HBs 4-1 μg/AS01$_{B-4}$ |

*1 mouse was found dead in Group 3 before Day 65 and in Group 2 before Day 93.

Statistical Analysis

AST and ALT Levels

An ANOVA model for repeated measures including Gender, Day, Group and the three two-by-two interactions was fitted on the log 10-transformed enzymatic activity values, using the unstructured covariance structure. Model assumptions were verified. The interactions insignificant at the 5% level were removed from the model. For both enzymes, the final model included Gender, Day, Group and the interaction between Group and Day. The geometric means of enzymatic activity of each group at each time point were derived from this model. Group comparisons of interest are reported through geometric mean ratios (GMRs) that were also post-IV), as expected due to the immune tolerance toward the HBc antigen. HBc-specific CD8$^+$ T cells were also detected in the liver of vaccinated mice, with the same profile as in spleens (FIG. 14B).

Both vaccine regimens elicited very low to undetectable HBc-specific CD4$^+$ T cells in AAV2/8-HBV-transduced HLA-A2/DR1 mice (Groups 1 and 2), while a robust response was measured in non-transduced mice (Group 4), suggesting that the vaccine regimen did not overcome the CD4$^+$ T cell tolerance to the HBc antigen under these experimental conditions (FIG. 15A and FIG. 15B).

HBs-Specific CD8$^+$ and CD4$^+$ T Cells

The immunization with ChAd155-hIi-HBV and MVA-HBV vectors, either alone (Group 1) or in combination with HBc-HBs 4-1/AS01$_{B-4}$ (Group 2) elicited HBs-specific CD8$^+$ T cells with no further increase of the intensities following the two additional doses of HBc-HBs 4-1/AS01$_{B-4}$ either alone or in combination with MVA-HBV, in AAV2/8-HBV transduced mice (FIG. 16A). At the end of the vaccination schedule (7 days post-fourth dose), the frequencies of HBs-specific CD8$^+$ T cells measured in animals from Groups 1 and 2 were close to the ones detected in Group 4 (non-transduced HLA.A2/DR1 mice, median at 7 days post-IV=0.62%, 5/8 responders), suggesting an overcome of the T cell tolerance toward the HBs antigen. HBs-specific CD8$^+$ T cells were detected in the livers of animals from Groups 1, 2 and 4 in most of the vaccinated animals (FIG. 16B).

HBs-specific CD4$^+$ T cells were induced after administration of HBc-HBs 4-1/AS01$_{B-4}$ alone or in combination with vectors, from 7 days post-second vaccination in Group 2 and from 7 days post-fourth vaccination in Group 1 (FIG. 17A). The vaccine schedule used in animals from Group 2 elicited about 3 fold higher frequencies of HBs-specific CD4$^+$ T cells (median at 7 days post-IV=3.7%, 11/11 responders) as compared to vaccine schedule used in animals from Group 1 (median at 7 days post-IV=1.34%, 11/12 responders), reaching similar levels as in Group 4 (non-transduced HLA.A2/DR1 mice, median at 7 days post-IV=3%, 8/8 responders), suggesting a complete overcome of the T cell tolerance toward the HBs antigen. Similarly to the systemic CD4$^+$ T cell responses, HBs-specific CD4$^+$ T cells were detected in the livers of animals from Groups 1, 2 and 4 in all vaccinated animals (FIG. 17B).

HBs- and HBc-Specific Antibody Responses

At 23 days after the injection of the AAV2/8-HBV vector, no anti-HBs antibody responses were detected in HLA.A2/DR1 mice, suggesting a strong humoral tolerance toward the HBs antigen. The immunization with ChAd155-hIi-HBV and MVA-HBV vectors alone (Group 1) did not break this tolerance while the immunization of the vectors in combination with HBc-HBs 4-1/AS01$_{B-4}$ led to the induction of anti-HBs antibody responses in 15 out of the 21 animals at Day 65 (Group 2) (FIG. 18A). The further administration of 2 doses of HBc-HBs 4-1/AS01$_{B-4}$ in group 1 elicited detectable anti-HBs antibodies (Geometric mean titers (GMT) of 116.8 and 8/12 responders at Day 93) and the 2 additional doses of MVA-HBV combined with HBc-HBs 4-1/AS01$_{B-4}$ in Group 2 further increased the intensity of the anti-HBs antibody response up to a GMT of 775 with 11/11 responders, while remaining ~5 fold lower than in non-AAV2/8-HBV transduced animals from Group 4 (GMT=3933) at Day 93.

Similarly, anti-HBc antibody responses were induced only when the HBc-HBs 4-1/AS01$_{B-4}$ component was present in the vaccine regimen, with 3 fold higher levels measured at Day 93 in animals from Group 2 (GMT=1335, 5; 11/11 responders) as compared to Group 1 (GMT=442.8; 12/12 responders) FIG. 18B). The anti-HBc antibody titers induced in the non-transduced mice (Group 4) with the same vaccine regimen as in Group 2 were higher (~27 fold, GMT=35782).

These results show that the presence of the adjuvanted protein component in the vaccine regimen is critical to break the humoral tolerance to both HBc and HBs antigens. Furthermore the vaccine regimen used in Group 2, containing 4 administrations of the HBc-HBs 4-1/AS01$_{B-4}$ elicited the highest anti-HBc and anti-HBs antibody responses, while remaining lower than in non-AAV2/8-HBV transduced mice (Group 4).

AST/ALT Levels

As a liver-related inflammation parameter, the serum activities of AST and ALT were measured at Days 38 (7 days post-first vaccination), 65 (7 days post-second vaccination) and/or 93 (7 days post-fourth immunization) (all Groups). Overall, the AST and ALT levels were stable during the course of the vaccine regimens (Groups 1 and 2) in AAV2/8-HBV transduced HLA.A2/DR1 mice and similar to the ones measures in mice not receiving vaccines (Group 3) (FIG. 19A and FIG. 19B). AST levels were found statistically significantly higher in animals from the vaccine groups (Groups 1 and 2) as compared to the control Group 3 at Day 65. However, the AST levels were surprisingly low at Day 65 in animals from Group 3 as compared to the rest of the kinetics, suggesting that these differences were rather due to the particularly unexpectedly low values obtained in the control group 3 at this time-point, rather than an increase of the AST levels in the vaccine groups (Groups 1 and 2) (FIG. 19A).

A slightly lower ALT level was measured at Day 38 in animals from Group 1 as compared to in control animals from Group 3, but this difference was not considered as clinically relevant (FIG. 19B).

Liver Microscopic Examination

Microscopic examination of liver sections stained with H&E was performed at Days 65 and 93 to detect potential vaccine-related histopathological changes or inflammation (Groups 1, 2 and 3) (Table 7).

There were no test item-related microscopic findings either on Day 65 (7 days after the injection of the second viral vectored vaccine, MVA-HBV with or without HBc-HBs 4-1/AS01$_{B-4}$) or on Day 93 (7 days after the last injection) in AAV2/8-HBV transduced HLA-A2/DR mice, i.e. there were no histopathological changes that could be associated with the use of the vaccine components ChAd155-hIi-HBV, MVA-HBV and HBc-HBs 4-1/AS01$_{B-4}$.

In addition, except for control animal 3.13 (which presented a focal grade 1 piecemeal necrosis), none of the animals presented morphological signs of chronic hepatitis.

Other microscopic findings noted in treated animals were considered incidental changes, as they also occurred in the control group, were of low incidence/magnitude, and/or are common background findings in mice of similar age [McInnes, 2012].

TABLE 7

Microscopic examination of the livers of animals from groups 1, 2 and 3 at Days 65 and 93
45028_EPS (Raw Data)

Group 1 ("low dose"), treated with: ChAd155-HBV (at Day 30) + MVA-HBV (at Day 58) + HBc-HBs/AS01B-4 (at Day 72 and 86)

| | 1.1 | 1.2 | 1.3 | 1.4 | 1.5 | 1.6 | 1.7 | 1.8 | 1.9 | 1.10 | 1.11 | 1.12 | 1.13 | 1.14 | 1.15 | 1.16 | 1.17 | 1.18 | 1.19 | 1.20 | 1.21 |
|---|---|---|---|---|---|---|---|---|---|---|---|---|---|---|---|---|---|---|---|---|---|
| LIVER Day of Sacrifice | 93 | 93 | 93 | 93 | 65 | 93 | 65 | 93 | 93 | 65 | 93 | 65 | 65 | 65 | 93 | 93 | 65 | 93 | 65 | 65 | 93 |
| Piecemeal necrosis | 0 | 0 | 0 | 0 | 0 | 0 | 0 | 0 | 0 | 0 | 0 | 0 | 0 | 0 | 0 | 0 | 0 | 0 | 0 | 0 | 0 |
| Focal lobular necrosis | 0 | 0 | 0 | 0 | 0 | 0 | 0 | 0 | 0 | 0 | 0 | 0 | 0 | 0 | 0 | 0 | 0 | 0 | 0 | 0 | 0 |

TABLE 7-continued

Microscopic examination of the livers of animals from groups 1, 2 and 3 at Days 65 and 93
45028_EPS (Raw Data)

| | | | | | | | | | | | | | | | | | | | | | |
|---|---|---|---|---|---|---|---|---|---|---|---|---|---|---|---|---|---|---|---|---|---|
| METAVIR A (Activity) | 0 | 0 | 0 | 0 | 0 | 0 | 0 | 0 | 0 | 0 | 0 | 0 | 0 | 0 | 0 | 0 | 0 | 0 | 0 | 0 | 0 |
| METAVIR B (Fibrosis) | 0 | 0 | 0 | 0 | 0 | 0 | 0 | 0 | 0 | 0 | 0 | 0 | 0 | 0 | 0 | 0 | 0 | 0 | 0 | 0 | 0 |
| Inflammatory cell foci | 0 | 0 | 0 | 0 | 0 | 0 | 0 | 0 | 0 | 0 | 0 | 0 | 0 | 0 | 0 | 0 | 0 | 0 | 0 | 0 | 0 |
| Single Cell necrosis | 0 | 0 | 0 | 0 | 0 | 0 | 0 | 0 | 0 | 0 | 0 | 0 | 0 | 0 | 0 | 0 | 0 | 0 | 0 | 0 | 0 |
| Extramedullary hematopoiesis | 0 | 0 | 0 | 0 | 0 | 0 | 0 | 0 | 0 | 0 | 0 | 0 | 0 | 0 | 0 | 0 | 0 | 0 | 0 | 0 | 0 |
| Pigment (consistent with hemosiderin), Kupffer cells | 0 | 0 | 0 | 0 | 0 | 0 | 0 | 0 | 0 | 0 | 0 | 0 | 0 | 0 | 0 | 0 | 0 | 0 | 0 | 0 | 0 |

Group 2 ("high dose"), treated with: ChAd155-HBV (at Day 30) + MVA-HBV (at Day 58) + HBc-HBs/AS01B-4 (at Day 30, 58, 72 and 86)

| LIVER | 2.1 | 2.2 | 2.3 | 2.4 | 2.5 | 2.6 | 2.7 | 2.8 | 2.9 | 2.10 | 2.11 | 2.12 | 2.13 | 2.14 | 2.15 | 2.16 | 2.17 | 2.18 | 2.19 | 2.20 | 2.21 |
|---|---|---|---|---|---|---|---|---|---|---|---|---|---|---|---|---|---|---|---|---|---|
| Day of Sacrifice | 93 | 65 | 93 | 93 | 65 | 93 | 65 | 65 | NA | 93 | 93 | 93 | 65 | 65 | 93 | 93 | 65 | 93 | 65 | 65 | 93 |
| Piecemeal necrosis | 0 | 0 | 0 | 0 | 0 | 0 | 0 | 0 | NA | 0 | 0 | 0 | 0 | 0 | 0 | 0 | 0 | 0 | 0 | 0 | 0 |
| Focal lobular necrosis | 0 | 0 | 0 | 0 | 0 | 0 | 0 | 0 | NA | 0 | 0 | 0 | 0 | 0 | 0 | 0 | 0 | 0 | 0 | 0 | 0 |
| METAVIR A (Activity) | 0 | 0 | 0 | 0 | 0 | 0 | 0 | 0 | NA | 0 | 0 | 0 | 0 | 0 | 0 | 0 | 0 | 0 | 0 | 0 | 0 |
| METAVIR B (Fibrosis) | 0 | 0 | 0 | 0 | 0 | 0 | 0 | 0 | NA | 0 | 0 | 0 | 0 | 0 | 0 | 0 | 0 | 0 | 0 | 0 | 0 |
| Inflammatory cell foci | 0 | 0 | 0 | 0 | 0 | 0 | 0 | 0 | NA | 0 | 0 | 0 | 0 | 0 | 0 | 0 | 0 | 0 | 0 | 0 | 0 |
| Single Cell necrosis | 0 | 0 | 0 | 0 | 0 | 0 | 0 | 0 | NA | 0 | 0 | 0 | 0 | 0 | 0 | 0 | 0 | 0 | 0 | 0 | 0 |
| Extramedullary hematopoiesis | 0 | 0 | 0 | 0 | 0 | 0 | 0 | 0 | NA | 0 | 0 | 0 | 0 | 0 | 0 | 0 | 0 | 0 | 0 | 0 | 0 |
| Pigment (consistent with hemosiderin), Kupffer cells | 0 | 0 | 0 | 0 | 0 | 0 | 0 | 0 | NA | 0 | 0 | 0 | 0 | 0 | 0 | 0 | 0 | 0 | 0 | 0 | 0 |

NA: not applicable (mortality 2.9)

Group 3 (control), treated with: NaCl

| LIVER | 3.1 | 3.2 | 3.3 | 3.4 | 3.5 | 3.6 | 3.7 | 3.8 | 3.9 | 3.10 | 3.11 | 3.12 | 3.13 | 3.14 | 3.15 | 3.16 | 3.17 | 3.18 | 3.19 | 3.20 | 3.21 |
|---|---|---|---|---|---|---|---|---|---|---|---|---|---|---|---|---|---|---|---|---|---|
| Day of Sacrifice | 65 | 93 | 65 | 93 | 93 | 65 | 93 | 65 | 65 | 65 | 93 | 93 | 93 | 93 | 93 | 93 | 65 | 93 | 65 | 65 | 93 |
| Pecerneal necrosis | 0 | NA | 0 | 0 | 0 | 0 | 0 | 0 | 0 | 0 | 0 | 0 | 0 | 0 | 0 | 0 | 0 | 0 | 0 | 0 | 0 |
| Focal lobular necrosis | 0 | NA | 0 | 0 | 0 | 0 | 0 | 0 | 0 | 0 | 0 | 0 | 0 | 0 | 0 | 0 | 0 | 0 | 0 | 0 | 0 |
| METAVIR A (Activity) | 0 | NA | 0 | 0 | 0 | 0 | 0 | 0 | 0 | 0 | 0 | 0 | 0 | 0 | 0 | 0 | 0 | 0 | 0 | 0 | 0 |
| METAVIR B (Fibrosis) | 0 | NA | 0 | 0 | 0 | 0 | 0 | 0 | 0 | 0 | 0 | 0 | 0 | 0 | 0 | 0 | 0 | 0 | 0 | 0 | 0 |
| Inflammatory cell foci | 0 | NA | 0 | 0 | 0 | 0 | 0 | 0 | 0 | 0 | 0 | 0 | 0 | 0 | 0 | 0 | 0 | 0 | 0 | 0 | 0 |
| Single Cell necrosis | 0 | NA | 0 | 0 | 0 | 0 | 0 | 0 | 0 | 0 | 0 | 0 | 0 | 0 | 0 | 0 | 0 | 0 | 0 | 0 | 0 |
| Extramedullary hematopoiesis | 0 | NA | 0 | 0 | 0 | 0 | 0 | 0 | 0 | 0 | 0 | 0 | 0 | 0 | 0 | 0 | 0 | 0 | 0 | 0 | 0 |
| Pigment (consistent with hemosiderin), Kupffer cells | 0 | NA | 0 | 0 | 0 | 0 | 0 | 0 | 0 | 0 | 0 | 0 | 0 | 0 | 0 | 0 | 0 | 0 | 0 | 0 | 0 |

*focal/slight piecemeal necrosis in a single portal space
NA: not applicable (mortality 3.2)

HBs Antigen Levels in Sera from AAV2/8-HBV Injected Mice.

As already reported in Dion et al [Dion, 2013], HBs antigen levels were higher in males as compared to females, 23 days post-injection with the AAV2/8-HBV vectors. These levels remained stable in all groups, without detectable impact of the vaccination regimens (FIG. 20). AAV2/8-HBVinjected mouse is however not an animal model for studying vaccine efficacy on HBsAg.

Conclusion

In a surrogate model of chronic HBV infection where immune tolerance toward HBc and HBs antigen is established, i.e. AAV2/8-HBV-transduced HLA-A2/DR1 mice, both tested vaccine regimens bypassed the tolerance by inducing HBc- and HBs-specific IgG and CD8+ T cell responses as well as HBs-specific CD4+ T cell responses, albeit at lower levels than in non-transduced mice, as expected due to strong immune tolerance. When the ChAd155-hIi-HBV/MVA-HBV vectors were co-administered with HBc-HBs 4-1/AS01$_{B-4}$, the intensities of the vaccine induced antibody and T cell responses were higher than with the vaccine regimen where the vectors and adjuvanted proteins were administered sequentially. Furthermore, while assessing the vaccine-associated liver inflammation by measuring serum activities of AST and ALT and by performing liver histopathological evaluation, no increase in liver enzymes was detected in the vaccine groups when compared with the non-vaccinated one and no microscopic findings could be related to the vaccine treatments. Altogether, these results show that the tested vaccine candidates successfully restored HBs- and HBc-specific antibody and CD8$^+$ T cell responses as well as HBs-specific CD4$^+$ T cell responses without detection of associated-signs of liver alteration, under these experimental conditions.

Summary of Non-Clinical Immunology Data of Examples 1-6

Studies in CB6F1 mice vaccinated with the vaccine proteins (HBc-HBs) formulated in AS01$_{B-4}$ Adjuvant System suggested a negative interference of the HBs antigen on HBc-induced antibody and CD4$^+$ T-cell responses. Nevertheless, HBc-HBs/AS01$_{B-4}$ combination vaccine was able to mount robust specific CD4$^+$ T-cell and antibody responses to both vaccine antigens.

When compared to alum-based or non-adjuvanted formulation, the AS01 family-based formulation induced significantly higher CD4$^+$ T-cell and antibody responses to both HBc and HBs antigens.

The administration of ChAd155-hIi-HBV in HLA.A2/DR1 transgenic mice induced a strong CD8$^+$ T-cell response to the HBc antigen and to a lesser extent to the HBs antigen. The response to the HBc antigen was clearly enhanced by the presence of the hIi in the construct. The subsequent administration of MVA-HBV further increased the CD8$^+$ T-cell response against HBc antigen: following the MVA boost, a higher frequency of HBc-specific CD8$^+$ T-cells was observed in mice primed with ChAd155-hIi-HBV versus mice primed with ChAd155-HBV, while HBs-specific CD8$^+$ T-cell responses were not further enhanced.

When administered to HLA.A2/DR1 transgenic mice, the full vaccination regimens (i.e. sequential or concomitant administration of viral vectors and adjuvanted proteins) induced robust CD4$^+$ T-cell, CD8$^+$ T-cell and antibody responses to both vaccine antigens. Moreover vaccine-induced HBs- and HBc-specific CD4$^+$ and CD8$^+$ T-cells were detected in the liver of animals vaccinated with both vaccine regimens.

An immunogenicity study was conducted in CB6F1 to investigate T and B cell tolerance to the "invariant chain" sequence (Ii) in a homologous model using a ChAd155 construct coding for the mouse Ii sequence (mIi): ChAd155-mIi-HBV. Induction of autologous mIi-specific immune responses was evaluated after 2 immunizations (Day 0 and 14) with a high dose (10$^9$ vp) of the ChAd155-mIi-HBV vector. No anti-mIi antibodies and no mIi-specific T-cells were detected in any animals at 2 weeks post-first or second immunization, suggesting that the immune tolerance to the mIi sequence was preserved.

In a preclinical HBV-persistent mouse model (AAV2/8-HBV transduced HLA.A2/DR1 mice), where immune tolerance is observed to HBV antigens, the vaccine regimens were capable of breaking the tolerance with induction of HBc- and HBs-specific CD8$^+$ T cells, HBs-specific CD4$^+$ T cells and antibody responses to both HBs and HBc antigens, although there was no HBc-specific CD4$^+$ T cell response observed. The levels of vaccine-induced responses in the MV-transduced mice were, however, (and as expected) lower than those detected in naïve HLA.A2/DR1 mice. Furthermore, while assessing the vaccine-associated liver inflammation by measuring serum activities of aspartate aminotransferase (AST) and ALT and by performing liver histopathological evaluation, no increase in liver enzymes was detected in the vaccine groups when compared with the non-vaccinated group and no microscopic findings could be related to the vaccine treatment. Altogether, these results show that the tested vaccine candidates successfully restored HBs- and HBc-specific antibody and CD8$^+$ T cell responses as well as HBs-specific CD4$^+$ T cell responses without detection of associated-signs of liver alteration, under these experimental conditions.

Example 7—Immunogenicity Evaluation of Different Adjuvanted Recombinant Protein HBc/HBs Ratios Objectives The purpose of the experiment was to confirm a negative interference of the HBs antigen on the HBc-induced CD4$^+$ T cell response as seen in Example 2 at 7 days post third immunization where the HBs and HBc antigens were mixed with a ratio of 1 to 1. A further aim was to evaluate various ratios of HBs/HBc to limit this interference and to ensure at least a potent HBc-specific CD4$^+$ T cell response while at the same time generating a robust HBc and HBs-specific antibody response.

Study Design

CB6F1 mice (30 mice per group) of 6-8 weeks old were immunized three times intra-muscularly (gastrocnemian muscle) at days 0, 14 and 28 with various formulations containing HBc and HBs antigens (listed in Table 8) in 50 µl of AS01$_{B-3}$ or AS01$_{B-4}$. CB6F1 mice were randomly assigned to one of the study groups. The evaluation of HBc and HBs specific T cell responses by Intracellular Cytokine Staining (ICS) was done by using leukocytes collected 7 days after the second and the third immunization from 6 pools of 5 mice/group. Serum was collected from individual mice 14 days after the second and the third immunizations and only serum of 20 randomized mice were tested for the evaluation of HBc- and HBs-specific antibody total Ig responses due to the statistical sample size analysis.

TABLE 8

Study design of HBc/HBs ratio experiment in CB6F1 mice.

| Group | N | Treatment Vaccine dose | Adjuvant dose | Immunization schedule Days |
|---|---|---|---|---|
| 1 | 30 | 1 µg HBs | AS01B-4 (1/10 HD) | 0, 14, 28 |
| 2 | 30 | 0.25 µg HBs | AS01B-4 (1/10 HD) | 0, 14, 28 |
| 3 | 30 | 0.1 µg HBs | AS01B-4 (1/10 HD) | 0, 14, 28 |
| 4 | 30 | 4 µg HBc | AS01B-4 (1/10 HD) | 0, 14, 28 |
| 5 | 30 | 1 µg HBc | AS01B-4 (1/10 HD) | 0, 14, 28 |
| 8 | 30 | 1 µg HBc + 1 µg HBs | AS01B-4 (1/10 HD) | 0, 14, 28 |
| 9 | 30 | 4 µg HBc + 1 µg HBs | AS01B-4 (1/10 HD) | 0, 14, 28 |
| 10 | 30 | 4 µg HBc + 0.25 µg HBs | AS01B-4 (1/10 HD) | 0, 14, 28 |
| 11 | 30 | 1 µg HBc + 0.25 µg HBs | AS01B-4 (1/10 HD) | 0, 14, 28 |
| 12 | 30 | 4 µg HBc + 0.1 µg HBs | AS01B-4 (1/10 HD) | 0, 14, 28 |
| 13 | 30 | NaCl | / | 0, 14, 28 |

Groups 6 & 7 were included in the experiment to address another objective and are omitted for clarity purposes.
HD: Human dose Statistical Analysis The non-inferiority of HBc-HBs groups as compared to corresponding HBc groups was evaluated. This non-inferiority will be reached if the UL of 95% CI of the geometric mean ratios of the frequencies (in %) of HBc-specific CD4$^+$ T-cell expressing at least one cytokine (IL-2 and/or IFN-$\gamma$ and/or TNF-$\alpha$) for HBc groups over corresponding HBc-HBs groups is below 2 at 7-day post dose III. As it was a first evaluation and as criteria were not pre-defined, no adjustment for multiplicity was applied.

An ANOVA (Analysis of Variance) model was used to answer the two primary objectives. This model was fitted on log 10 CD4$^+$ frequencies post dose III including group (4 to 12), interaction as fixed effects and using a heterogeneous variance model (identical variances were not assumed between groups). This model was used to estimate geometric means (and their 95% CIs) as well as the geometric mean ratios and their 95% CIs using a back-transformation of log 10 means and differences.

Results

Antigen-Specific CD4+ T Cell Responses

All formulations after the 2$^{nd}$ immunization induced strong anti-HBc and HBs specific CD4$^+$ T cell responses (±1%). Although the magnitude of the HBc-specific CD4$^+$ T-cell response elicited by the formulation containing an equal amount of HBc and HBs in AS01$_{B-4}$ tended to be lower (FIG. 23) when compared to the HBc/AS01$_{B-4}$ alone group, these differences were not statistically significant because the ratio was ±1.4 (p=0.143) (FIG. 23A and FIG. 23B). After the 3$^{rd}$ immunization, the magnitude of the HBc-specific CD4$^+$ T-cell response elicited by the formulation containing an equal amount of HBc and HBs in AS01$_{B-4}$ was statistically lower (GMR 0.391 and 95% CI [0.184-0.828]) when compared to the HBc/AS01$_{B-4}$ alone group (FIG. 24A and FIG. 24B). This confirmed the observation in Example 2 of interference of HBs on HBc-specific CD4$^+$ T cell responses. The interference was less pronounced when antigens were formulated on a ratio of 4 to 1 of HBc and HBs antigen. No such negative impact was seen when looking at HBs-specific CD4$^+$ T cell responses (FIG. 23A and FIG. 23B; FIG. 24A and FIG 24B).

By further increasing HBc to HBs ratios there was a tendency, although not statistically significant, for additional recovery of such HBc-specific CD4$^+$ T cell response with medians up to 1.7% of total HBc-specific CD4$^+$ T cells expressing IFN-$\gamma$ and/or IL-2 and/or TNF$\alpha$.

HBs-specific CD8$^+$ T cell responses were evaluated after the 2$^{nd}$ and 3$^{rd}$ immunization (FIG. 25A and FIG. 25B). A HBs-specific dose range response was observed after the 2$^{nd}$ and 3$^{rd}$ immunization. After the third immunization, HBs specific CD8$^+$ T cell responses tended to decrease when co-formulated with an equal amount of HBc antigen (GMR 0.66 and 95% CI [0.337-1.295]), however, this ratio is not statistically significant (p=0.1717). HBc-specific CD8$^+$ T cell responses were low to undetectable (Lower than 0.1%, data not shown).

Antigens Specific Antibody Responses

All formulations after the 2$^{nd}$ immunization induced high and similar anti-HBc and HBs total Ig responses with no negative impact when co-formulating HBs and HBc at 1 to 1 ratio in AS01$_{B-4}$ adjuvant system (FIG. 26A and FIG. 26B). The anti-HBc specific total Ig responses were boosted after the third immunization (FIG. 27A and FIG. 27B). HBs interference was seen on the level of HBc-specific antibody responses when co-formulating HBs and HBc at 1 to 1 ratio in AS01$_{B-4}$ adjuvant system. The GMT ratios and 95% confidence interval was 1.88 [1.44; 2.44] with the p-values <0.0001. Increasing the ratio of HBc to HBs by four allows the recovery of HBc humoral responses, GMT ratios and 95% confidence interval was 1.37 [1.04; 1.80] with the p=0.0262. HBc had no negative impact on the level of HBs-specific antibody response as previously reported (FIG. 26A and FIG. 26B; FIG. 27A and FIG. 27B).

Conclusion

Results of these experiment indicate that the negative interference of HBs on HBc-specific CD4$^+$ T cell and humoral responses observed when both antigens were co-formulated in a 1/1 ratio was overcome for formulations with a HBc/HBs ratio≥4. As a result doses of 4 µg HBc and 1 µg HBs were selected for further preclinical experiments.

SEQUENCE LISTINGS
SEQ ID NO: 1: Amino acid sequence of HBs
MENITSGFLGPLLVLQAGFFLLTRILTIPQSLDSWWTSLNFLGGSP

VCLGQNSQSPTSNHSPTSCPPICPGYRWMCLRRFIIFLFILLLCLI

FLLVLLDYQGMLPVCPLIPGSTTTNTGPCKTCTTPAQGNSMFPSCC

CTKPTDGNCTCIPIPSSWAFAKYLWEWASVRFSWLSLLVPFVQWFV

GLSPTVWLSAIWMMWYWGPSLYSIVSPFIPLLPIFFCLWVYI

SEQ ID NO: 2: Amino acid sequence of HBc truncate
MDIDPYKEFGATVELLSFLPSDFFPSVRDLLDTASALYREALESPE

HCSPHHTALRQAILCWGELMTLATANVGNNLEDPASRDLVVNYVNT

NMGLKIRQLLWFHISCLTFGRENLEYLVSFGVWIRTPPAYRPPNAP

ILSTLPETTVV

SEQ ID NO: 3: Amino acid sequence of spacer incorporating 2A cleaving region of the foot and mouth disease virus
APVKQTLNFDLLKLAGDVESNPGP SEQ ID NO: 4: Nucleotide sequence encoding spacer incorporating 2A cleavage region of the foot and mouth disease virus
GCCCCTGTGAAGCAGACCCTGAACTTCGACCTGCTGAAGCTGGCCG

GCGACGTGGAGAGCAATCCCGGCCCT

SEQ ID NO: 5: Amino acid sequence of HBc-2A-HBs
MDIDPYKEFGATVELLSFLPSDFFPSVRDLLDTASALYREALESPE

HCSPHHTALRQAILCWGELMTLATANVGNNLEDPASRDLVVNYVNT

NMGLKIRQLLWFHISCLTFGRENLEYLVSFGVWIRTPPAYRPPNAP

ILSTLPETTVVRRRDRGRSPRRRTPSPRRRRSQSPRRRRSQSRESQ

CAPVKQTLNFDLLKLAGDVESNPGPMENITSGFLGPLLVLQAGFFL

LTRILTIPQSLDSWWTSLNFLGGSPVCLGQNSQSPTSNHSPTSCPP

ICPGYRWMCLRRFIIFLFILLLCLIFLLVLLDYQGMLPVCPLIPGS

TTTNTGPCKTCTTPAQGNSMFPSCCCTKPTDGNCTCIPIPSSWAFA

KYLWEWASVRFSWLSLLVPFVQWFVGLSPIVWLSAIWMMWYWGPSL

YSIVSPFIPLLPIFFCLWVYI

SEQ ID NO: 6: Nucleotide sequence encoding HBc-2A-HBs
ATGGACATCGATCCCTACAAGGAATTTGGCGCCACCGTGGAGCTGC

TGAGCTTCCTGCCCAGCGACTTCTTCCCCAGCGTGAGGGACCTCCT

GGACACCGCCAGCGCCCTGTACAGGGAGGCCCTGGAATCTCCCGAG

-continued
CACTGCAGCCCACACCACACCGCACTGAGGCAGGCCATCCTGTGCT
GGGGAGAGCTGATGACCCTCGCCACCTGGGTGGGCAACAACCTGGA
GGACCCCGCCAGCAGGGACCTGGTGGTGAACTACGTCAACACCAAC
ATGGGCCTGAAGATCAGGCAGCTGCTGTGGTTCCACATCAGCTGCC
TGACCTTCGGCAGGGAGACCGTGCTGGAGTACCTGGTGAGCTTCGG
CGTGTGGATCAGGACACCTCCCGCCTACAGACCCCCCAACGCCCCC
ATCCTGAGCACCCTGCCCGAGACCACAGTGGTGAGGAGGAGGGACA
GGGGCAGGTCACCCAGGAGGAGGACTCCAAGCCCCAGGAGGAGGAG
GAGCCAGAGCCCCAGGAGAAGGAGGAGCCAGAGCAGGGAGAGCCAG
TGCGCCCCTGTGAAGCAGACCCTGAACTTCGACCTGCTGAAGCTGG
CCGGCGACGTGGAGAGCAATCCCGGCCCTATGGAGAACATCACCAG
CGGCTTCCTGGGCCCCCTGCTGGTGCTGCAGGCAGGCTTCTTCCTG
CTGACCAGGATCCTGACCATCCCCCAGAGCCTGGACAGCTGGTGGA
CCAGCCTGAACTTCCTCGGCGGGAGCCCCGTGTGCCTGGGCCAGAA
CAGCCAGTCTCCCACCAGCAATCACAGCCCCACCAGCTGCCCCCCA
ATCTGTCCTGGCTACCGGTGGATGTGCCTGAGGAGGTTCATCATCT
TCCTGTTCATCCTGCTCCTGTGCCTGATCTTCCTGCTGGTGCTGCT
GGACTACCAGGGAATGCTGCCAGTGTGTCCCCTGATCCCCGGCTCA
ACCACCACTAACACCGGCCCCTGCAAAACCTGCACCACCCCCGCTC
AGGGCAACAGCATGTTCCCAAGCTGCTGCTGCACCAAGCCCACCGA
CGGCAACTGCACCTGCATTCCCATCCCCAGCAGCTGGGCCTTCGCC
AAGTATCTGTGGGAGTGGGCCAGCGTGAGGTTCAGCTGGCTCAGCC
TGCTGGTGCCCXrCGTCCAGTGGTTTGTGGGCCTGAGCCCCACCGT
GTGGCTGAGCGCCATCTGGATGATGTGGTACTGGGGCCCCAGCCTG
TACTCCATCGTGAGCCCCTTCATCCCCCTGCTGCCCATTTTCTTCT
GCCTGTGGGTGTACATC SEQ ID NO: 7: Amino acid sequence of hIi
MHRRRSRSCREDQKPVMDDQRDLISNNEQLPMLGRRPGAPESKCSR
GALYTGFSILVTLLLAGQATTAYFLYQQQGRLDKLTVTSQNLQLEN
LRMKLPKPKPVSKMRMATPLLMQALPMGALPQGPMQNATKYGNMTE
DHVMHLLQNADPLIWYPPLKSFPENLRHLKNTMETIDWKWESWMHH
WLLFEMSRHSLEQKPTDAPPKESLELEDPSSGGVTKQDLGPVPM SEQ ID NO: 8: Nucleotide sequence encoding hIi
atgcacaggaggaggagcaggagctgcagggaggaccagaagcccg
tgatggacgaccagcgcgacctgatcagcaacaacgagcagctgcc
aatgctgggcaggaggcccggagcacccgaaagcaagtgcagcagg
ggcgccctgtacaccggcttcagcatcctggtgaccctcctgctgg
ccggccaggccaccaccgcctatttcctgtaccagcagcagggcag
gctcgataagctgaccgtgacctcccagaacctgcagctggagaac
ctgaggatgaagctgcccaagcccccaagcccgtgagcaagatga
ggatggccaccccctgctgatgcaggctctgcccatggggccct
gccccagggccccatgcagaacgccaccaaatacggcaacatgacc -continued
gaggaccacgtgatgcacctgctgcagaacgccgatcctctgaagg
tgtacccacccctgaaaggcagcaccccgagaacctcaggcacctg
aagaacaccatggagaccatcgactggaaggtgttcgagagctgga
tgcaccactggctgctgttcgagatgagccggcacagcctggagca
gaagcccaccgacgcccctcccaaggagagcctcgagctcgaggac
ccaagcagcggcctgggcgtgaccaagcaggacctgggccccgtgc
ccatg SEQ ID NO: 9: Amino acid sequence of
hIi-HBc-2A-HBs
MHRRRSRSCREDQKPVMDDQRDLISNNEQLPMLGRRPGAPESKCSR
GALYTGFSILVTLLLAGQATTAYFLYQQQGRLDKLTVTSQNLQLEN
LRMKLPKPKPVSKMRMATPLLMQALPMGALPQGPMQNATKYGNMTE
DHVMHLLQNADPLIWYPPLKSFPENLRHLKNTMETIDWKWESWMHH
WLLFEMSRHSLEQKPTDAPPKESLELEDPSSGGVTKQDLGPVPMMD
IDPYKEFGATVELLSFLPSDFFPSVRDLLDTASALYREALESPEHC
SPHHTALRQAILCWGELMTLATANVGNNLEDPASRDLVVNYVNTNM
GLKIRQLLWFHISCLTFGRENLEYLVSFGVWIRTPPAYRPPNAPIL
STLPETTVVAPVKQTLNFDLLKLAGDVESNPGPMENITSGFLGPLL
VLQAGFFLLTRILTIPQSLDSWWTSLNFLGGSPVCLGQNSQSPTSN
HSPTSCPPICPGYRWMCLRRFIIFLFILLLCLIFLLVEDYQGMLPV
CPLIPGSTTINTGPCKTCTTPAQGNSMFPSCCCTKPTDGNCTCIPI
PSSWAFAKYLWEWASVRFSWLSLLVPFVQWFVGLSPTVWLSAIWMM
WYWGPSLYSIVSPFIPLLPIFFCLWVYI SEQ ID NO: 10: Nucleotide sequence encoding
hIi-HBc-2A-HBs
ATGCACAGGAGGAGGAGCAGGAGCTGCAGGGAGGACCAGAAGCCCG
TGATGGACGACCAGCGCGACCTGATCAGCAACAACGAGCAGCTGCC
AATGCTGGGCAGGAGGCCCGGAGCACCCGAAAGCAAGTGCAGCAGG
GGCGCCCTGTACACCGGCTTCAGCATCCTGGTGACCCTCCTGCTGG
CCGGCCAGGCCACCACCGCCTATTTCCTGTACCAGCAGCAGGGCAG
GCTCGATAAGCTGACCGTGACCTCCCAGAACCTGCAGCTGGAGAAC
CTGAGGATGAAGCTGCCCAAGCCCCCAAGCCCGTGAGCAAGATGA
GGATGGCCACCCCCTGCTGATGCAGGCTCTGCCCATGGGGGCCCT
GCCCCAGGGCCCCATGCAGAACGCCACCAAATACGGCAACATGACC
GAGGACCACGTGATGCACCTGCTGCAGAACGCCGATCCTCTGAAGG
TGTACCCACCCCTGAAAGGCAGCTTCCCCGAGAACCTCAGGCACCT
GAAGAACACCATGGAGACCATCGACTGGAAGGTGTTCGAGAGCTGG
ATGCACCACTGGCTGCTGTTCGAGATGAGCCGGCACAGCCTGGAGC
AGAAGCCCACCGACGCCCCTCCCAAGGAGAGCCTCGAGCTCGAGGA
CCCAAGCAGCGGCCTGGGCGTGACCAAGCAGGACCTGGGCCCCGTG
CCCATGGACATTGACCCCTACAAGGAGTTCGGCGCCACCGTCGAAC
TGCTGAGCTTCCTCCCCAGCGACTTCTTCCCCTCCGTGAGGGATCT -continued
GCTGGACACAGCTAGCGCCCTGTACAGGGAGGCCCTGGAGAGCCCC

GAGCACTGCAGCCCCCACCACACAGCCCTGAGGCAGGCCATCCTCT

GTTGGGGCGAGCTGATGACCCTGGCCACCTGGGTGGGCAATAACCT

GGAGGACCCCGCCAGCAGGGACCTGGTGGTCAACTACGTGAACACC

AACATGGGCCTGAAGATCAGGCAGCTGCTGTGGTTCCACATCAGCT

GCCTGACCTTTGGCAGGGAGACCGTCCTGGAGTACCTGGTGAGCTT

CGGCGTGTGGATCAGGACTCCCCCAGCCTACAGGCCCCCTAACGCC

CCCATCCTGTCTACCCTGCCCGAGACCACCGTGGTGAGGAGGAGGG

ACAGGGGCAGAAGCCCCAGGAGAAGGACCCCTAGCCCCAGGAGGAG

GAGGAGCCAGAGCCCCAGGAGGAGGAGGAGCCAGAGCCGGGAGAGC

CAGTGCGCCCCTGTGAAGCAGACCCTGAACTTCGACCTGCTGAAGC

TGGCCGGCGACGTGGAGAGCAATCCCGGCCCTATGGAAAACATCAC

CAGCGGCTTCCTGGCCCCCTGCTGGTGCTGCAGGCCGGCTTCTTC

CTGCTGACCAGGATCCTGACCATTCCCCAGTCACTGGACAGCTGGT

GGACCAGCCTGAACTTCCTCGGCGGGAGCCCCGTGTGCCTGGGCCA

GAATAGCCAGAGCCCCACCAGCAACCACTCTCCCACTTCCTGCCCC

CCTATCTGCCCCGGCTACAGGTGGATGTGCCTGAGGAGGTTCATCA

TCTTCCTGTTCATCCTGCTGCTGTGCCTGATCTTCCTGCTGGTGCT

GCTGGACTACCAGGGAATGCTGCCCGTGTGTCCCTGATCCCCGGA

AGCACCACCACCAACACCGGCCCCTGCAAGACCTGCACCACCCCCG

CCCAGGGCAACTCTATGTTCCCCAGCTGCTGCTGCACCAAGCCCAC

CGACGGCAACTGCACTTGCATTCCCATCCCCAGCAGCTGGGCCTTC

GCCAAATATCTGTGGGAGTGGGCCAGCGTGAGGTTTAGCTGGCTGA

GCCTGCTGGTGCCCTTCGTGCAGTGGTTTGTGGGCCTGAGCCCCAC

CGTGTGGCTGAGCGCCATCTGGATGATGTGGTACTGGGGCCCCTCC

CTGTACAGCATCGTGAGCCCCTTCATCCCCCTCCTGCCCATCTTCT

TCTGCCTGTGGGTGTACATC

SEQ ID NO: 11: Amino acid sequence of HBc
MDIDPYKEFGATVELLSFLPSDFFPSVRDLLDTASALYREALESPE

HCSPHHTALRQAILCWGELMTLATWVGNNLEDPASRDLVVNYVNTN

MGLKIRQLLWFHISCLTFGRETVLEYLVSFGVWIRTPPAYRPPNAP

ILSTLPETTVVRRRDRGRSPRRRTPSPRRRRSQSPRRRRSQSRESQ

C

SEQ ID NO: 12: Amino acid sequence of hIi
alternate variant
MHRRRSRSCREDQKPVMDDQRDLISNNEQLPMLGRRPGAPESKCSR

GALYTGFSILVTLLLAGQATTAYFLYQQQGRLDKLTVTSQNLQLEN

LRMKLPKPPKPVSKMRMATPLLMQALPMGALPQGPMQNATKYGNMT

EDHVMHLLQNADPLIMPPLKGSFPENLRHLKNTMETIDWKWESWMH

HWLLFEMSRHSLEQKPTDAPPKESLELEDPSSGLGVTKQDLGPVP

SEQ ID NO: 13: Nucleotide sequence encoding
hI alternate variant
ATGCACAGGAGGAGAAGCAGGAGCTGTCGGGAAGATCAGAAGCCA

GTCATGGATGACCAGCGCGACCTTATCTCCAACAATGAGCAACTG

CCCATGCTGGGCCGGCGCCCTGGGGCCCCGGAGAGCAAGTGCAGC

CGCGGAGCCCTGTACACAGGCTTTTCCATCCTGGTGACTCTGCTC

CTCGCTGGCCAGGCCACCACCGCCTACTTCCTGTACCAGCAGCAG

GGCCGGCTGGACAAACTGACAGTCACCTCCCAGAACCTGCAGCTG

GAGAACCTGCGCATGAAGCTTCCCAAGCCTCCCAAGCCTGTGAGC

AAGATGCGCATGGCCACCCCGCTGCTGATGCAGGCGCTGCCCATG

GGAGCCCTGCCCCAGGGGCCCATGCAGAATGCCACCAAGTATGGC

AACATGACAGAGGACCATGTGATGCACCTGCTCCAGAATGCTGAC

CCCCTGAAGGTGTACCGCCACTGAAGGGGAGCTTCCCGGAGAAC

CTGAGACACCTTAAGAACACCATGGAGACCATAGACTGGAAGGTC

TTTGAGAGCTGGATGCACCATTGGCTCCTGTTTGAAATGAGCAGG

CACTCCTTGGAGCAAAAGCCCACTGACGCTCCACCGAAAGAGTCA

CTGGAACTGGAGGACCCGTCTTCTGGGCTGGGTGTGACCAAGCAG

GATCTGGGCCCAGTCCCC

SEQ ID NO: 14: Alternative nucleic acid
sequence of hIi-HBc-2A-HBs
ATGCACAGGAGGAGAAGCAGGAGCTGTCGGGAAGATCAGAAGCCA

GTCATGGATGACCAGCGCGACCTTATCTCCAACAATGAGCAACTG

CCCATGCTGGGCCGGCGCCCTGGGGCCCCGGAGAGCAAGTGCAGC

CGCGGAGCCCTGTACACAGGCTTTTCCATCCTGGTGACTCTGCTC

CTCGCTGGCCAGGCCACCACCGCCTACTTCCTGTACCAGCAGCAG

GGCCGGCTGGACAAACTGACAGTCACCTCCCAGAACCTGCAGCTG

GAGAACCTGCGCATGAAGCTTCCCAAGCCTCCCAAGCCTGTGAGC

AAGATGCGCATGGCCACCCCGCTGCTGATGCAGGCGCTGCCCATG

GGAGCCCTGCCCCAGGGGCCCATGCAGAATGCCACCAAGTATGGC

AACATGACAGAGGACCATGTGATGCACCTGCTCCAGAATGCTGAC

CCCCTGAAGGTGTACCGCCACTGAAGGGGAGCTTCCCGGAGAAC

CTGAGACACCTTAAGAACACCATGGAGACCATAGACTGGAAGGTC

TTTGAGAGCTGGATGCACCATTGGCTCCTGTTTGAAATGAGCAGG

CACTCCTTGGAGCAAAAGCCCACTGACGCTCCACCGAAAGAGTCA

CTGGAACTGGAGGACCCGTCTTCTGGGCTGGGTGTGACCAAGCAG

GATCTGGGCCCAGTCCCCATGGACATTGACCCTTATAAAGAATTT

GGAGCTACTGTGGAGTTACTCTCGTTTTTGCCTTCTGACTTCTTT

CCTTCCGTCAGAGATCTCCTAGACACCGCCTCAGCTCTGTATCGA

GAAGCCTTAGAGTCTCCTGAGCATTGCTCACCTCACCATACTGCA

CTCAGGCAAGCCATTCTCTGCTGGGGGGAATTGATGACTCTAGCT

ACCTGGGTGGGTAATAATTTGGAAGATCCAGCATCCAGGGATCTA

GTAGTCAATTATGTTAATACTAACATGGGTTTAAAGATCAGGCAA

-continued
```
CTATTGTGGTTTCATATATCTTGCCTTACTTTTGGAAGAGAGACT

GTACTTGAATATTTGGTCTCTTTCGGAGTGTGGATTCGCACTCCT

CCAGCCTATAGACCACCAAATGCCCCTATCTTATCAACACTTCCG

GAAACTACTGTTGTTAGACGACGGGACCGAGGCAGGTCCCCTAGA

AGAAGAACTCCCTCGCCTCGCAGACGCAGATCTCAATCGCCGCGT

CGCAGAAGATCTCAATCTCGGGAATCTCAATGTGCCCCTGTGAAG

CAGACCCTGAACTTCGACCTGCTGAAGCTGGCCGGCGACGTGGAG

AGCAATCCCGGCCCTATGGAGAACATCACATCAGGATTCCTAGGA

CCCCTGCTCGTGTTACAGGCGGGGTTTTTCTTGTTGACAAGAATC

CTCACAATACCGCAGAGTCTAGACTCGTGGTGGACTTCTCTCAAT

TTTCTAGGGGGATCACCCGTGTGTCTTGGCCAAAATTCGCAGTCC

CCAACCTCCAATCACTCACCAACCTCCTGTCCTCCAATTTGTCCT

GGTTATCGCTGGATGTGTCTGCGGCGTTTTATCATATTCCTCTTC

ATCCTGCTGCTATGCCTCATCTTCTTATTGGTTCTTCTGGATTAT

CAAGGTATGTTGCCCGTTTGTCCTCTAATTCCAGGATCAACAACA

ACCAATACGGGACCATGCAAAACCTGCACGACTCCTGCTCAAGGC

AACTCTATGTTTCCCTCATGTTGCTGTACAAAACCTACGGATGGA

AATTGCACCTGTATTCCCATCCCATCGTCCTGGGCTTTCGCAAAA

TACCTATGGGAGTGGGCCTCAGTCCGTTTCTCTTGGCTCAGTTTA

CTAGTGCCATTTGTTCAGTGGTTCGTAGGGCTTTCCCCCACTGTT

TGGCTTTCAGCTATATGGATGATGTGGTATTGGGGCCAAGTCTG

TACAGCATCGTGAGTCCCTTTATACCGCTGTTACCAATTTTCTTT

TGTCTCTGGGTATACATT
```

SEQ ID NO: 15: Alternative amino acid sequence of hIi-HBc-2A-HBs
```
MHRRRSRSCREDQKPVMDDQRDLISNNEQLPMLGRRPGAPESKCS

RGALYTGFSILVTLLLAGQATTAYFLYQQQGRLDKLTVTSQNLQL

ENLRMKLPKPPKPVSKMRMATPLLMQALPMGALPQGPMQNATKYG

NMTEDHVMHLLQNADPLIMPPLKGSFPENLRHLKNTMETIDWKWE

SWMHHWLLFEMSRHSLEQKPTDAPPKESLELEDPSSGLGVTKQDL

GPVPMDIDPYKEFGATVELLSFLPSDFFPSVRDLLDTASALYREA

LESPEHCSPHHTALRQAILCWGELMTLATWVGNNLEDPASRDLVV

NYVNTNMGLKIRQLLWFHISCLTFGRENLEYLVSFGVWIRTPPAY

RPPNAPILSTLPETTVVRRRDRGRSPRRRTPSPRRRRSQSPRRRR

SQSRESQCAPVKQTLNFDLLKLAGDVESNPGPMENITSGFLGPLL

VLQAGFFLLTRILTIPQSLDSWWTSLNFLGGSPVCLGQNSQSPTS

NHSPTSCPPICPGYRWMCLRRFIIFLFILLLCLJFLLVLLDYQGM

LPVCPLIPGSTTTNTGPCKTCTTPAQGNSMFPSCCCTKPTDGNCT

CIPIPSSWAFAKYLWEWASVRFSWLSLLVPFVQWFVGLSPTVWLS

AIWMMWYWGPSLYSIVSPFIPLLPIFFCLWVYI
```

REFERENCES

Al-Mahtab M, Akbar S M, Aguilar J C, Uddin M H, Khan M S, Rahman S. Therapeutic potential of a combined hepatitis B virus surface and core antigen vaccine in patients with chronic hepatitis B. *Hepatol Int* 2013; 7(4): 981-9.

Bedossa P, Poynard T. An algorithm for the grading of activity in chronic hepatitis C. The METAVIR Cooperative Study Group. *Hepatology*. 1996; 24(2):289-93.

Bertoletti A, Ferrari C. Innate and adaptive immune responses in chronic hepatitis B virus infections: towards restoration of immune control of viral infection. *Gut.* 2012; 61(12):1754-64.

Block T M, Locarnini S, McMahon B J, Rehermann B, Peters M G. Use of Current and New Endpoints in the Evaluation of Experimental Hepatitis B Therapeutics. *Clin Infect Dis*. 2017; 64(9):1283-1288.

Boni C, Laccabue D, Lampertico P, et al. Restored function of HBV-specific T cells after long-term effective therapy with nucleos(t)ide analogues. *Gastroenterology.* 2012; 143(4):963-73.e9.

Borghese F, Clanchy F I. CD74: an emerging opportunity as a therapeutic target in cancer and autoimmune disease. *Expert Opin Ther Targets*. 2011; 15(3):237-51.

Buchmann P, Dembek C, Kuklick L, et al Novel therapeutic hepatitis B vaccine induces cellular and humoral immune responses and breaks tolerance in hepatitis B virus (HBV) transgenic mice. *Vaccine*. 2013; 31(8):1197-203.

Cavenaugh J S, Awi D, Mendy M, et al. Partially Randomized, Non-Blinded Trial of DNA and MVA Therapeutic Vaccines Based on Hepatitis B Virus Surface Protein for Chronic HBV Infection. *PLoS ONE* 2011; 6:1-14.

Capone S, Naddeo M, D'Alise A M, et al. Fusion of HCV nonstructural antigen to MHC class II-associated invariant chain enhances T-cell responses induced by vectored vaccines in nonhuman primates. *Mol Ther.* 2014; 22(5): 1039-47.

Cornberg M, Wong V W, Locarnini S, Brunetto M, Janssen H L, Chan H L. The role of quantitative hepatitis B surface antigen revisited. *J Hepatol*. 2017; 66(2):398-411.

Di Lullo, G., E. Soprana, M. Panigada, A. Palini, A. Agresti, C. Comunian, A. Milani, I. Capua, V. Erfle and A. G. Siccardi (2010). The combination of marker gene swapping and fluorescence-activated cell sorting improves the efficiency of recombinant modified vaccinia virus Ankara vaccine production for human use. Journal of Virological Methods 163(2): 195-204

Dion S, Bourgine M, Godon O, Levillayer F, Michel M L. Adeno-associated virus-mediated gene transfer leads to persistent hepatitis B virus replication in mice expressing HLA-A2 and HLA-DR1 molecules. *J Virol* 2013; 87(10): 5554-63.

Donnelly M L, Luke G, Mehrotra A, Li X, Hughes L E, Gani D, Ryan M D. Analysis of the aphthovirus 2A/2B polyprotein 'cleavage' mechanism indicates not a proteolytic reaction, but a novel translational effect: a putative ribosomal 'skip'. *J Gen Virol*. 2001 May; 82 (Pt 5):1013-25

Durantel D, Zoulim F. New antiviral targets for innovative treatment concepts for hepatitis B virus and hepatitis delta virus. *J Hepatol* 2016; 64; S117-S131.

EASL 2017. Clinical Practice Guidelines on the management of hepatitis B virus infection. *J Hepatol* 2017; 67(2), 370-398.

Fontaine H, Kahi S, Chazallon C, et al. Anti-HBV DNA vaccination does not prevent relapse after discontinuation of analogues in the treatment of chronic hepatitis B: a randomised trial—ANRS HB02 VAC-ADN. *Gut.* 2015; 64:139-147.

Hilgers et al., Synergistic Effects of Synthetic Adjuvants on the Humoral Immune Response. Int. Arch. Allergy. Immunol. 1986, 79(4):392-6;

Hilgers et al., Novel adjuvants for humoral immune responses. *Immunology,* 1987, 60(1):141-6

Jung M C, Gruner N, Zachoval R, et al. Immunological monitoring during therapeutic vaccination as a prerequisite for the design of new effective therapies: induction of a vaccine-specific CD4+ T-cell proliferative response in chronic hepatitis B carriers. *Vaccine.* 2002; 20(29-30): 3598-612.

Kensil C R et al. Separation and characterization of saponins with adjuvant activity from *Quillaja saponaria* Molina cortex. *J. Immunology*(1991) 146: 431-437.

Kensil C R, Saponins as Vaccine Adjuvants. *Crit. Rev. Ther. Drug Carrier Syst.,* 1996, 13:1-55;

Kittel B, Ruehl-Fehlert C, Morawietz G, et al. Revised guides for organ sampling and trimming in rats and mice—Part 2. A joint publication of the RITA and NACAD groups. *Exp Toxicol Pathol.* 2004; 55(6):413-31.

Kranidioti H, Manolakopoulos S, Khakoo S I. Outcome after discontinuation of nucleot(s)ide analogues in chronic hepatitis B: relapse rate and associated factors. *Ann GastroenteroZ* 2015; 28(2):173-181.

Lau G K, Suri D, Liang R, et al. Resolution of Chronic Hepatitis B and Anti-HBs Seroconversion in Humans by Adoptive Transfer of Immunity to Hepatitis B Core Antigen. *Gastroenterology* 2002; 122:614-24.

Lacaille-Dubois, M and Wagner H, A review of the biological and pharmacological activities of saponins. Phytomedicine vol 2 pp 363-386 (1996).

Li J, Han Y, Jin K, et al. Dynamic changes of cytotoxic T lymphocytes (CTLs), natural killer (NK) cells, and natural killer T (NKT) cells in patients with acute hepatitis B infection. *Virol J.* 2011; 8:199.

Liang M, Ma S, Hu X, et al. Cellular immune responses in patients with hepatitis B surface antigen seroclearance induced by antiviral therapy. *Virol J.* 2011; 8:69.

Liaw Y F. Impact of therapy on the long-term outcome of chronic hepatitis B. *Clin Liver Dis.* 2013; 17:413-423.

Liaw Y F, Chu C M. Hepatitis B virus infection. Lancet 2009; 373, 582-592.

Lok A S, Pan C Q, Han S H, et al. Randomized phase II study of GS-4774 as a therapeutic vaccine in virally suppressed patients with chronic hepatitis B. *J Hepatol.* 2016; 65(3):509-16.

Lorin C, Vanloubbeeck Y, Baudart S, et al. Heterologous prime-boost regimens with a recombinant chimpanzee adenoviral vector and adjuvanted F4 protein elicit polyfunctional HIV-1-specific T-Cell responses in macaques. *PLoS One.* 2015; 10(4):e0122835.

Maini M, Gehring A, The role of innate immunity in the immunopathology and treatment of HBV infection. J Hepato/2016; 64; 560-570.

Martin P, Furman R R, Rutherford S, et al. Phase I study of the anti-CD74 monoclonal antibody milatuzumab (hLL1) in patients with previously treated B-cell lymphomas. *Leuk Lymphoma.* 2015; 12:1-6.

Mayr A, Stickl H, Muller H K, Danner K, Singer, H. The smallpox vaccination strain MVA: marker, genetic structure, experience gained with the parenteral vaccination and behavior in organisms with a debilitated defense mechanism. Zentralblatt fur Bakteriologie, Parasitenkunde, Infektionskrankheiten und Hygiene Erste Abteilung Originale Reihe B: Hygiene, Betriebshygiene, praventive Medizin. 1978; 167:375-90.

Mayr, A., Hochstein-Mintzel, V. & Stickl, H. (1975). Infection 3, 6-14.

McInnes K J, Smith L B, Hunger N I, Saunders P T, Andrew R, Walker B R. Deletion of the androgen receptor in adipose tissue in male mice elevates retinol binding protein 4 and reveals independent effects on visceral fat mass and on glucose homeostasis. *Diabetes.* 2012; 61(5): 1072-81.

Mohamadnejad M, Tavangar S M, Sotoudeh M, et al. Histopathological Study of Chronic Hepatitis B: A Comparative Study of Ishak and METAVIR Scoring Systems. *Int J Organ Transplant Med.* 2010; 1(4):171-6.

Morawietz G, Ruehl-Fehlert C, Kittel B, et al. Revised guides for organ sampling and trimming in rats and mice—Part 3. A joint publication of the RITA and NACAD groups. *Exp Toxicol Pathol* 2004; 55(6):433-49.

Neumann A U, Phillips S, Levine I, et al. Novel mechanism of antibodies to hepatitis B virus in blocking viral particle release from cells. *Hepatology.* 2010; 52(3):875-85.

Ott J J, Stevens G A, Groeger J, Wiersma S T. Global epidemiology of hepatitis B virus infection: new estimates of age-specific HBsAg seroprevalence and endemicity. *Vaccine* 2012; 30:2212-19.

Rammeh S, Khadra H B, Znaidi N S, et al. Inter-observes agreement of Ishak and Metavir scores in histological evaluation of chronic viral hepatitis B and C. *Ann Biot Clin* (Paris). 2014; 72(1):57-60.

Rehermann B, Nascimbeni M. Immunology of hepatitis B virus and hepatitis C virus infection. *Nat Rev Immunol* 2005; 5(3):215-29.

Riedl P, Reiser M, Stifter K, Krieger J, Schirmbeck R. Differential presentation of endogenous and exogenous hepatitis B surface antigens influences priming of CD8(+) T cells in an epitope-specific manner. *Eur J Immunol* 2014; 44(7):1981-91.

Ruehl-Fehlert C, Kittel B, Morawietz G, et al. Revised guides for organ sampling and trimming in rats and mice-part 1. *Exp Toxicol Path.* 2003; 55(2-3):91-106.

Spencer A J, Cottingham M G, Jenks J A, et al Enhanced vaccine-induced CD8+ T cell responses to malaria antigen ME-TRAP by fusion to MHC class ii invariant chain. *PLoS One.* 2014; 9(6):e100538.

Terrault N A, Bzowej N H, Chang K-M, et al AASLD Guidelines for Treatment of Chronic Hepatitis B. Hepatology. 2015; DOI:10.1002/hep.28156.

World Health Organization (WHO). Global Hepatitis report, 2017. http://apps.who.int/iris/bitstream/10665/255016/1/9789241565455-eng.pdf?ua=1. Accessed November 2017.

Yang F Q, Yu Y Y, Wang G Q, et al A pilot randomized controlled trial of dual-plasmid HBV DNA vaccine mediated by in vivo electroporation in chronic hepatitis B patients under lamivudine chemotherapy. *J Viral Hepat.* 2012; 19:581-593.

Zoutendijk R, Hansen B E, van Vuuren A J, Boucher C A, Janssen H L. Serum HBsAg decline during long-term potent nucleos(t)ide analogue therapy for chronic hepatitis B and prediction of HBsAg loss. *J Infect Dis.* 2011; 204(3):415-8.

What is claimed is:

1. An immunogenic composition comprising a Modified Vaccinia Virus Ankara (MVA) vector comprising a polynucleotide encoding a hepatitis B surface antigen (HBs) and a polynucleotide encoding a hepatitis B virus core antigen (HBc), wherein the polynucleotides encoding HBs and HBc are separated by a polynucleotide encoding the 2A cleaving region of the foot and mouth disease virus (FMDV).

2. An immunogenic composition comprising a recombinant hepatitis B surface antigen (HBs), a C-terminal truncated recombinant hepatitis B virus core antigen (HBc), and an adjuvant containing MPL and QS-21; wherein the ratio of recombinant HBc to recombinant HBs in the composition is about 1.5:1, 2:1, 2.5:1, 3:1, 3.5:1, 4:1, 4.5:1, 5:1, 5.5:1, or 6:1.

3. An immunogenic combination comprising:
a) a composition comprising a replication-defective chimpanzee adenoviral (ChAd) vector comprising a polynucleotide encoding a hepatitis B surface antigen (HBs) and a polynucleotide encoding a hepatitis B virus core antigen (HBc);
b) a composition comprising a Modified Vaccinia Virus Ankara (MVA) vector comprising a polynucleotide encoding a hepatitis B surface antigen (HBs) and a polynucleotide encoding a hepatitis B virus core antigen (HBc), wherein the polynucleotides encoding HBs and HBc are separated by a polynucleotide encoding the 2A cleaving region of the foot and mouth disease virus (FMDV); and
c) a composition comprising a recombinant hepatitis B surface antigen (HBs), a recombinant hepatitis B virus core antigen (HBc) comprising amino acids 1-145, 1-146, 1-147, 1-148, or 1-149 of a wild-type hepatitis B virus core antigen protein, and an adjuvant.

4. The immunogenic combination according to claim 3, wherein the ChAd vector of component a) of the combination further comprises a polynucleotide encoding the human invariant chain (hli) fused to the HBc, the recombinant HBc of component c) of the combination is C-terminal truncated, the adjuvant of component c) of the combination contains MPL and QS-21, and the ratio of recombinant HBc to recombinant HBs of component c) of the combination is about 1.5:1, 2:1, 2.5:1, 3:1, 3.5:1, 4:1, 4.5:1, 5:1, 5.5:1, or 6:1.

5. A kit comprising the following components:
a) a composition comprising a replication-defective chimpanzee adenoviral (ChAd) vector comprising a polynucleotide encoding a hepatitis B surface antigen (HBs) and a polynucleotide encoding a hepatitis B virus core antigen (HBc);
b) a composition comprising a Modified Vaccinia Virus Ankara (MVA) vector comprising a polynucleotide encoding a hepatitis B surface antigen (HBs) and a polynucleotide a hepatitis B virus core antigen (HBc), wherein the polynucleotides encoding HBs and HBc are separated by a polynucleotide encoding the 2A cleaving region of the foot and mouth disease virus (FMDV); and
c) a composition comprising a recombinant hepatitis B surface antigen (HBs), a recombinant hepatitis B virus core antigen (HBc) comprising amino acids 1-145, 1-146, 1-147, 1-148, or 1-149 of a wild-type hepatitis B core antigen protein, and an adjuvant,
with instructions for administration of the components sequentially or concomitantly for the treatment of chronic hepatitis B (CHB).

6. The immunogenic combination according to claim 3, wherein the HBc of component b) comprises SEQ ID NO:11 or an amino acid sequence at least 98% homologous thereto and the HBs of component b) comprises SEQ ID NO:1 or an amino acid sequence at least 98% homologous thereto, wherein the polynucleotides encoding the HBc and HBs of component b) are separated by a polynucleotide encoding an amino acid sequence comprising SEQ ID NO:3, or an amino acid sequence at least 98% homologous thereto.

7. The immunogenic combination according to claim 3, wherein the MVA vector of component b) comprises a polynucleotide encoding the amino acid sequence of SEQ ID NO:5.

8. The immunogenic combination according to claim 3, wherein the MVA vector of component b) comprises a polynucleotide having the nucleotide sequence of SEQ ID NO:6.

9. The immunogenic combination according to claim 3, wherein the composition of component c) comprises a recombinant HBs (SEQ ID NO:1), a recombinant HBc comprising amino acids 1-149 (SEQ ID NO:2) and an adjuvant comprising MPL, QS-21 and liposomes composed of dioleoyl phosphatidylcholine (DOPC) and cholesterol in a phosphate buffered saline solution.

* * * * *